(12) United States Patent
Wright

(10) Patent No.: US 11,730,935 B2
(45) Date of Patent: Aug. 22, 2023

(54) METHOD FOR APPLYING ELECTRICALLY SPUN FIBERS TO A SITE OF INTEREST

(71) Applicant: Octet Medical, Inc., San Diego, CA (US)

(72) Inventor: Clifford A. Wright, San Diego, CA (US)

(73) Assignee: Octet Medical, Inc., San Diego, CA (US)

( * ) Notice: Subject to any disclaimer, the term of this patent is extended or adjusted under 35 U.S.C. 154(b) by 0 days.

(21) Appl. No.: 17/482,519

(22) Filed: Sep. 23, 2021

(65) Prior Publication Data

US 2022/0105327 A1 Apr. 7, 2022

Related U.S. Application Data

(63) Continuation of application No. 16/772,369, filed as application No. PCT/US2019/061963 on Nov. 18, 2019, now Pat. No. 11,207,510.
(Continued)

(51) Int. Cl.
*B29C 48/16* (2019.01)
*B29C 48/92* (2019.01)
(Continued)

(52) U.S. Cl.
CPC ....... *A61M 35/00* (2013.01); *A61F 13/00991* (2013.01); *A61M 35/003* (2013.01); *B05B 5/0403* (2013.01); *B05B 5/0415* (2013.01); *B05B 5/1691* (2013.01); *B05B 11/0054* (2013.01); *B29C 31/042* (2013.01);
(Continued)

(58) Field of Classification Search
CPC ....... B29C 31/042; B29C 48/16; B29C 48/92; B29C 70/78; B29C 71/02; B29C 2948/92009; B29C 2948/92047; B29C 2948/92104; D01D 5/0007; D01D 5/0015;
(Continued)

(56) References Cited

U.S. PATENT DOCUMENTS

| 4,120,016 A | 10/1978 | Hendricks |
| 4,120,017 A | 10/1978 | Sickles |

(Continued)

FOREIGN PATENT DOCUMENTS

| CN | 203754859 U | * | 8/2014 | ............. D01D 5/00 |
| CN | 104480640 A | * | 4/2015 | .......... D01D 5/0007 |

(Continued)

OTHER PUBLICATIONS

Translation of CN 104480640 A (published on Apr. 1, 2015).*
(Continued)

*Primary Examiner* — Leo B Tentoni
(74) *Attorney, Agent, or Firm* — Snell & Wilmer L.L.P.

(57) ABSTRACT

An applicator is disclosed for applying a treatment solution to a treatment site of a patient. The applicator can include an applicator housing comprising a treatment solution reservoir. A cartridge can be removably disposed in the housing. The cartridge when arranged in the housing can be in fluid communication with the treatment solution reservoir. The cartridge can include an electrostatic module for electrostatically charging the treatment solution in the treatment solution reservoir; and a nozzle for applying the treatment solution.

16 Claims, 34 Drawing Sheets

Related U.S. Application Data

(60) Provisional application No. 62/882,945, filed on Aug. 5, 2019, provisional application No. 62/878,250, filed on Jul. 24, 2019, provisional application No. 62/769,511, filed on Nov. 19, 2018.

(51) Int. Cl.

| | | |
|---|---|---|
| *B29C 70/78* | (2006.01) | |
| *B29C 71/02* | (2006.01) | |
| *D02J 13/00* | (2006.01) | |
| *A61M 35/00* | (2006.01) | |
| *A61F 13/00* | (2006.01) | |
| *D01D 5/00* | (2006.01) | |
| *D01D 5/084* | (2006.01) | |
| *D01D 5/18* | (2006.01) | |
| *D01F 8/04* | (2006.01) | |
| *D04H 1/728* | (2012.01) | |
| *B29C 48/02* | (2019.01) | |
| *B05B 5/04* | (2006.01) | |
| *B05B 5/16* | (2006.01) | |
| *B05B 11/00* | (2023.01) | |
| *B29C 31/04* | (2006.01) | |
| *D01F 1/10* | (2006.01) | |
| *G01N 21/17* | (2006.01) | |

(52) U.S. Cl.
CPC .......... *B29C 48/02* (2019.02); *D01D 5/003* (2013.01); *D01D 5/0007* (2013.01); *D01D 5/0015* (2013.01); *D01D 5/0023* (2013.01); *D01D 5/0038* (2013.01); *D01D 5/0061* (2013.01); *D01D 5/0069* (2013.01); *D01D 5/0084* (2013.01); *D01D 5/0092* (2013.01); *D01D 5/084* (2013.01); *D01D 5/18* (2013.01); *D01F 1/103* (2013.01); *D01F 8/04* (2013.01); *D04H 1/728* (2013.01); *B29C 2948/92009* (2019.02); *B29C 2948/92047* (2019.02); *B29C 2948/92104* (2019.02); *D10B 2509/022* (2013.01); *G01N 2021/1746* (2013.01)

(58) Field of Classification Search
CPC .. D01D 5/0023; D01D 5/0038; D01D 5/0084; D01D 10/02; D01F 1/103; D02J 13/00
USPC .......... 264/40.1, 40.7, 171.1, 211, 234, 464, 264/465, 466, 484
See application file for complete search history.

(56) References Cited

U.S. PATENT DOCUMENTS

| | | | |
|---|---|---|---|
| 4,971,257 | A | 11/1990 | Birge |
| 6,311,903 | B1 | 11/2001 | Gaw et al. |
| 7,712,687 | B2 | 5/2010 | Wilson et al. |
| 7,823,808 | B2 | 11/2010 | Yamaguchi et al. |
| 8,780,432 | B1 | 7/2014 | Nguyen |
| 8,833,679 | B2 | 9/2014 | Bryant et al. |
| 8,893,990 | B2 | 11/2014 | Seitz et al. |
| 10,322,424 | B2 | 6/2019 | Wright |
| 10,589,298 | B2 | 3/2020 | Wright |
| 10,994,291 | B2 | 5/2021 | Wright |
| 11,207,510 | B2 | 12/2021 | Wright |
| 2001/0020652 | A1 | 9/2001 | Kadlubowski et al. |
| 2003/0031586 | A1 | 2/2003 | Eckhardt et al. |
| 2006/0195059 | A1 | 8/2006 | Freyman et al. |
| 2006/0228435 | A1 | 10/2006 | Andrady et al. |
| 2007/0045777 | A1 | 3/2007 | Gillies et al. |
| 2010/0072309 | A1 | 3/2010 | Hodge et al. |
| 2011/0148006 | A1 | 2/2011 | Nagayama et al. |
| 2011/0278751 | A1 | 11/2011 | Ishikawa et al. |
| 2012/0082744 | A1 | 4/2012 | Jo et al. |
| 2013/0131633 | A1 | 5/2013 | Mudd et al. |
| 2013/0309414 | A1 | 11/2013 | Eskra et al. |
| 2014/0005470 | A1 | 1/2014 | Soletti et al. |
| 2014/0061959 | A1 | 3/2014 | Maly et al. |
| 2014/0110492 | A1 | 4/2014 | Cooper |
| 2014/0159263 | A1 | 6/2014 | Lozano et al. |
| 2014/0323993 | A1 | 10/2014 | Wilcox et al. |
| 2016/0047075 | A1* | 2/2016 | Foley .................. D01D 5/0084 264/465 X |
| 2016/0271021 | A1 | 9/2016 | Glenn et al. |
| 2016/0325579 | A1 | 11/2016 | Shsrma et al. |
| 2017/0072224 | A1 | 3/2017 | Frohwitter |
| 2017/0145593 | A1 | 5/2017 | Nakagawa et al. |
| 2017/0173607 | A1 | 6/2017 | Wright |
| 2017/0239094 | A1 | 8/2017 | Dubson |
| 2018/0085765 | A1 | 3/2018 | Wright |
| 2018/0245243 | A1 | 8/2018 | Krieger et al. |
| 2019/0060922 | A1 | 2/2019 | Wright |
| 2019/0153624 | A1 | 5/2019 | Sugawara |
| 2020/0121867 | A1 | 4/2020 | Wright |

FOREIGN PATENT DOCUMENTS

| | | | | |
|---|---|---|---|---|
| CN | 107904687 | A | 4/2018 | |
| EP | 1417039 | | 11/2006 | |
| EP | 1478470 | | 4/2008 | |
| EP | 1349669 | | 7/2008 | |
| EP | 2387472 | | 11/2011 | |
| EP | 3355112 | A1 * | 8/2018 | .......... D01D 5/0061 |
| JP | 07-194997 | | 8/1995 | |
| JP | 2011-102455 | | 5/2011 | |
| KR | 20100024122 | A * | 3/2010 | ............. A61L 15/42 |
| KR | 101635027 | | 6/2016 | |
| WO | 96/40441 | | 12/1996 | |
| WO | 2012/097360 | | 7/2012 | |
| WO | 2012/109251 | | 8/2012 | |
| WO | 2015/002418 | | 1/2015 | |
| WO | 2016/156772 | | 10/2016 | |

OTHER PUBLICATIONS

Translation of KR 20100024122 A (published on Mar. 5, 2010).*
Non-Final Office Action dated Mar. 7, 2022 in U.S. Appl. No. 17/566,413.
Notice of Allowance dated May 3, 2022 in U.S. Appl. No. 17/566,413.
Non-Final Office Action dated Sep. 2, 2021 in U.S. Appl. No. 16/772,369.
Notice of Allowance dated Sep. 22, 2021 in U.S. Appl. No. 16/772,369.
Zhao, "Electrical fields in wound healing—An overriding signal that directs cell migration", Seminars in Cell & Developmental Biology, doi:10.1016/j.semcdb.2008.12.009 (2009).
Tai et al., "Electrically stimulated cell migration and its contribution to wound healing," Burns & Trauma, 6:20, https://doi.org/10.1186/s41038-018-0123-2 (2018).
Saunders et al., "Delivery of human fibroblast cells by piezoelectric drop-on-demand inkjet printing", Biomaterials 29, pp. 193-203 (2008).
International Search Report and Written Opinion dated Mar. 19, 2020 in PCT International Patent Application No. PCT/US2019/061963.

* cited by examiner

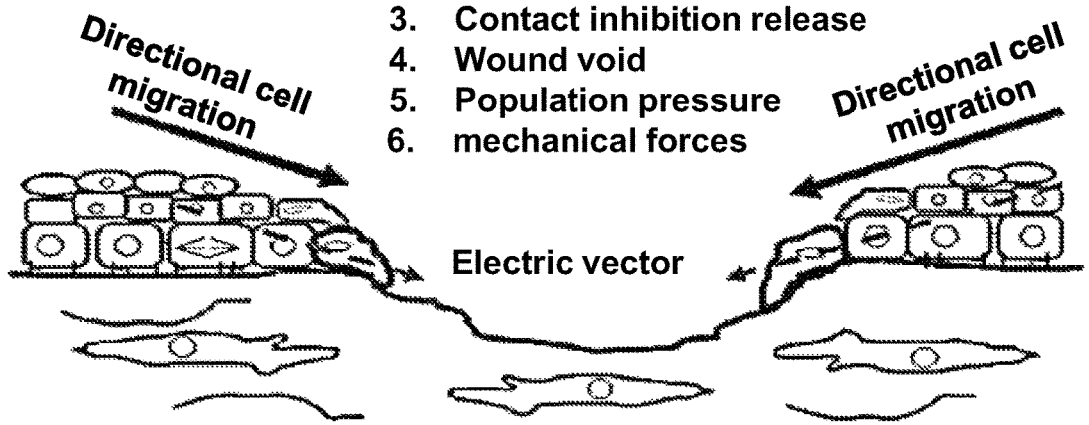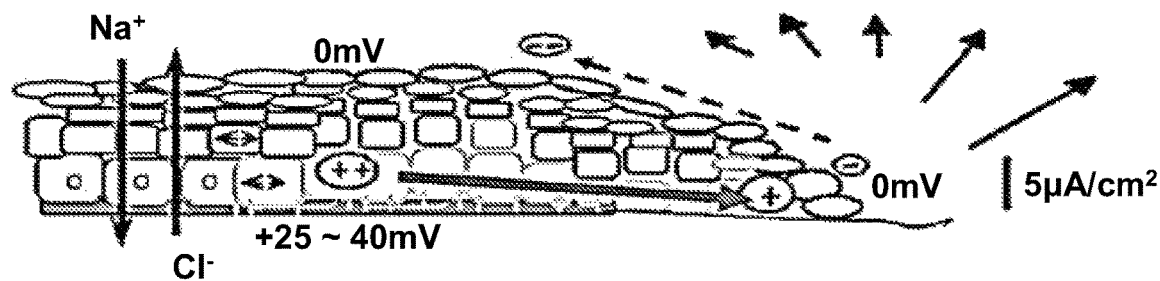
Fig. 25

3000

```
electrostatically charging a treatment solution for a
treatment site of a patient
3010
```

```
uniformly applying, by an applicator, the treatment
solution on the treatment site of the patient
3020
```

3100

```
┌─────────────────────────────────────────┐
│ electrostatically charging a treatment  │
│   solution for a treatment site of a    │
│                patient                  │
│                 3110                    │
└─────────────────────────────────────────┘
                    ↓
┌─────────────────────────────────────────┐
│ uniformly applying, by an applicator,   │
│  the treatment solution on the treatment│
│          site of the patient            │
│                 3120                    │
└─────────────────────────────────────────┘
                    ↓
┌─────────────────────────────────────────┐
│ forming the treatment solution with a   │
│ tracking material mixed with at least   │
│ one stem cells and/or a disinfectant    │
│         for the treatment site          │
│                 3130                    │
└─────────────────────────────────────────┘
                    ↓
┌─────────────────────────────────────────┐
│ authenticating, with an optical reader  │
│   external to the applicator, contents  │
│         of the treatment solution       │
│                 3140                    │
└─────────────────────────────────────────┘
                    ↓
┌─────────────────────────────────────────┐
│  if authentic, then carrying out the    │
│  step of uniformly applying, by the     │
│  applicator, the treatment solution on  │
│     the treatment site of the patient   │
│                 3150                    │
└─────────────────────────────────────────┘
```

Fig. 31

3200 applying electric potentials to a treatment solution of a cartridge in an applicator for producing the liquid bandage on a treatment site
3210 electrospinning, by the rotatable needle, the treatment solution
3220

METHOD FOR APPLYING ELECTRICALLY SPUN FIBERS TO A SITE OF INTEREST

CROSS-REFERENCE TO RELATED APPLICATIONS

This application is a continuation of U.S. patent application Ser. No. 16/772,369, filed on Jun. 12, 2020, now U.S. Pat. No. 11,207,510, which is a U.S. national stage entry under 35 U.S.C. § 371 of International Application No. PCT/US2019/061963, filed on Nov. 18, 2019, which claims priority to and benefit of U.S. Provisional Application Ser. No. 62/769,511, filed on Nov. 19, 2018, and claims priority to, and the benefit of, U.S. Provisional Application Ser. No. 62/878,250, filed on Jul. 24, 2019, and claims priority to, and the benefit of, U.S. Provisional Application Ser. No. 62/882,945, filed on Aug. 5, 2019, the contents of which are incorporated into this application by reference in their entirety.

FIELD

The solution of this disclosure relates to devices, systems, and methods for uniformly applying solutions to patients. More specifically, the devices, systems and methods are directed towards solutions for treatment surfaces on patients, including skin wounds.

BACKGROUND

Infectious disease is too often acquired in places that should be safe, such as ambulances, hospitals, clinical settings, and other areas such as assisted living facilities. The traditional ways of spraying disinfectants on patients or subjects are no longer effective. Much of how the medical industry has evolved over the years for treating patients with disinfectant issues, such as skin wounds, includes advances in the use of stem cells applied to the wound as well as genetic specific treatments. While different treatment options continue to develop, the body reacts differently to the respective form of treatments. Further, there has been a lack of focus on how to deliver these treatments in the best most economical way.

With respect to stem cells, it is understood that they are routinely grown at 37° C./5% $CO_2$ in a humidified incubator using nutrient rich media formulated to sustain the given stem cell of interest. Different trophic factors can be supplemented to the growth media to maintain stem cells healthy and expand the culture. Stem cells will proliferate in the absence of differentiation whereas cells grown at a lower temperature (e.g., <30° C.) will exhibit slow proliferation, arrest protein production and in some certain stem cells will differentiate in-vitro. Cells grown at 48° C. and increased temperatures (e.g., >52° C.) have been known to have increased risk of protein and DNA degradation in-vitro. Stem cells grown at 30° C., in-vitro, increase cell surface expression of certain receptors/ion channels and in some cases been shown to differentiate. Cell function is best at normal physiological temperature which is 98.6° F. (37° C.) but at higher temperatures the cell membrane increases in fluidity allowing for the movement of potentially harmful proteins and other molecules in and out of the cell and at >58° C. the cell is subject to apoptotic pathway which leads to cell death.

Additionally, skin grafts can take weeks or even months to heal. During the recovery period, patients are prone to infection. While researchers have regenerated skin in the lab for decades, the process is relatively long and can take 2-3 weeks. Further, the resultant skin is typically fragile and expensive to generate and maintain in culture. In certain cases, the epidermal cultures fail to take hold and there is considerable effort and reagents lost in the process. Though the skin has been grafted and/or placed on the patient's wound/burn or area of interest, blisters can form beneath due to secretions and can push up against the sheets of skin causing further damage. These problems are starting to be addressed by utilizing stem cells applied through a specialized applicator.

With respect to wound healing, the process is a complex and dynamic with multiple stages that include coordinated signaling between chemokines, cytokines, growth factors, and various cells. The disruption of this process at any stage may lead to wounds becoming chronic and/or lead to abnormal epidermal formation. A chronic wound is one that fails to heal in a predictable amount of time and detained in one or more phases (hemostasis, inflammation, proliferation, or remodeling) of wound healing which the most common being the inflammatory phase. These wounds cause patients severe emotional and physical stress and create a significant financial burden on patients and the entire healthcare system. Stem cell based therapeutic approaches have been a promising new intervention in the field of regenerative medicine for their capacity to self-renew and differentiate into multiple cell types.

Further, cell membrane integrity can be compromised by certain forces, including chemical, mechanical, and electrical forces. The amount of force/shear stress has been examined in studies delivering suspension human umbilical vein endothelial cells (HUVEC) via syringe. For example, one study found reduced acute cell viability (58.7%) when delivered at a flow rate of 1000 uL/min. See Aguado et. al. 2012. The suspending HUVEC within 75K crosslinked alginate solution (hydrogel) improved acute viability (88.9%) Similar results were seen with rat mesenchymal stem cell and human adipose stem cell (hASC).

The solution of this disclosure resolves these and other issues of the art.

SUMMARY

The subject of this disclosure is an applicator for applying a treatment solution to a treatment site of a patient.

In some examples, an applicator is disclosed for applying a treatment solution to a treatment site of a patient, the treatment solution being electrospun by the applicator for application to the treatment site. The applicator can include an applicator housing; a cartridge removably disposed in the housing, the cartridge capable of storing the treatment solution with at least one electrospinning medium when arranged in the housing; a rotatable needle with a distal nozzle tip in fluid communication with the cartridge, the distal nozzle tip configured to radially deliver electrically spun droplets of the treatment solution from the applicator to the treatment site.

In some examples, the applicator can include an auxiliary electrode in electrical communication with the cartridge when the cartridge is disposed in the housing and a motor rotatably connected to a proximal end of the rotatable needle, wherein the motor is configured to rotate the rotatable needle one or more rotational speeds. The motor spinning the needle pressurizes the treatment solution in the cartridge and drives the treatment solution out of the distal nozzle tip to create a fine mist of treatment solution.

In some examples, the applicator can include a pressure pump in fluid communication with the cartridge through a supply tube; and an electrospinning fan configured to evaporate treatment solution from the cartridge through the distal nozzle tip.

In some examples, the distal nozzle tip includes a venturi.

In some examples, the fan is configured to force fluids through the venturi thereby accelerating the fluid flow to rapidly evaporate a solvent of the treatment solution and then deliver a fine stringy matrix on the treatment site.

In some examples, the rotatable needle comprises a proximal seal and a distal seal adjacent the distal nozzle tip for pressurizing fluids inside the cartridge.

In some examples, the rotatable needle can include an elongate body with an inner lumen; a plurality of radially separated feed tube holes positioned along a length of the elongate body; and a plurality of radially separated distribution elements protruding outwardly from the distal nozzle tip, the distribution elements configured to collectively deliver a mist or stream of electrostatically charged treatment solution.

In some examples, the distribution elements taken together form a needle matrix oriented radially or any angle point forward that facilitates a predetermined spray application pattern of the treatment solution.

In some examples, the distribution elements are oriented orthogonal relative to a longitudinal axis of the rotatable needle.

In some examples, the treatment solution comprises a polymer and a solvent, and the rotatable needle is configured to be rotated, dissolve the polymer, and spray, from the distal nozzle tip, the dissolved polymer radially and then subject that treatment solution to a relatively high velocity airflow thereby drying the solvent and redirects a resultant fibrous mat to the treatment site.

In some examples, the rotatable needle is axially positioned within a needle chamber of the cartridge, the needle chamber comprising a substantially elongate lumen through a central portion of the cartridge between opposing ends thereof.

In some examples, the treatment solution includes a mixture that includes at least one of stem cells and/or a disinfectant for the treatment site.

In some examples, the electrically spun droplets form a liquid bandage comprising an electrospun fibrous mat on the treatment site.

In some examples, the fibrous mat includes at least two layers made of different electro spinning media.

In some examples, the fibrous mat includes at least one pharmaceutical agent.

In some examples, the treatment solution includes a disinfecting cartridge that includes a mixed reagent with an antimicrobial solution of certain percentage.

In some examples, the treatment solution includes a reagent comprising an analgesic property.

In some examples, the mixture further includes a tracking material for authenticating contents of the treatment solution.

In some examples, the tracking material is a silica gel capable of being viewed by an optical reader to authenticate contents of the mixture.

In some examples, the applicator housing includes a grip and an activation mechanism configured for activating the treatment solution of the applicator to be pumped through the applicator, the cartridge, and out of the distal nozzle tip.

In some examples, the cartridge is disposable.

In some examples, the applicator includes a power supply configured to produce a difference of electric potentials on the distal nozzle dip and the auxiliary electrode. The electric potential difference ranges between 5 kV to 50 kV, 20 kV to 30 kV, and/or the like. However, other ranges are contemplated as needed or required.

In some examples, the treatment site is a wound bed or an open wound.

In some examples, the treatment site is an infection on skin of the patient.

In some examples, a method of producing a liquid bandage comprising an electrospun fibrous mat is disclosed, including applying electric potentials to a treatment solution of a cartridge in an applicator for producing and delivering the liquid bandage on a treatment site. The applicator can include an applicator housing; the cartridge removably disposed in the housing and capable of storing a treatment solution with at least one electrospinning medium when arranged in the housing; a rotatable needle with a distal nozzle tip in fluid communication with the cartridge, the distal nozzle tip configured to radially deliver electrically spun droplets of the treatment solution from the applicator to the treatment site; and electrospinning, by the rotatable needle, the treatment solution.

In some examples, the method can include rotating a proximal end of the rotatable needle, by a motor rotatably connected to the proximal end of the rotatable needle, thereby pressurizing the treatment solution in the cartridge; and driving the treatment solution, by the motor rotating the rotatable needle, out of the distal nozzle tip and creating a fine mist of treatment solution on the treatment site.

In some examples, the method can include evaporating the treatment solution, by an electrospinning fan of the applicator, from the cartridge through the distal nozzle tip.

In some examples, the method can include forcing fluids, by an electrospinning fan of the applicator, through a venturi of the distal nozzle tip thereby accelerating flow of fluids to rapidly evaporate a solvent of the treatment solution and then; delivering, by the distal nozzle tip, a fine fibrous mat on the treatment site.

In some examples, the rotatable needle includes an elongate body with an inner lumen; a plurality of radially separated feed tube holes positioned along a length of the elongate body; and a plurality of radially separated distribution elements protruding outwardly from the distal nozzle tip, the distribution elements configured to collectively deliver a mist or stream of electrostatically charged treatment solution.

In some examples, the method can include rotating the rotatable needle thereby dissolving a polymer of the treatment solution, and radially spraying, from the distal nozzle tip, the dissolved polymer; subjecting the treatment solution to a relatively high velocity airflow thereby drying the solvent; and then depositing a resultant fibrous mat to the treatment site.

In some examples, the method can include axially positioning the rotatable needle within a needle chamber of the cartridge, the needle chamber comprising a substantially elongate lumen through a central portion of the cartridge between opposing ends thereof.

In some examples, the method can include forming the liquid bandage with electrically spun droplets of the treatment solution.

In some examples, the method can include actuating a power supply of the applicator, by a grip and an activation mechanism of the applicator, the power supply configured to produce a difference of electric potentials on the distal nozzle dip and an auxiliary electrode in electrical communication with the cartridge when the cartridge is disposed in the housing.

In some examples, the applicator can include an applicator housing. A cartridge can be removable and disposed in the housing. The cartridge when arranged in the housing can be in fluid communication with the treatment solution reservoir. The cartridge can include an electrostatic module for electrostatically charging a treatment solution of the applicator and/or the cartridge. The treatment solution is configured to flow through the electrostatic module and toward the nozzle whereby the electrostatic module physically contacts the treatment solution as it flows therethrough and applies an electrical charge to the treatment solution.

In some examples, the treatment solution is stored in a treatment solution reservoir of the applicator.

In some examples, the treatment solution is initially delivered to the cartridge through an aperture of the cartridge.

In some examples, the treatment solution is delivered by a needle through the aperture; and wherein the cartridge is disposable.

In some examples, the aperture comprises one or more caps or valve mechanisms for controlling flow of treatment solution therethrough into the cartridge.

In some examples, the cartridge comprises a cartridge housing and one or more nozzle guides disposed on a lower surface of the cartridge housing, the one or more guides configured to guide and slideably engage the cartridge housing into a locked engagement state with a corresponding guide surface of the nozzle of the applicator.

In some examples, the cartridge comprises a cartridge housing and a release button externally accessible by an end-user, the button configured to extend through a surface of the cartridge and cause the cartridge housing to move between securely locked and unlocked states with the applicator.

In some examples, the cartridge includes a cartridge housing and a first tray disposed in the housing. The first tray can include an array of separation members having openings through which the treatment solution passes while being the electrical charge is applied thereto. The cartridge can also include a piezoelectric element for delivering the electrical charge to the first tray. The cartridge can also include a second tray disposed in the housing underneath the first tray, the second tray comprising an array of separation members having openings through which the treatment solution passes after flowing through the first tray. The second tray can apply heat to the treatment solution as it flows through the separation members after the treatment solution has flowed through the first tray.

In some examples, polymeric material is disposed between separation members of the first and/or second tray for separating cells of the treatment solution as the treatment solution passes through openings of the first and/or second tray.

In some examples, openings on an upper surface of the first and/or second tray are larger than openings on a lower surface of the first and/or second tray.

In some examples, openings of the first and/or second tray are configured to separate cells of the treatment solution prior to being electrostatically charged.

In some examples, openings of the first and/or second tray are conical or tapered.

In some examples, the treatment solution is comprised essentially of stem cells.

In some examples, the treatment solution comprises a mixture that comprises a disinfectant for the treatment site.

In some examples, the treatment solution comprises a mixture that includes at least one of stem cells and a disinfectant for the treatment site. The mixture can include a tracking material for authenticating contents of the treatment solution. The tracking material can be a silica gel capable of being viewed by an optical reader to authenticate contents of the mixture.

In some examples, the treatment site is a wound bed or an open wound.

In some examples, the treatment site is an infection on skin of the patient.

In some examples, the nozzle of the cartridge is a 9-volt piezoelectric nozzle.

In some examples, the nozzle of the cartridge is configured to apply the solution of the applicator uniformly eight to twelve inches in a horizontal orientation.

In some examples, the nozzle of the cartridge is configured to apply the solution of the applicator uniformly eight to twelve inches in a vertical orientation.

In some examples, the applicator applies the solution in discrete particles ranging in 0.05 to 20 micron.

In some examples, the applicator includes a pump disposed inside the applicator housing that propels fluid from the treatment solution reservoir through the cartridge and to the nozzle.

In some examples, the applicator housing comprises a grip and an activation mechanism configured for activating the treatment solution of the applicator to be pumped through the applicator, the cartridge, and out of the nozzle.

In some examples, a canopy is hingedly connected to the applicator housing and hingedly movable between a closed configuration and an open configuration. In the closed configuration, a chamber can be formed between the canopy and the applicator housing for receiving the cartridge. In the open configuration, the canopy can be hingedly moved upward about a shared axis of the applicator housing so the applicator can receive the cartridge.

In some examples, a system is disclosed for applying a treatment solution to a treatment site of a patient. The system comprises any applicator according to this disclosure and a base station capable of receiving the applicator and electrically charging an internal power supply of the applicator.

In some examples, the system includes an optical reader capable of reading and authenticating a tracking material of the treatment solution while the treatment solution is inside the applicator. In some examples, the optical reader is comprised in a mobile device configured to read coded information to verify, identity, or authenticate information related to the treatment solution. In some examples, the base station is configured to inductively charge the internal power supply of the applicator.

In some examples, a system is provided for applying a treatment solution to a treatment site of a patient. The system can include an applicator as described herein and a base station capable of receiving the applicator and electrically charging an internal power supply of the applicator.

In some examples, the system includes an optical reader capable of reading and authenticating a tracking material of the treatment solution while the treatment solution is inside the applicator.

In some examples, the base station is configured to inductively charge the internal power supply of the applicator.

In some examples, a method is disclosed that includes electrostatically charging, by a cartridge assembled with an applicator, a treatment solution for a treatment site of a patient; and uniformly applying, by a nozzle from the applicator, the treatment solution on the treatment site of the patient.

In some examples, the method includes removably assembling the cartridge with the applicator prior to the step of electrostatically charging; discarding the cartridge; removably assembling a second cartridge comprising the treatment solution; and uniformly applying, by the nozzle from the applicator, the treatment solution of the second cartridge on the treatment site of the patient In some examples, the method includes applying the treatment solution within ninety minutes of a wound developing.

In some examples, the method includes mixing stem cells into the treatment solution prior to the step of electrostatically charging.

In some examples, the step of uniformly applying further includes delivering discrete particles of the treatment solution to the treatment site that range between 0.05 and 20 micron.

In some examples, the method includes forming the treatment solution by mixing together at least one of stem cells and/or a disinfectant for the treatment site.

In some examples, the method includes forming the treatment solution with a tracking material mixed with at least one stem cells and/or a disinfectant for the treatment site; and authenticating, with an optical reader external to the applicator, contents of the treatment solution; and if authentic, then carrying out the step of uniformly applying, by the applicator, the treatment solution on the treatment site of the patient.

In some examples, the optical reader is comprised in a mobile device configured to read coded information to verify, identity, or authenticate information related to the treatment solution.

In some examples, the tracking material is a silica gel.

In some examples, the method includes wirelessly connecting the applicator to a mobile device; processing data about current working conditions of the applicator and the cartridge, the current working conditions comprising battery levels, nozzle settings, patient information, end-user information, one or more intended treatment sites dosing, and wherein the data comprises current cumulated record number, battery power settings, treatment solution flow rate, treatment solution levels and treatment solution properties.

In some examples, the method includes controlling, by the mobile device, operation setting and scheduling of the applicator. In some examples, the treatment solution properties comprises a treatment solution type, concentration, medication, and disinfectant.

In some examples, the method includes presenting the processed data in a user interface of the mobile device.

In some examples, the treatment site is a wound bed, an open wound, an infection on skin of the patient.

In some examples, the method includes electrostatically charging the treatment solution by applying an electrical charge to the treatment solution as the treatment solution passes through openings of a first tray of the cartridge; positioning a second tray of the cartridge underneath the first tray; and heating, by the second tray, the electrically charged treatment solution as the treatment solution passes through openings of the second tray.

In some examples, the step of applying the electrical charge to the first tray is from a piezoelectric element of the cartridge.

In some examples, the openings of the first and/or second tray are tapered or conical.

In some examples, use of an applicator is disclosed for producing and applying to a treatment site a treatment solution. The use comprises electrostatically charging, by a cartridge assembled with the applicator, the treatment solution for the treatment site of a patient; and uniformly applying, by a nozzle from the applicator, the treatment solution on the treatment site of the patient.

In some examples, the use comprises removably assembling the cartridge with the applicator prior to the step of electrostatically charging; discarding the cartridge; removably assembling a second cartridge comprising the treatment solution; and uniformly applying, by the nozzle from the applicator, the treatment solution of the second cartridge on the treatment site of the patient.

In some examples, the use comprises applying the treatment solution within ninety minutes of a wound developing.

In some examples, the use comprises mixing stem cells into the treatment solution prior to the step of electrostatically charging.

In some examples, the step of uniformly applying further includes delivering discrete particles of the treatment solution to the treatment site that range between 0.05 and 20 micron.

In some examples, the treatment solution of the use is comprised essentially of stem cells.

In some examples, the use comprises forming the treatment solution by mixing together at least one of stem cells and/or a disinfectant for the treatment site.

In some examples, the use comprises forming the treatment solution with a tracking material mixed with at least one stem cells and/or a disinfectant for the treatment site; authenticating, with an optical reader external to the applicator, contents of the treatment solution; and if authentic, then carrying out the step of uniformly applying, by the applicator, the treatment solution on the treatment site of the patient.

In some examples, the optical reader is comprised in a mobile device configured to read coded information to verify, identity, or authenticate information related to the treatment solution.

In some examples, the tracking material is a silica gel.

In some examples, the use comprises wirelessly connecting the applicator to a mobile device; processing data about current working conditions of the applicator and the cartridge, the current working conditions comprising battery levels, nozzle settings, patient information, end-user information, one or more intended treatment sites dosing, and wherein the data comprises current cumulated record number, battery power settings, treatment solution flow rate, treatment solution levels and treatment solution properties.

In some examples, the use comprises controlling, by the mobile device, operation setting and scheduling of the applicator.

In some examples, the treatment solution properties comprises a treatment solution type, concentration, medication, and disinfectant.

In some examples, the use comprises presenting the processed data in a user interface of the mobile device.

In some examples, the treatment site is a wound bed or an open wound.

In some examples, the treatment site is an infection on skin of the patient.

In some examples, the applicator of the use comprises the an applicator housing; a cartridge removably disposed in the housing, the cartridge when arranged in the housing configured to be in fluid communication with a treatment solution, the cartridge comprising an electrostatic module inside the housing for electrostatically charging the treatment solution; and a nozzle for applying the treatment solution; wherein the treatment solution is configured to flow through the electrostatic module and toward the nozzle whereby the electrostatic module physically contacts the treatment solution as it flows therethrough and electrostatically charges the treatment solution.

In some examples, the use comprises electrostatically charging the treatment solution by applying an electrical charge to the treatment solution as the treatment solution passes through openings of a first tray of the cartridge; positioning a second tray of the cartridge underneath the first tray; and heating, by the second tray, the electrically charged treatment solution as the treatment solution passes through openings of the second tray.

In some examples, the step of applying the electrical charge to the first tray is from a piezoelectric element of the cartridge.

In some examples, openings of the first and/or second tray are tapered or conical.

In some examples, use of an applicator is disclosed for producing and applying to a treatment site a liquid bandage comprising an electrospun fibrous mat, comprising: applying electric potentials to a treatment solution of a cartridge in the applicator for producing the liquid bandage on the treatment site, the applicator comprising an applicator housing; the cartridge removably disposed in the housing and capable of storing a treatment solution with at least one electrospinning medium when arranged in the housing; a rotatable needle with a distal nozzle tip in fluid communication with the cartridge, the distal nozzle tip configured to radially deliver electrically spun droplets of the treatment solution from the applicator to the treatment site; and electrospinning, by the rotatable needle, the treatment solution.

In some examples, the use comprises rotating a proximal end of the rotatable needle, by a motor rotatably connected to the proximal end of the rotatable needle, thereby pressurizing the treatment solution in the cartridge; and driving the treatment solution, by the motor rotating the rotatable needle, out of the distal nozzle tip and creating a fine mist of treatment solution on the treatment site.

In some examples, the use comprises evaporating the treatment solution, by an electrospinning fan of the applicator, from the cartridge through the distal nozzle tip.

In some examples, the use comprises forcing fluids, by an electrospinning fan of the applicator, through a venturi of the distal nozzle tip thereby accelerating flow of fluids to rapidly evaporate a solvent of the treatment solution and then; delivering, by the distal nozzle tip, a fine fibrous mat on the treatment site.

In some examples, the use comprises the rotatable needle comprises an elongate body with an inner lumen; a plurality of radially separated feed tube holes positioned along a length of the elongate body; and a plurality of radially separated distribution elements protruding outwardly from the distal nozzle tip, the distribution elements configured to collectively deliver a mist or stream of electrostatically charged treatment solution.

In some examples, the use comprises rotating the rotatable needle thereby dissolving a polymer of the treatment solution, and radially spraying, from the distal nozzle tip, the dissolved polymer; subjecting the treatment solution to a relatively high velocity airflow thereby drying the solvent; and then depositing a resultant fibrous mat to the treatment site.

In some examples, the use comprises axially positioning the rotatable needle within a needle chamber of the cartridge, the needle chamber comprising a substantially elongate lumen through a central portion of the cartridge between opposing ends thereof.

In some examples, the use comprises forming the liquid bandage with electrically spun droplets of the treatment solution.

In some examples, the use comprises actuating a power supply of the applicator, by a grip and an activation mechanism of the applicator, the power supply configured to produce a difference of electric potentials on the distal nozzle dip and an auxiliary electrode in electrical communication with the cartridge.

In some examples, the electric potential difference ranges between 5 kV to 50 kV.

In some examples, the use comprises the electric potential difference ranges between 20 kV to 30 kV.

In some examples, a use is disclosed that comprises electrostatically charging a treatment solution for a treatment site of a patient; and uniformly applying, by any applicator of this disclosure, the treatment solution on the treatment site of the patient.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 25 depicts an example electrical field at an example wound site of a patient.

FIG. 31 depicts a schematic overview of an example method of this disclosure.

DETAILED DESCRIPTION

Figure 1:
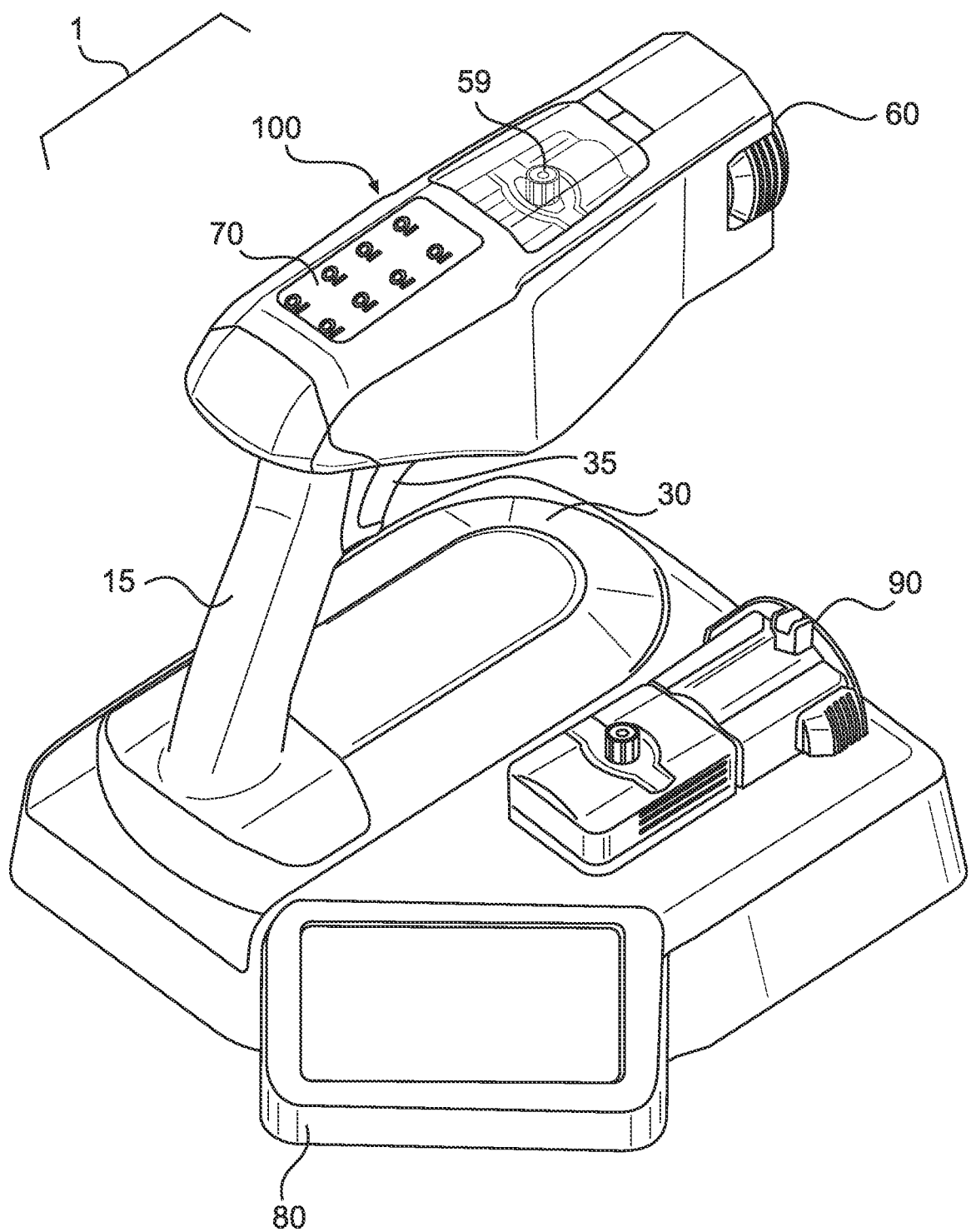
FIG. 1 depicts a perspective view of an example applicator positioned with an example base and cartridge assembly.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be a wound site or treatment of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with application of a treatment solution of a treatment site of a subject.

As discussed herein, "treatment solution" may be a liquid solution that includes stem cells and/or mammalian primary cells, disinfectant, or any other medication that can be delivered to a treatment site for treating a patient. The treatment solution can comprise any concentration or mixture of ingredients, including comprising essentially only stem cells and/or mammalian primary cells, disinfectant, or any other medication as needed or required. The term "treatment solution" can also include one or tracking materials intermixed with the treatment solution.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist.

While prior stem cell applicators can be more effective than grafting for resolving disinfectant and treatment needs of patients; application of stem cells and other solutions can be enhanced dramatically with the use of electrostatic technology as discussed more particularly below. The applicator and related systems and methods of this disclosure enhances application of stem cells to a treatment site of a patient, including skin wound sites such as a wound bed.

It is understood that ionic surfactants are the surface-active agents containing cations or anions as in their formulations. In this respect, the head of the surfactant molecule carries a net electrical charge. It can be either a positive charge or a negative charge. If the charge is positive, it is referred herein as a cationic surfactant. Conversely, if the charge is negative, it is referred herein as an anionic surfactant. Sometimes, these compounds contain a head with two oppositely charged ionic groups referred herein as a zwitterionic surfactant. Anionic surfactants contain negatively charged functional groups in the head of the molecule. Functional groups can include sulfonate, phosphate, sulfate and carboxylates, among others. Cationic surfactants contain positively charged functional groups in the head of the molecule. Most of these surfactants are useful as antimicrobials, antifungal agents, and the like, because they can disrupt the cell membranes of bacteria and viruses. The most common functional group that we can find in these molecules is ammonium ion.

Nonionic surfactants are the surface-active agents that have no net electrical charge in their formulations, meaning, the molecule does not undergo any ionization when dissolved in water. Moreover, nonionic surfactants have covalently bonded oxygen-containing hydrophilic groups that bind with hydrophobic parent structures. These oxygen atoms can cause the hydrogen bonding of the surfactant molecules. Since the hydrogen bonding is affected by temperature, temperature increasing decreases the dissolution of these surfactants. The positive charge has shown to improve the uniformity of coverage of the treatment solution applied from the applicator and the total coverage as to the treatment site. Further, a relatively low level "+" charge has been demonstrated not to alter the intended action of chemical antiseptics and topical anesthetics in the treatment solution of this disclosure.

There are treatment solutions that have proven to gravitate with a negative or positive charge that can alter the chemicals. As discussed more particularly below, the body's cells natural resting state is negative (i.e. a state of negative charge). See, e.g., FIG. 14 of this disclosure. This imbalance is created by potassium and sodium ions inside and outside the cell that establishes electrical capacity in a patient's body. Ionic surfactants are the surface-active agents containing cations or anions as in their formulations. There, the head of the surfactant molecule carries a net electrical charge. It can be either a positive charge or a negative charge. It is understood that there are chemicals that need a negative charge or a neutral charge. In some examples, the applicator and related systems of this disclosure can be configured to switch polarity at a touch of your finger (e.g., through an actuator, switch, digital indicator and the like)

In some examples, this disclosure utilizes the foregoing by positively charging its treatment solution and then delivering positively charged molecules of the treatment solution from its applicator to a treatment site in order to achieve electron balance. In achieving this balance, the treatment solution uniformly applies to a treatment site since the positively charged molecules of the treatment solution seek balance by uniform application across the negatively charged treatment site. In some embodiments, the treatment solution can be positively charged by delivering electrostatic charges across the treatment solution of the applicator and through corresponding conical array of its cartridge that uses a positive or negative charge to stem-cells and antiseptics using an electrostatic module. In particular, the applicator and related systems of this disclosure can be configured to apply a ("+") ("–") or (neutral) charge to the treatment solution and a "–" to the treatment site (e.g., the intended target). In some examples, the applicator can also go to a neutral state by shutting it off. However, it is also contemplated that this can be reversed and that a positive electrostatic charge can be applied with the applicator as needed or required, since certain chemicals in a treatment solution may need a negative charge rather than a positive charge.

One example of an applicator of this disclosure that positively charges the treatment solution can be one that positively charges a treatment solution and then applies the electrically charged treatment solution, such as a solution that includes stem cells, onto a treatment site. In one example, the applicator includes an electrostatic delivery system, whereby the treatment solution passes through electrodes of a cartridge that is positioned with the applicator. Charged particles of the applicator can then be applied from a nozzle of the applicator to a patient's treatment site (e.g., a negatively charged treatment site) where the charged particles of the treatment solution are induced thereon to form an electric field charge within a mist of the solution being applied.

Turning to the drawings, FIGS. 1-2B show forward and rear perspective views, respectively, of an electrostatic treatment solution applicator 100 that is configured to electrically charge, atomize, and apply a treatment solution to a treatment site of a patient. The applicator 100 can include an applicator housing 10 that includes a grip 15 configured to be held by a user. Grip 15 of applicator housing 10 can include an ergonomic shape holdable by the user though the exact size and shape of the applicator housing 10, and any constituent features, can vary. A canopy 20 can be pivotably connected to an upper surface of the applicator housing 10 to form a cartridge receiving chamber 25. A cartridge 50 can be removably inserted into the cartridge receiving chamber 25 when the canopy 20 is moved about a shared axis of the applicator housing 10 to an open configuration. In some embodiments, canopy 20 can be partially or completely transparent, or include some portions that are transparent to the extent an optical reader can scan and identify treatment solution contained in cartridge 50, as discussed more particularly below. Conversely, in a closed configuration, the canopy 20 can be sealed or in substantial contact along its perimetral edge with corresponding surfaces of the applicator housing 10 to close the cartridge receiving chamber 25. Extended from the grip 15 can be one or more base sections 30 for positioning on a planar surface between uses. Sections 30 can be configured for positioning on or within a base 80, as in FIG. 1. Also, FIG. 1 depicts an example optical reader 90 for authenticating contents of the treatment solution of cartridge 50, as discussed more particularly below.

Applicator 100 can have actuator 35 for activating or deactivating applicator 100, including powering on the system power, activating an onboard pump P, applying an electrostatic charge to treatment solution, and delivering treatment solution from a cartridge 50 through nozzle 60 and onto a treatment site. Housing 10 can also include a display 70 positioned on an outer surface of applicator 10 and capable of providing output indications to the end user, including data related to onboard power, pump settings, treatment solution settings, etc. Applicator 100 can include a treatment delivery region proximate or adjacent nozzle 60 towards a forward end of the applicator housing 10, said region having an opening through which nozzle 60 and corresponding atomized treatment solution can be expelled. Applicator housing 10 can also include an onboard tank internally therein for housing treatment solution. In some embodiments, the tank can also be removably attached as needed or required.

Figure 2A:
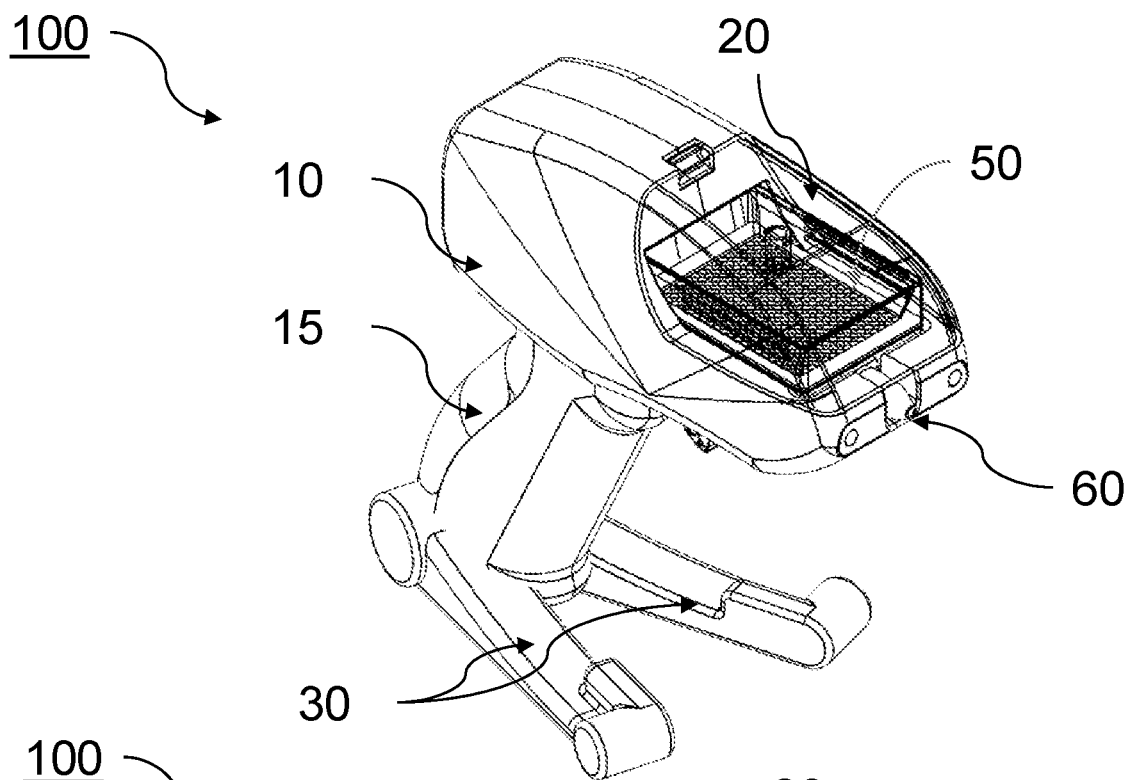
FIG. 2A depicts a perspective view of an example applicator.
Figure 2B:
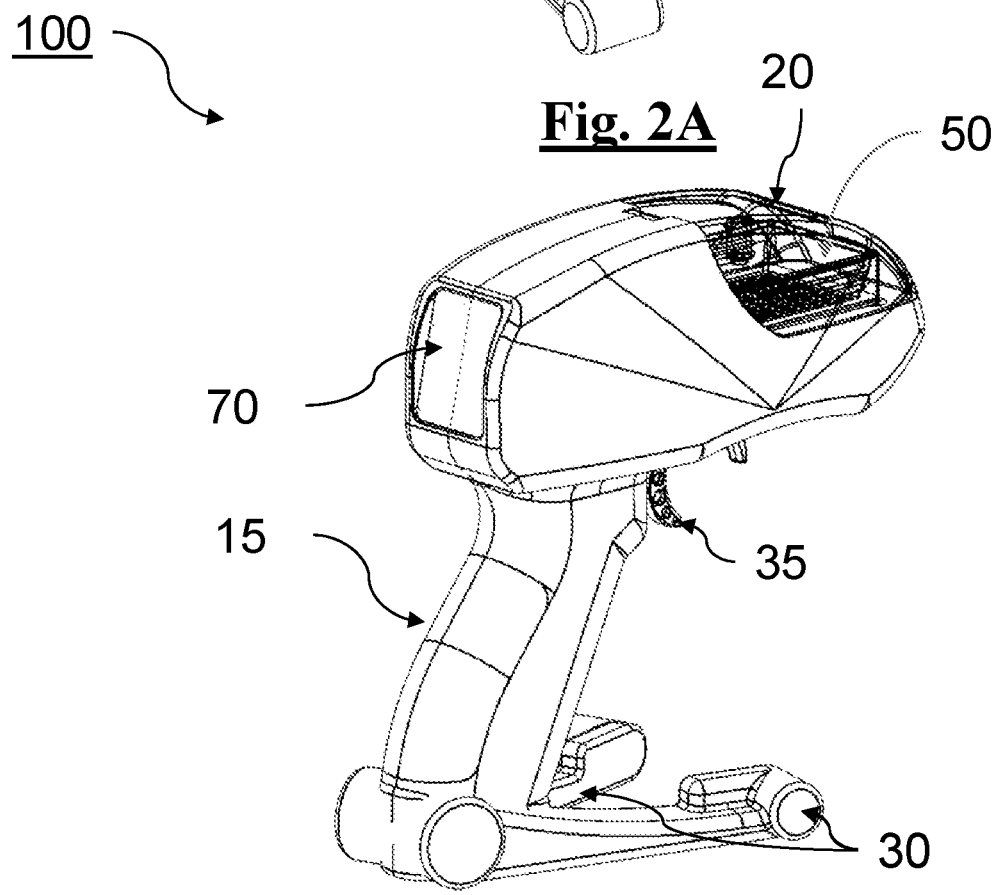
FIG. 2B depicts a perspective view of an example applicator.

Applicator as shown in FIGS. 1-2B can also include the cartridge 50, including nozzle 60, capable of heating, applying an electrostatic charge, and delivering treatment solution to a treatment site, as discussed more particularly below. Chamber 25 that receives cartridge 50 and be capable of fluidly communicating with nozzle 60 for supplying treatment solution that can be electrically charged and atomized by the nozzle 60.

Figure 3:
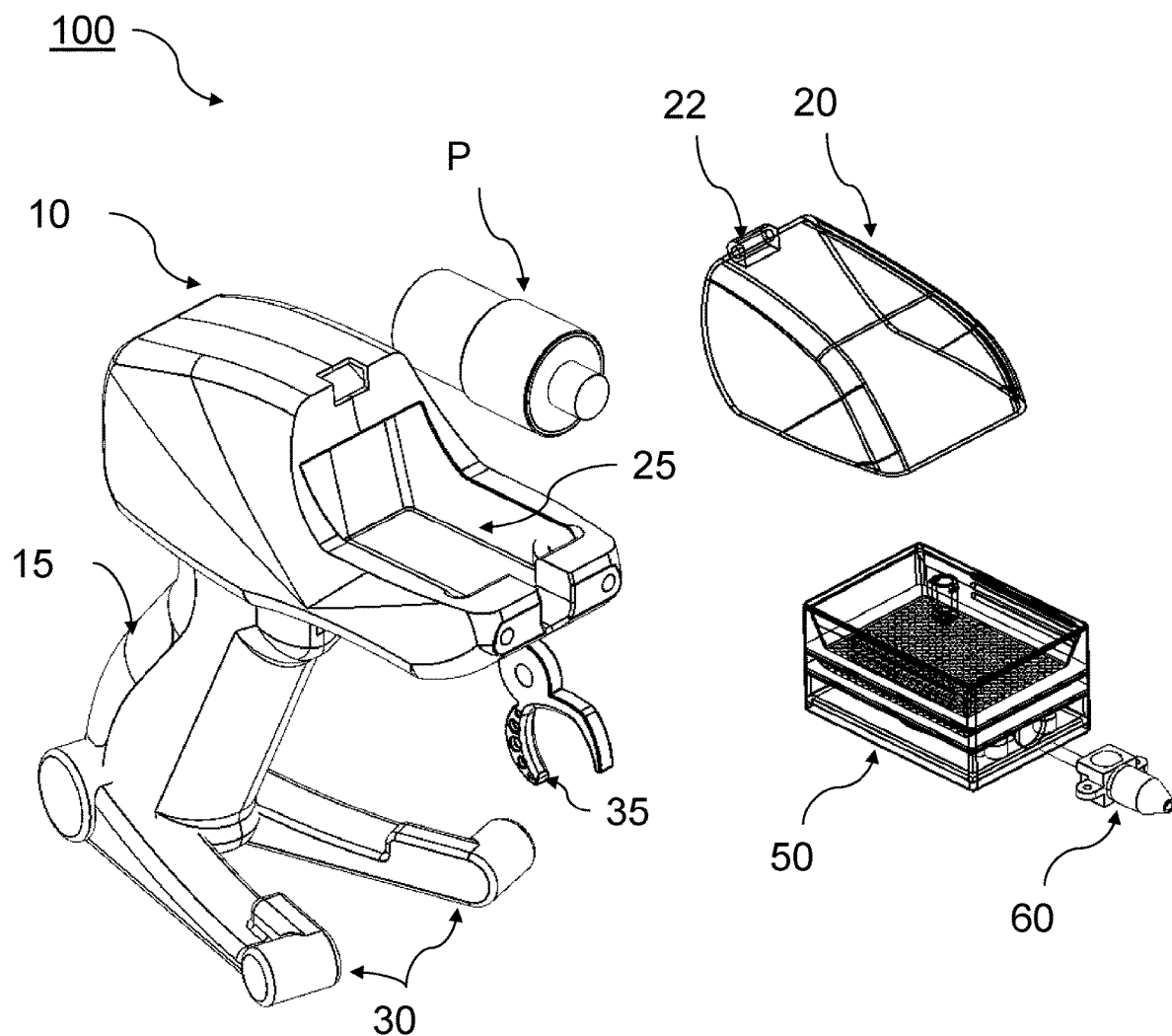
FIG. 3 depicts a perspective view of the example applicator of FIGS. 1-2B in an exploded state.

FIG. 3 shows the applicator 100 in an exploded state. The housing 10 of applicator 100 can be formed of a single unitary piece or multiple discrete pieces that connect to form an inner volume for housing features of applicator 100. Applicator 100 can include a pump P as well as an internal power supply, including one or more batteries B, such as a lithium ion battery. An electrical circuit board of applicator 100 can be configured to convert DC to AC power for powering the pump P as well as other features of applicator 100. The applicator 100 may also include a protection circuit module (PCM).

Figure 4:
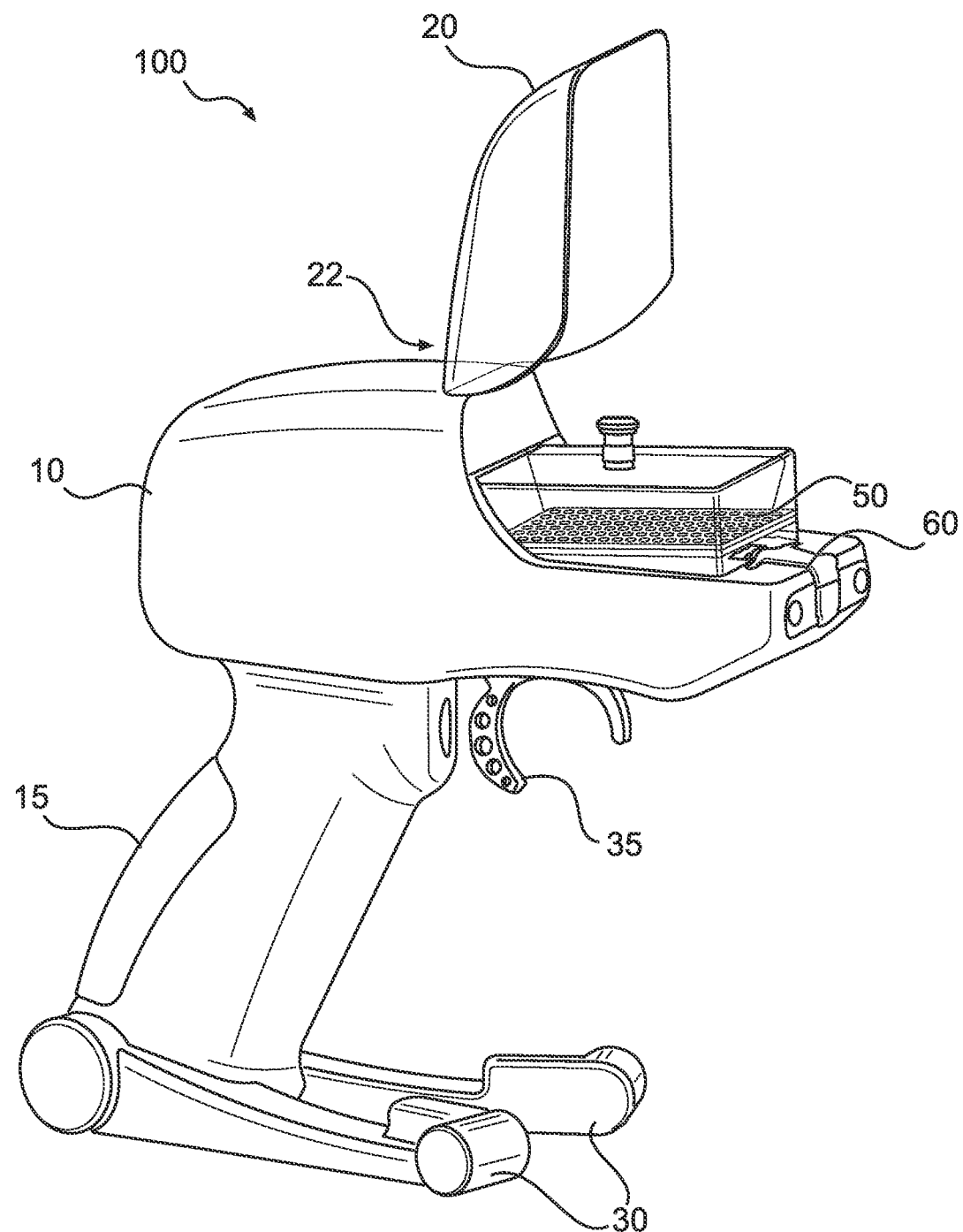
FIG. 4 depicts a perspective view of the example applicator with its canopy in an opened state showing the cartridge in an assembled state.

Turning to FIG. 4, a perspective view of applicator 100 is provided in an opened state showing the cartridge 50 in an assembled state within chamber 25 of applicator 100. Cartridge 50 can be loaded into chamber 25 of applicator 100 while canopy 20 is in an opened configuration. In this opened configuration, cartridge 50 can also include treatment solution (or treatment solution can be later added to cartridge 50). Once inside cartridge 50, treatment solution can be authenticated by an optical reader (e.g., a mobile device with an optical reader) for purposes of verifying that the intended treatment solution is in fact the solution being delivered to the correct patient, as well as prevent counterfeit treatment solution). In some examples, the optical reader can view tracking material inside the treatment solution (e.g., silica tracking gel particles).

Applicator 100 and related systems 1 also contemplate using a tracking system with respect to the treatment solution both to conserve resources attributed to the treatment solution as well as the patient safety. In particular, in recent years problems have arisen with respect to counterfeit treatments and ensuring that patients are receiving the treatment required for their conditions, since present technology fails to adequately provide a way to effectively verify whether a particular treatment is in fact the treatment prescribed for a patient.

To resolve these and other problems, a treatment verification system can be included in certain embodiments of the applicator of this disclosure. The treatment verification system in some examples can include silica barcoding, whereby the silica range can be from 5.0-20 microns. The silica barcoding can be mixed with the treatment solution and thus be coded for a particular treatment or patient then prior to application can be used to authenticate. In turn, the chain from manufacturer to medical users can be more secure as well as ensuring patient safety optimized to the extent possible.

In some examples, the treatment verification system with silica has no increased cytoxicity found with Silica nanoparticles being in the same medium as stem cells.

Further, in some examples, the cartridge 50, including the cartridge housing 52, can have barcode information to further track and authenticate information related to the applicator 100, treatment solution, and/or the patient. In some examples, when the cartridge 50 is inserted into or operatively coupled with an optic reader prior to use, identifying data imprinted on silicone can be used to identify certified stem cells or other information of the treatment solution. The optic reader, which can be a mobile device, can read coded information to verify, identity, or authenticate information related to the treatment solution. In some examples, the optic reader can be aligned with and read by one or more LEDs of the system.

Figure 5A:
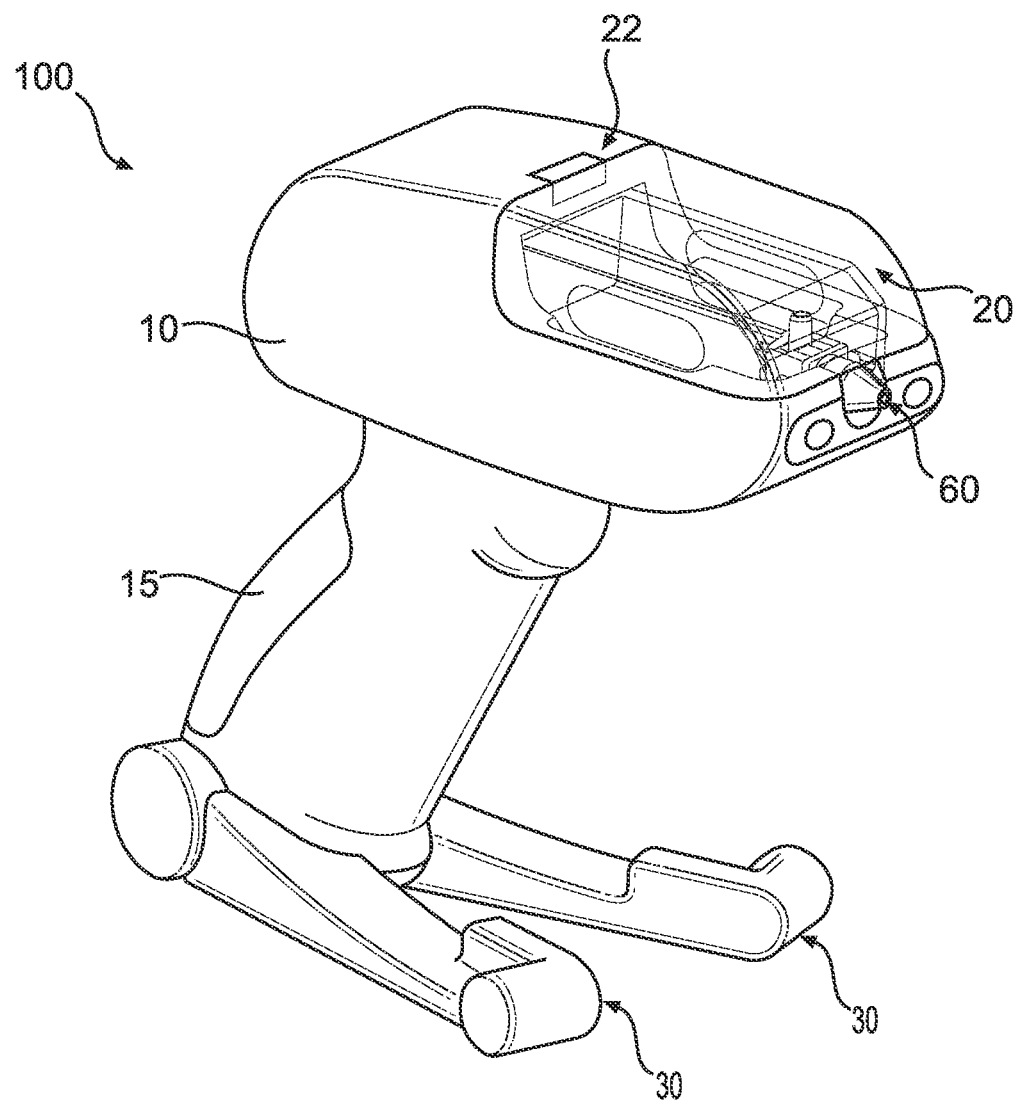
FIG. 5A depicts a perspective view of the example applicator with its canopy in a closed state.
Figure 5B:
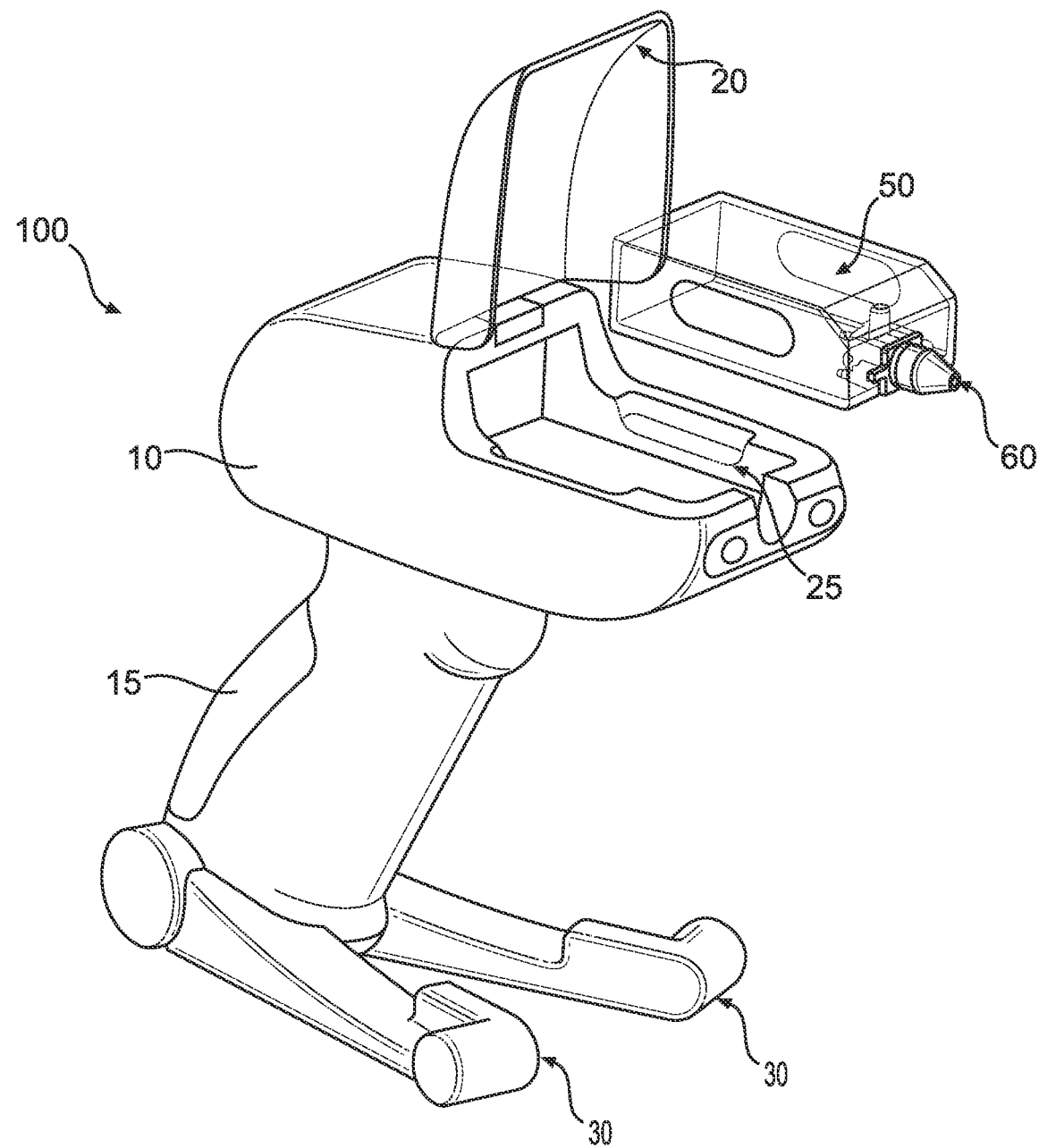
FIG. 5B depicts a perspective view of the example applicator with its canopy in an opened state showing the cartridge in prior to being assembled in the cartridge receiving chamber of the applicator.

Turning to FIG. 5A, a perspective view of applicator 100 is provided in an opened state showing the canopy 20 of applicator 100 in a closed state. In contrast, FIG. 5B depicts canopy 20 having been pivoted about a shared axis 20 with applicator 100 so that canopy is now in the opened configuration. Once opened, cartridge 50 can be delivered to chamber 25 and assembled therewith, including nozzle 60 with respect to the forward nozzle region of applicator 100.

Cartridge 50 can be loaded into chamber 25 of applicator 100 while canopy 20 is in an opened configuration. In this opened configuration, cartridge 50 can also include treatment solution (or treatment solution can be later added to cartridge 50). Once inside cartridge 50, treatment solution can be authenticated by an optical reader (e.g., a mobile device with an optical reader) for purposes of verifying that the intended treatment solution is in fact the solution being delivered to the correct patient, as well as prevent counterfeit treatment solution). It is also contemplated that other information from cartridge 50 can be detected as well, including remaining volume of a treatment solution, amount applied since last detected or checked and when that solution was applied, the patient and corresponding intended treatment site of the patient, and the like. In some examples, the optical reader can view tracking material inside the treatment solution (e.g., silica tracking gel particles).

Figure 6:
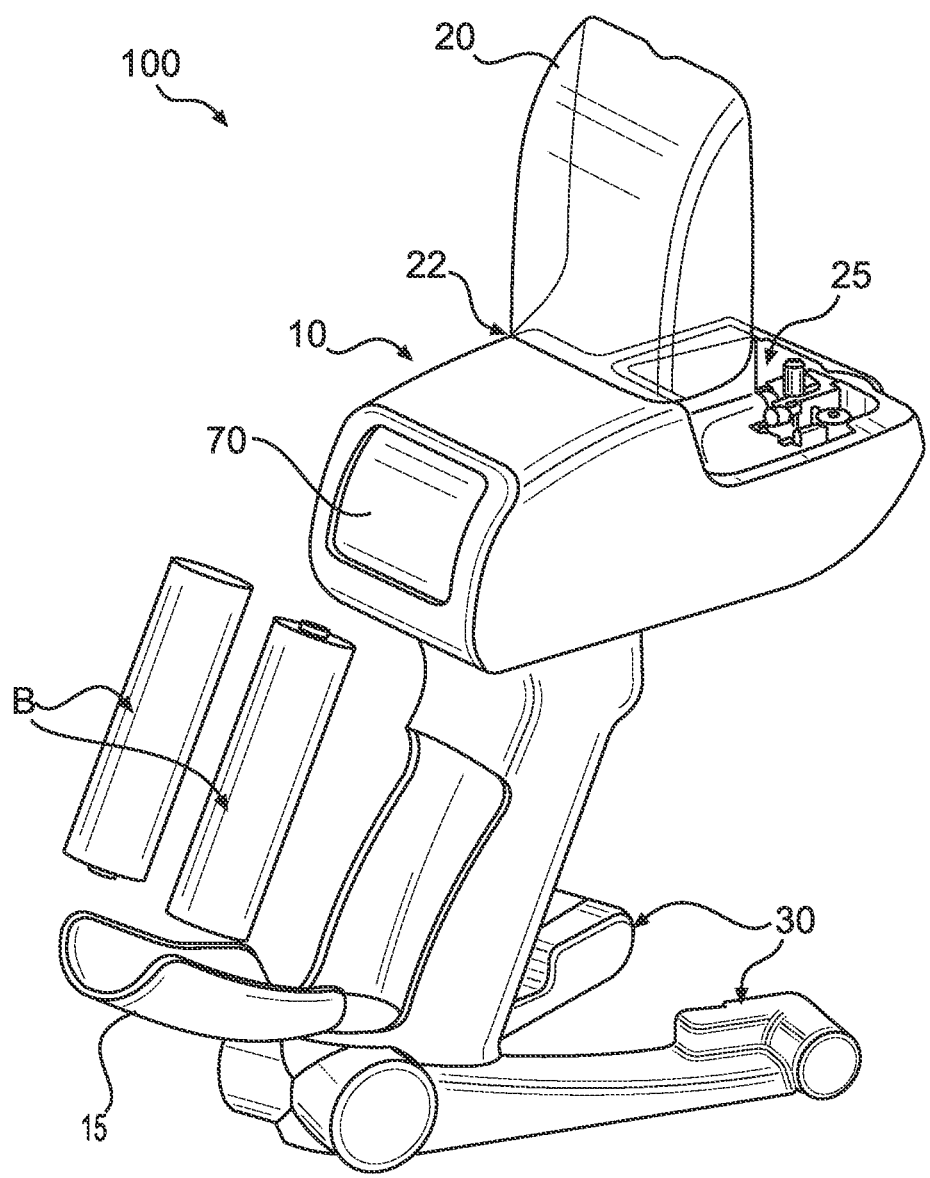
FIG. 6 depicts a perspective view of the example applicator with its canopy in an opened state and internal power supply in an exploded state.

Turning to FIG. 6, grip 15 can be seen having been removed to reveal a battery chamber that contains internal power supply of applicator, one or more batteries B. Otherwise, canopy 20 can be viewed in FIG. 6 similarly in an opened configuration with chamber 25 capable of receiving cartridge 50 therein.

Figure 7A:
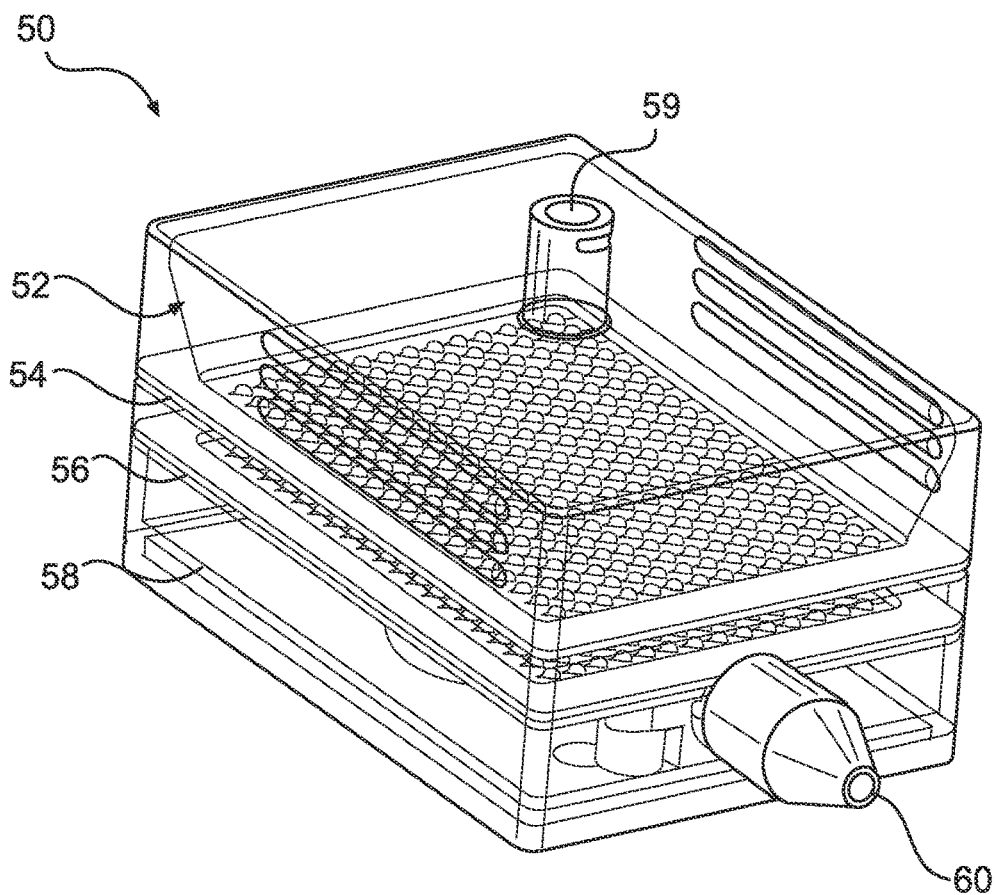
FIG. 7A depicts a perspective view of an example cartridge.
Figure 7B:
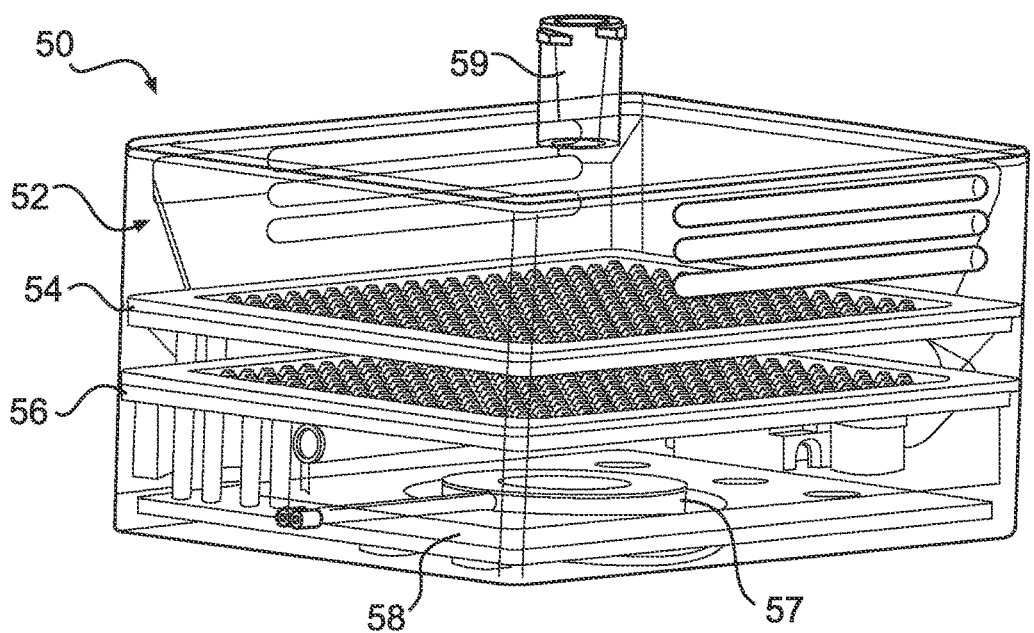
FIG. 7B depicts a perspective view of an example cartridge.
Figure 8:
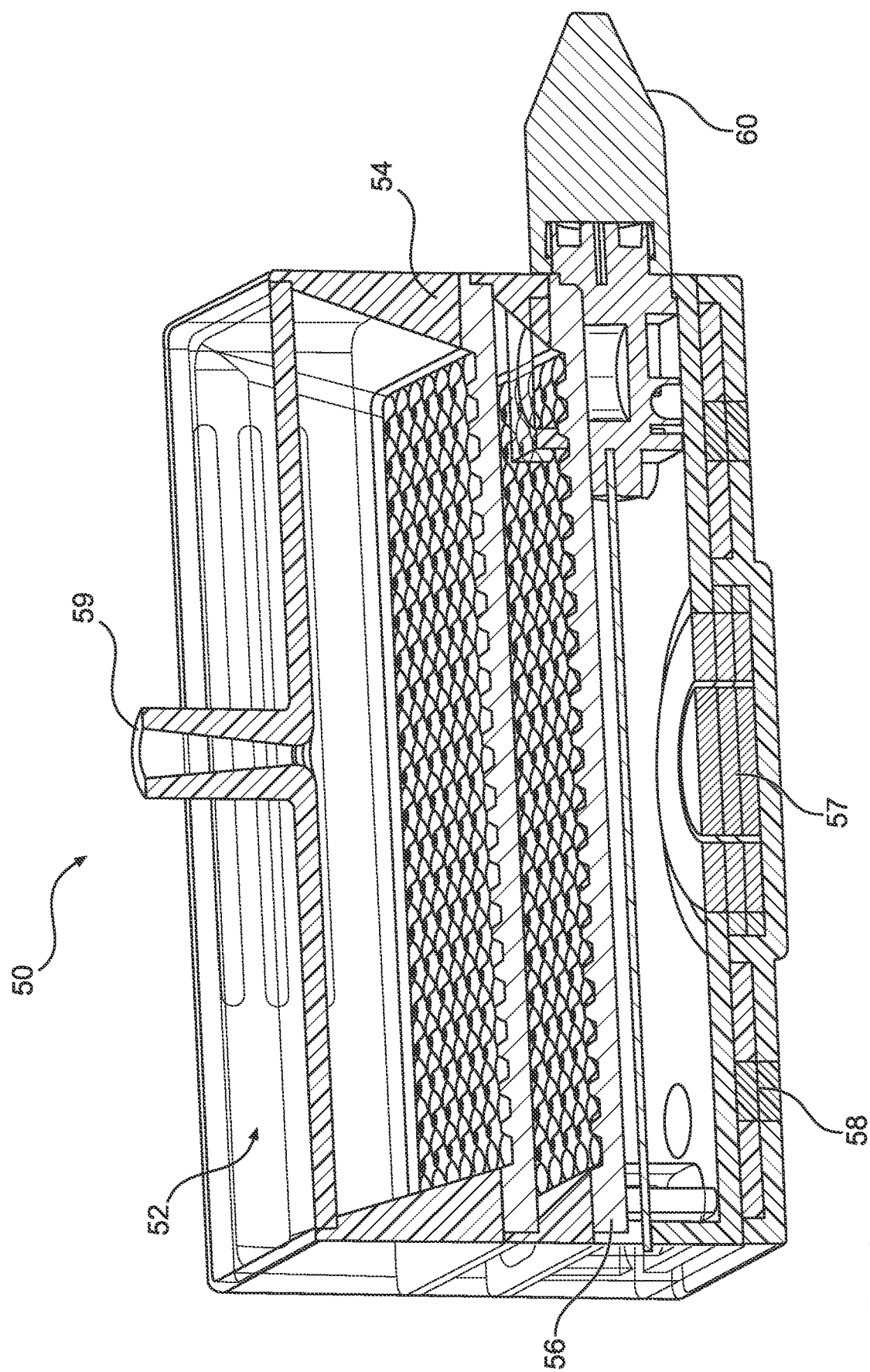
FIG. 8 depicts a perspective view of a cross section taken along horizontal center line of an example cartridge.
Figure 9:
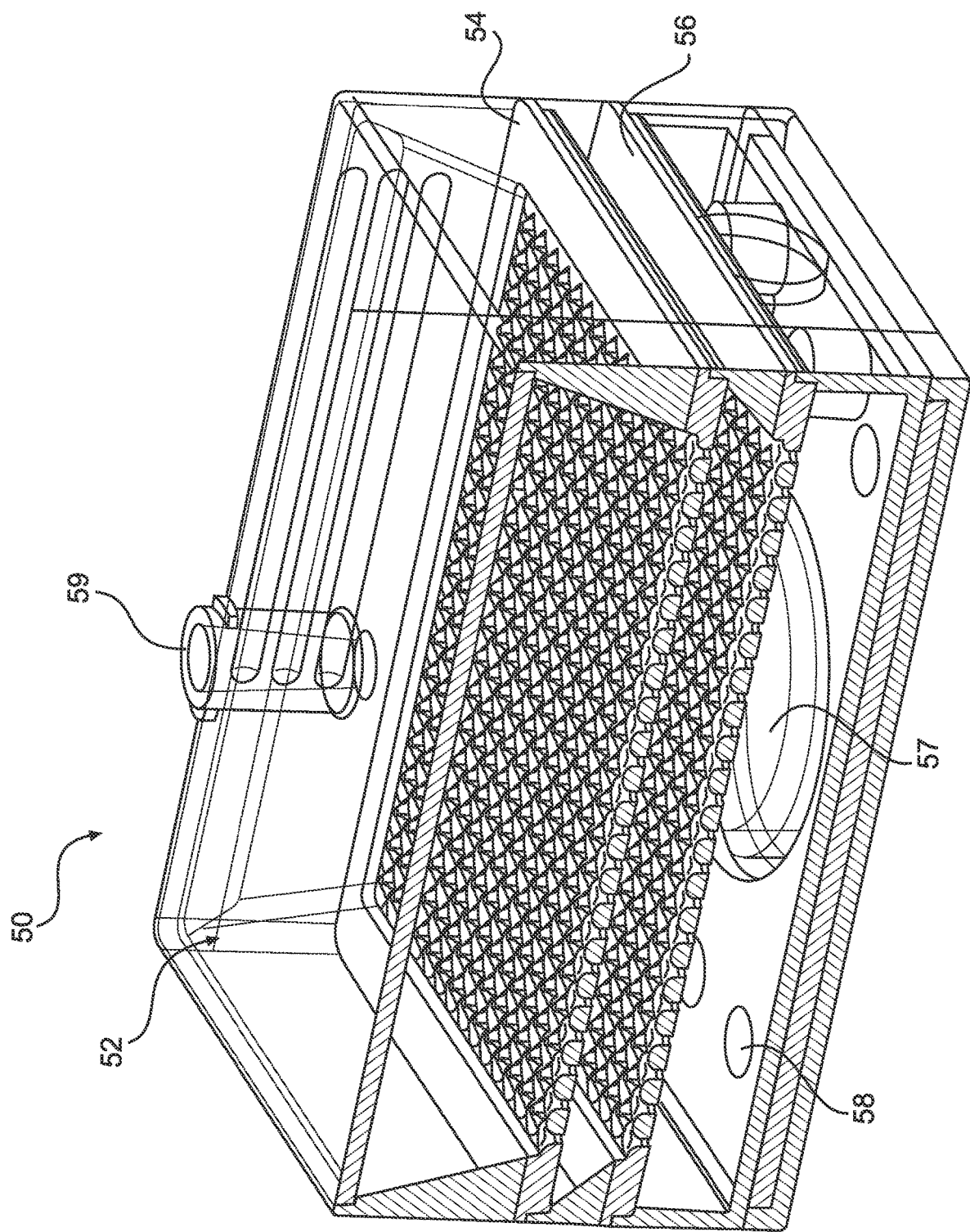
FIG. 9 depicts a perspective view of a cross section taken along another horizontal center line of an example cartridge.
Figure 10:
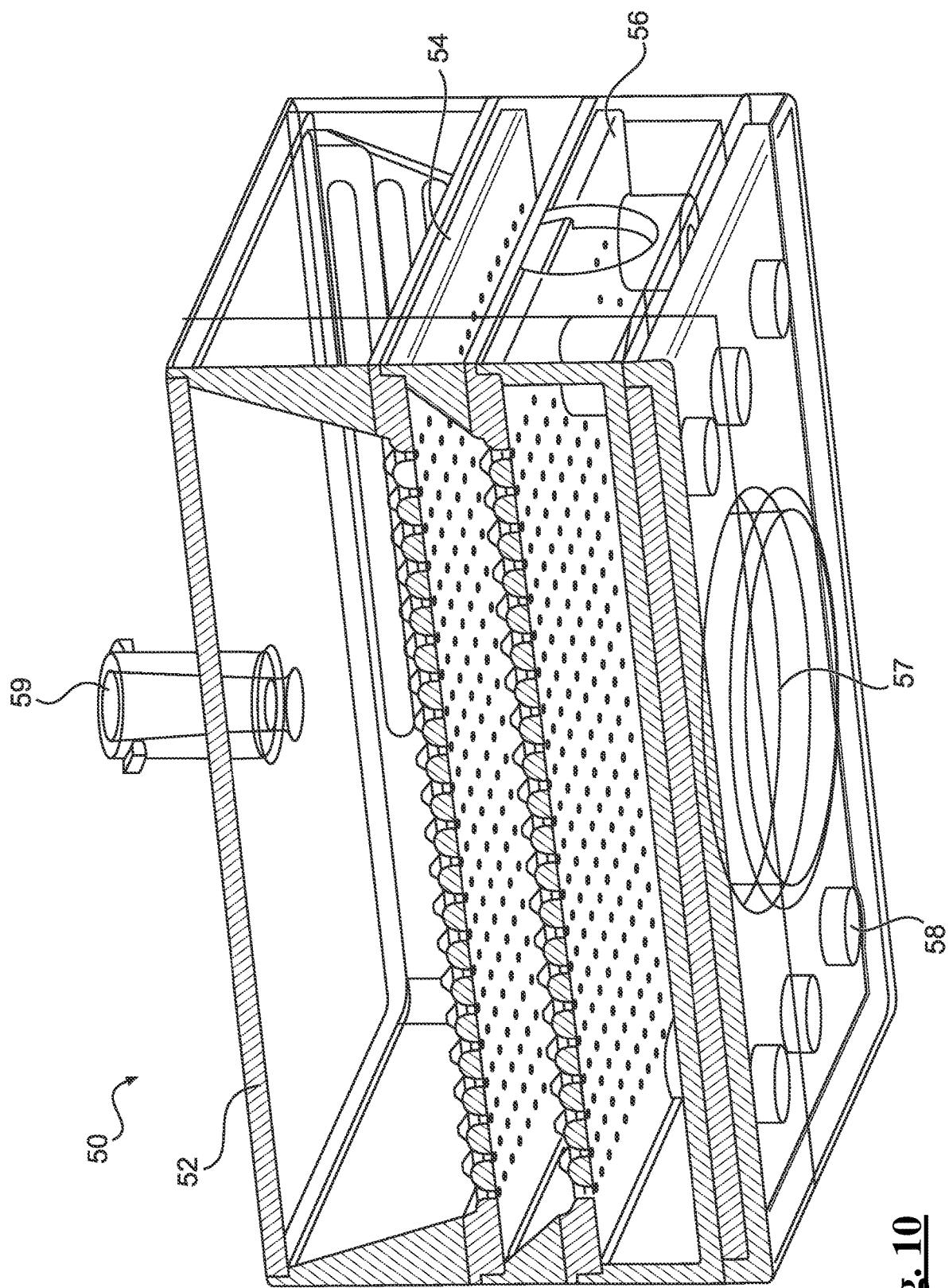
FIG. 10 depicts a perspective view of a cross section taken along another horizontal center line of an example cartridge.
Figure 11:
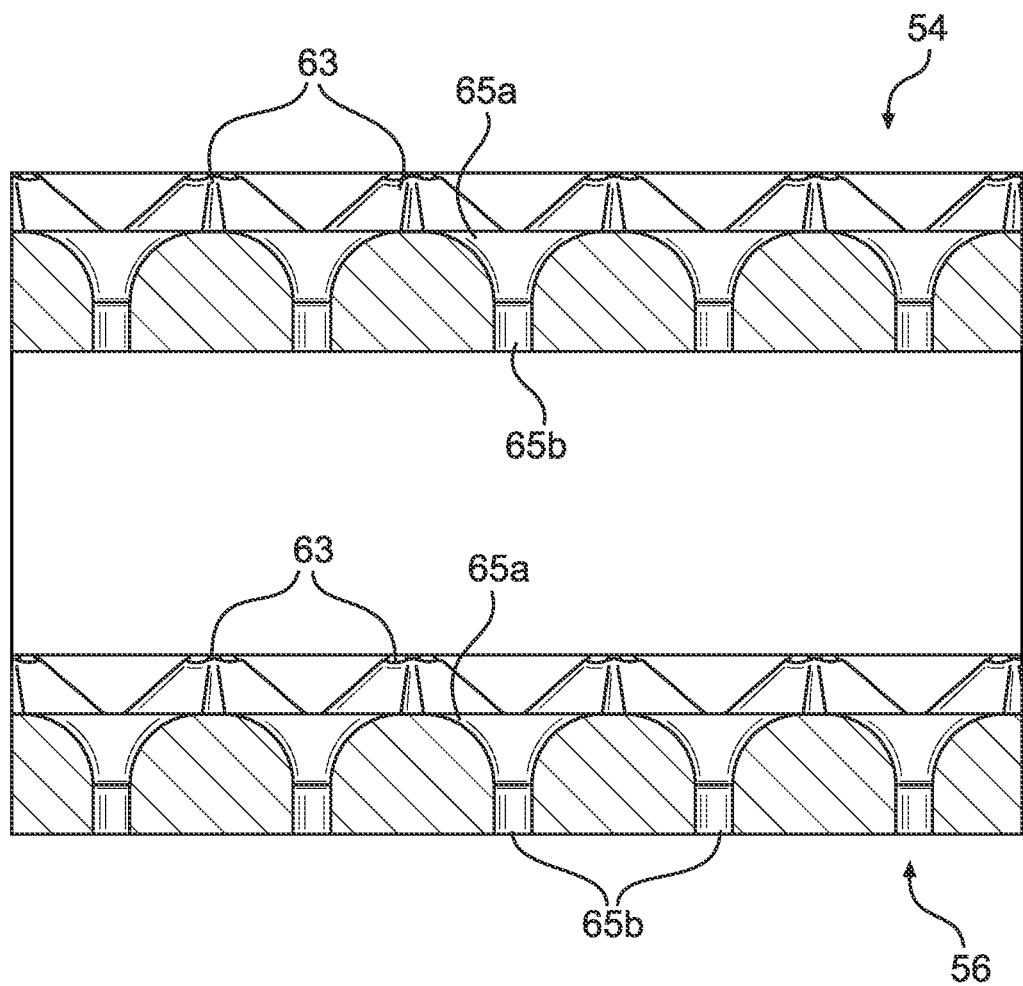
FIG. 11 depicts a close-up side plan view of a cross section of example trays of an example cartridge of this disclosure.

Turning to FIGS. 7A and 7B, a close-up perspective view of example cartridge 50 is shown. In one example, cartridge 50 can have a housing 52 that is rectangular (though other shapes are contemplated as needed or required). Housing 52 can be made from polycarbonate, medical grade plastic and can be disposable. In some examples, cartridge 50 can be disposable whereas in other examples certain features of cartridge 50 (e.g., the piezoelectric system) while other example features are separately disposable (e.g., housing 52). FIGS. 8, 9, and 10 depict similar perspective cross section views of cartridge taken along different horizontal center lines a cartridge 50, further depicting how features of cartridge 50 are oriented and assembled together. Cartridge 50 can be configured to positively charge the treatment solution for application from the applicator 100. In turn, the positively charged treatment solution can seek balance in a negative ground that is provided by the negatively charged treatment site of the patient. This is particularly advantageous for providing superior coverage by the treatment solution to the treatment site since the particles of the cartridge 50 will not be stacked when the nozzle 60 applies the positively charged particles since each particle that as a positive charge and thus will not land on itself.

An aperture 59 can be provided on an upper surface of the housing for receiving treatment solution (e.g., a needle can deliver the solution therethrough). In some examples, aperture 59 can include on or more caps or valve mechanisms for controlling flow of treatment solution therethrough. In some examples, the treatment solution can include autologous and/or allogenic stem cells that are trackable for purposes of authenticating the treatment solution prior to use. In some examples, the treatment solution can be tracked to its original source by including silica nanoparticles in the treatment solution that are placed on the cells once they are harvested and cryo-preserved.

In some examples, cryopreservation is a process that preserves cells, organelles, tissues, and any other biological constructs by cooling the treatment solution to very low temperatures. Stem cells and other viable tissues cannot be stored with simple cooling or freezing for a long time because ice crystal formation, osmotic shock, and membrane damage during freezing and thawing can cause cell death. There has been an increase in successful cryopreservation in the last decade with the use of cryoprotective agents (CPA) and temperature control equipment.

One example method is contemplated for use with the treatment solution of this disclosure includes a vitrification method that involves a cryoprotective agent used in the fast cooling of cellular material. The vitrification method used with the applicator and treatment solution of this disclosure is fast, inexpensive, and has been used for the cryogenic storage of sperm, human embryo, and oocytes for applications in IVF.

Another example method is a slow cooling method which allows cooling at a rate of approximately about 1° C./min in the presence of less than 1M (molar) of cryoprotective agent (CPA). Cryogenic formulations contemplated for use can include 50% FBS (fetal bovine serum) 40% Media, 10% DMSO (Dimethyl Sulfoxide) or 90% FBS; 10% DMSO.

In some examples, thawing of cellular material of the treatment solution can involve the following steps once the cryogenically preserved cells are ready for application: (1) Solutions are warmed to recommended temperature of 37° C. in water bath; (2) Wipe down cryogenic tube with 70% ethanol or isopropanol; (3) The tube can be taken to a biosafety hood in order to open the tube in order to relieve the pressure, and then retighten the tube; (4) Quickly thaw vial of frozen cells in a 37° C. water bath for no more than 2 minutes; (5) Wipe down the tube with 70% ethanol and transfer back to biosafety hood; (6) Aseptically transfer the contents of the tube to a conical tube that contains pre-warmed media/solution; (7) Centrifuge the cell suspension in tabletop centrifuge at 300×g at RT for approximately about 10 minutes (though other parameters are contemplated such as 1000 RPM at RT for 5 minutes); (8) Aspirate the solution in the biosafety hood being careful not to disturb the pellet; (9) Resuspend the pellet by gently flicking the tube with pre-warmed media/solution; and/or (10) Add the appropriate amount of desired media/solution and you can perform a cell count again to add the needed volume in order to obtain the desired cell concentration. Carrying one or more of the foregoing thawing steps results in a relatively small loss of cells, including during the washing steps, but needed as to remove the CPA that may be harmful to the stem cells. Regardless, the cells are now ready to load on the applicator for delivery.

Once they are verified (e.g., by an optical reader, the base of the system associated therewith upon reading information from an operatively loaded cartridge, etc.), the treatment solution, including its autologous and/or allogenic stem cell suspension, can be aseptically loaded into the cartridge housing 52 via aperture 59. After being introduced therein, the treatment solution (including autologous/allogenic stem cell suspension solution) can be passed through cell pores of a first tray 54 found in its heating surface to a hydrostatic chamber of a second tray 56 at its cell pores where a positive charge is delivered. The treatment solution can then be delivered to the desired treatment site from cartridge 50 through nozzle 60 using a piezoelectric nozzle that evenly and/or uniformly distributes the treatment solution to a treatment site (e.g., a wound bed).

It is understood that the stem cell suspension can be maintained at a physiological temperature with second tray 56 (e.g., a thermal plate) in the cartridge 50. In turn, cartridge 50 can optimize and increase viability of stem cells and any other biological matter of the treatment solution for delivery by keeping the temperature at a physiological level. Cartridge 50 can eject high voltage ions to through high voltage ion discharge cells of tray 56. Cells of tray 56 will be described in more detail herein but can be seen as being selectively positioned on tray 56 to receive treatment solution previously heated from treatment solution similarly flowing through cells of tray 54. Once heated and charged, droplets of the treatment solution can be applied to the treatment site from nozzle 60. In some examples, pump P can be in fluid communication with cartridge 50 when cartridge is assembled with chamber 25 of applicator 100. Cartridge 50 can include an electrostatic module that is electrically connected to and configured to electrostatically charge tray 56 and/or tray 54 through its cells. However, the solution of this disclosure is not so limited and instead of applying a charge to the treatment solution through open cells of a respective tray, instead the respective tray can include one or more electrodes, rings, and/or tubes for electrostatically charging the treatment solution prior to application on the treatment site.

A piezoelectric element 57 can also be positioned on a tray 58 underneath tray 56, whereby the piezoelectric element 57 is configured for positively charging the treatment solution. It is understood that the piezoelectric effect is the ability of certain materials to generate an electric charge in response to applied mechanical stress. In some examples, when the treatment solution is applied by applicator 100, the charged solution is forced out through the piezo nozzle and broken up into tiny charged droplets in the air. Since all the droplets are carrying the same charge, they will repel each other forming a uniform fine mist in the air. With the help of electrical attraction force between the mist and the intended object, they are pulled like a "magnet" towards the intended object on which opposite charge is induced to its surface via the ground. Since our sprayer can create very fine lightweight charged droplets, the fine droplets will spread with high mobility and therefore can reach the edges and even backside of the intended object and in some cases achieve the desired 360 degree coverage, which is sometimes referred to as an electrostatic "wrap around effect". When being applied within the electrostatic field caused by the cartridge 50, the treatment solution can wrap 360 degrees around the opposite field charge, which in this case is the negatively charged treatment site. Element 57 can be a battery-powered piezoelectric atomizing element positionable downstream from pump P and in the flow path of treatment solution with respect to trays 54, 56. Element 57 can be driven such that it vibrates, typically at ultrasonic frequencies, in a manner that atomizes the treatment solution.

One of the unique characteristics of the piezoelectric effect of the solution described herein is that it is reversible. In other words, although it is contemplated that the treatment solution is positively charged so that it can be applied to a negatively charged treatment site, the converse is also contemplated, since materials exhibiting the direct piezoelectric effect (the generation of electricity when stress is applied) also exhibit the converse piezoelectric effect (the generation of stress when an electric field is applied).

Nozzle 60 of cartridge 50 can be a nozzle assembly configured to apply the atomized treatment solution to the treatment site. In one example, pump P is used to deliver air pressure to the nozzle tip of nozzle 60. Pump P can be a piston pump, a pneumatics micro pump acting with a solenoid, a pump that pulls a vacuum in applicator to cause fluid to flow out of the reservoir toward the nozzle 60, or the like. Nozzle 60 can include an elongate tubular member with an inner lumen with a tip terminating in a conical, tapered, frustoconical or any other countered or shaped surface that can be curved or straight. The surface is shaped such that fluid from the nozzle 60 is configured to apply atomized droplets of treatment solution in the range of 5 microns to 40 microns in size. The nozzle 60 can be mechanically coupled to cartridge 50.

The nozzle 60 in particular of certain example nozzles of this disclosure is advantageous since the nozzle 60 applies the treatment solution to the treatment site with minimal forces, including shear force and pressure on the cell membrane of the treatment solution, rather than if the treatment solution were delivered by some of other means such as an injectable syringe. Injection delivery of stem cells is known to suffer from cell viability post application, whereas the nozzle 60 of this disclosure resolves these and other problems since nozzle 60's applying stem cells in the treatment solution avoids the shear forces and pressure from prior injectable approaches. The nozzle 60 is also advantageous since operative application of the treatment solution can occur without the need for any gas pressure (e.g., oxygen cylinders) or pneumatic pumps to drive the nozzle. In some examples, the nozzle 60 can deliver particles ranging approximately 1-7 microns. The frequency and the oscillation frequency of the nozzle 60 in some examples can be adjusted to increase larger molecules by adding a series of parameters that are built within a power circuit board (PCB) and the piezoelectric element 57.

In some examples, as more clearly seen in FIG. 11, the cartridge 50 can include a micro bubble of polymeric material 63 between each separation member 65 which is advantageous since this prevents cells of the treatment solution from simply sitting on top of the trays 54, 56 within the cartridge housing 52. In turn, stem cell walls of the treatment solution are preserved while each enter respective separation members 65, rather than being potentially wasted by harming said stem cell walls.

In some examples, the applicator 100 and corresponding features can include an internal power supply, such as previously described battery B that is replaceable and/or rechargeable. The one or more batteries B can include including lithium-ion (Li-ion) batteries that contain a carbon anode, a cathode made of lithium cobalt dioxide and an electrolyte containing a lithium salt in an organic solvent: In certain examples, a Li-ion battery of 3400 mAh can be used having a run time of 40 hours to the applicator 100 before charging. In this example, a 9V Piezoelectric can draw from the 9V power supply thereby keeping the piezo 57 stable. Other example batteries are also contemplated. In other examples, the applicator 100 and corresponding features can be in electrical communication with an external power supply, such as a wall power.

Although applicator 100 can be powered by battery B, it can still apply electrical charges to the aqueous treatment solution by an electrostatic module inside the applicator 100 for an electrically balanced system, opposite charge has to be supplied to compensate the charge spent to the liquid treatment solution. This is effectively achieved by a ground plate on the handle grip; opposite charge can flow through the ground plate from user to electrostatic module to counterbalance the charge lost to the liquid treatment solution.

As also seen in FIG. 11, a close-up side plan view is shown of a cross section of trays 54, 56 of cartridge 50. During use, electrostatic charges can be applied across treatment solution and through the cells 65 of tray 56 (and/or tray 54). As can be seen, cells 65 can be oriented substantially conical or tapered with a larger opening **65*a* where the treatment solution is received and an opening 65*b* with a smaller diameter than opening 65*a*. Each cell 65 can be a contoured, three-dimensional geometric shape that tapers smoothly from a flat base from the tray upper surface to a point called apex or vertex at smaller opening 65*b*. Cells 65 can be selectively positioned and spaced so that cells of the treatment solution avoid stacking when entering into each cell 65 by minimizing the number of cells of the treatment solution that travel therethrough. This in turn helps to reduce pressure against the walls of the stem cells in the treatment solution that can fracture when being manipulated with high pressure. Through applied voltage across each of the coned cells 65 cones up to (0.5 to 5 KV), this electrical charge allows the cells of the treatment solution to be charged as they drip through the openings 65*a*, 65*b*** giving a slight electrical charge.

In certain examples, as the stem cells of the treatment solution go through separation members (e.g., cells 65) of trays 54, 56, a small voltage can pass through thereby charging the cells of the treatment solution. Then, in some examples, upon passing onto the second tray 56 in a pattern defined by how the separation members 65 are oriented, the stem cells of the treatment solution can be heated evenly. However, the design is not so limited and instead the first tray 54 can heat the treatment solution while the second tray 56 can apply the electrostatic charge through respective members 65.

As the treatment solution, including stem cells, flow from one contoured separation member 65 of tray 54 to another member 65 of tray 56, the treatment solution can be warmed up to a precise, predetermined temperature which in turn provides for groups of cells of the treatment solution to get a more even heated temperature. Further, cells of the treatment solution can continue to be charged until the cells or antiseptics meet the piezoelectric nozzle 60. While only conical shaped cells 65 are shown in FIG. 11, other shapes and designs are contemplated for applying a positive or negative charge to a treatment solution (including stem-cells and antiseptics).

It is understood that survival and viability of stem cells can depend on the mode of delivery and that cell viability has been seen to be between 10%-30% but emerging novel methods are increasing viability. The application of stem cells as described herein has been shown to have a superior at least because survival and viability is ensured as the cells go through the conical plate a small voltage passes through the top tray 54 and center tray 56 charging the cells. The heating in dripping into a pattern into a series of narrow passages thus heating them into smaller batches where our conical design is offering the cells to heat evenly. In some examples, the unique contoured cells 65 is configured so the cells or antiseptics of the treatment solution can avoid simply sitting on top of the trays 54, 56 by positioning one or more bubble polymeric materials 63 between each cell 65. In turn, efficiency is achieved and waste is mitigated as to the treatment solution by allowing less impact on the stem cell wall of the treatment solution while it enters the cell 65.

Figure 12:
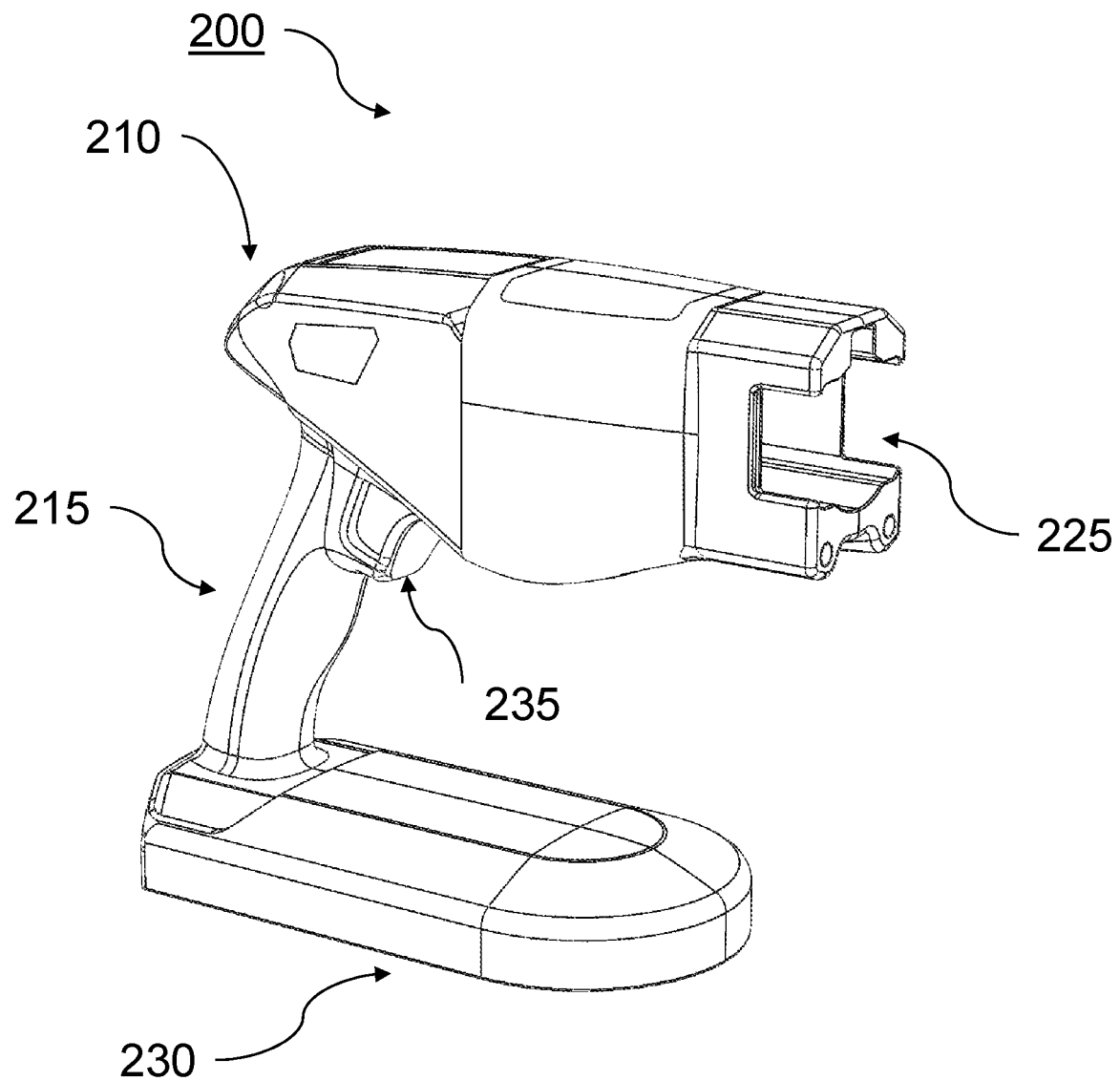
FIG. 12 depicts a perspective view of another example applicator.
Figure 13:
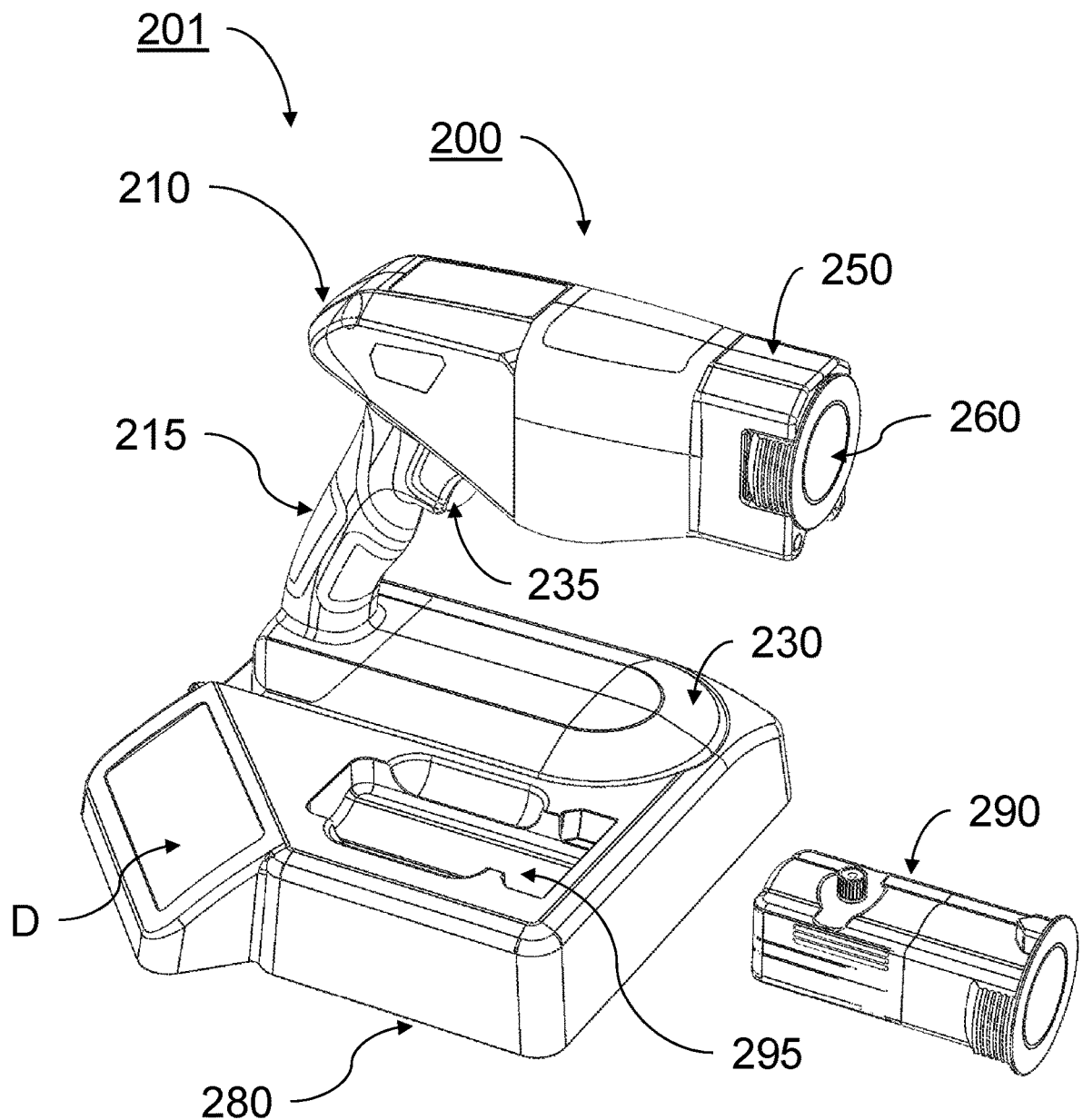
FIG. 13 depicts another perspective view of the example applicator of FIG. 12 assembled with an example base, cartridge, and optical reader.

FIGS. 12-13 show another embodiment of an applicator 200, similar to the previously described applicator 100. As in the previous embodiment, applicator 200 has housing 210 that forms a grip 215 graspable by an end user. Applicator 200 can have an actuator 235 configured to activate or deactivate the applicator 200, including its internal pump (not shown) and delivery of treatment solution from the applicator 200 to the treatment site. Actuator 235 can also be configured to activate and deactivate an electrostatics charger of cartridge 250 (now shown, but similar to cartridge 50) for charging and delivering electrostatically charged treatment solution to the treatment site of the patient. Applicator 200 can also have a cartridge receiving chamber 225, similar to chamber 25, whereby the cartridge 250 is insertable into the cavity formed by chamber 225 as shown in FIG. 12.

FIG. 13 in particular shows a system 201, similar to system 1, that includes applicator 200 assembled with base 280 and optical reader 290 in an exploded state. Optical reader 290 can be housed in optical receiving chamber 295. When applicator 200 and/or optical reader 290 are stored with base 280, respective power supplies of each can be charged (e.g., inductively). FIG. 13 also shows applicator 200 having its cartridge 250 and electrostatic nozzle 260 assembled therewith after having been inserted into chamber 225.

Figure 14A:
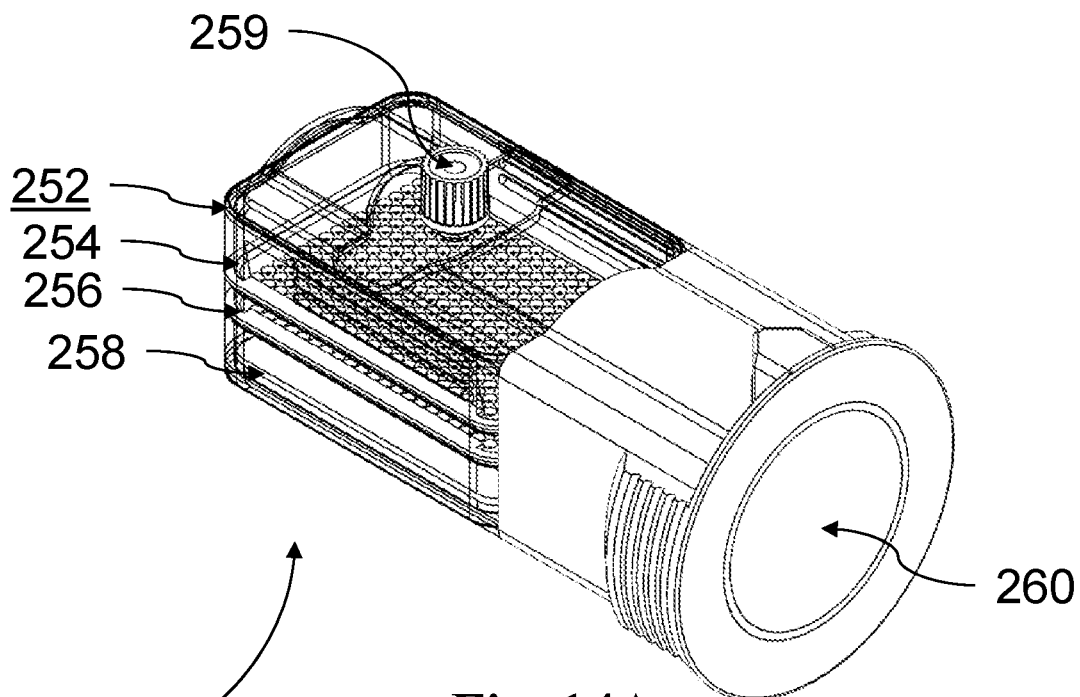
FIG. 14A depicts a perspective view of an example cartridge.
Figure 14B:
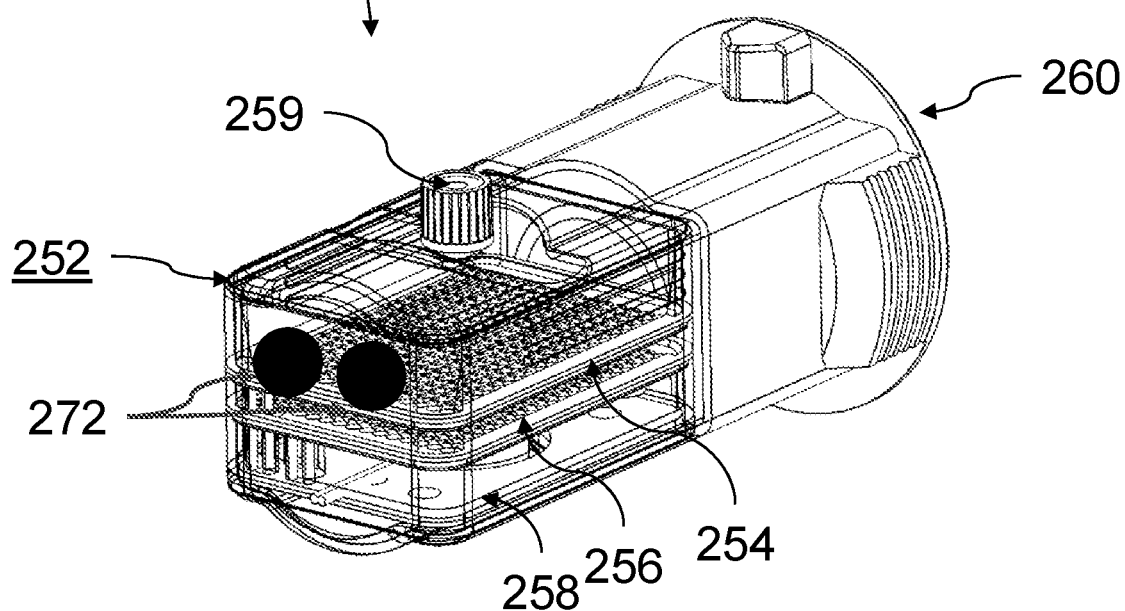
FIG. 14B depicts a perspective view of an example cartridge.

Turning to FIGS. 14A and 14B, a close-up perspective view of example cartridge 250 is shown. In one example, cartridge 250 can have housing 252 that is rectangular (though other shapes are contemplated as needed or required). Similar to previously described cartridge 50 and housing 52, housing 252 can be made from polycarbonate, medical grade plastic and can be disposable. Cartridge 250 can be configured to charge the treatment solution for application from the applicator 200. In turn, the charged treatment solution can seek balance in a negative or positive ground that is provided by the charged treatment site of the patient. Also similar to cartridge 50, cartridge 250 can have aperture 259 on an upper surface of the housing 252 for receiving treatment solution (e.g., a needle can deliver the solution therethrough). In some examples, aperture 259 can include on or more caps or valve mechanisms for controlling flow of treatment solution therethrough. In some embodiments, cartridge 250 can include one or more connectors 272 positioned on a rear surface of housing 252 (i.e. the surface opposite the nozzle 260) to facilitate operative connection with chamber 225. In some embodiments, when operative connection is achieved between connectors 270 and applicators of chamber 225, information related to cartridge 250 can be readily detected for purposes of authenticating treatment solution. For example, a display of base 280, applicator 200, or some device external thereto (e.g., a computing device operatively connected to base 280 and/or applicator 200) can indicate the name of the patient, remaining volume of treatment solution, intended treatment site, and other identifying information related to the treatment solution. In some examples, cartridge 250 can include one or more magnetic connectors 272 for facilitating alignment between chamber 225 and cartridge 250 when being inserted therein.

The optical reader 290 of this disclosure can include an outer housing, an actuator, an internal power supply, and/or one or more optical reader mechanisms contained therewith. In practice, optical reader 290 can include one or more reader mechanisms configured to read information of cartridge 250, including the treatment solution container therein or identifying information printed on housing 252. The one or more optical reader mechanisms can include a light source corresponding photodiode, a laser scanning mechanism, a camera-based reader configured with image processing capabilities for materials (e.g., silica barcoded gel), an LED scanner, an omni-directional scanner, and/or the like. Optical reader 290 can also capable of scanning the cartridge 250 and any contents internal thereto while the cartridge 250 is disposed inside chamber 225 by for example viewing cartridge 250 through a viewing window or transparent portion of canopy 220.

It is understood that any treatment solution of this disclosure comprising stem cells could have its number number of cells per mL (cc) adjusted or conformed to specific therapeutic concentration. For example, the delivery of therapeutic relevant concentration of stem cells can range from 100 cells/uL to 40,000 cells/uL. Therefore, the volume and concentration of any cartridge of this disclosure should be made available to the clinician depending on the size and severity of wound/lesion.

Figure 15A:
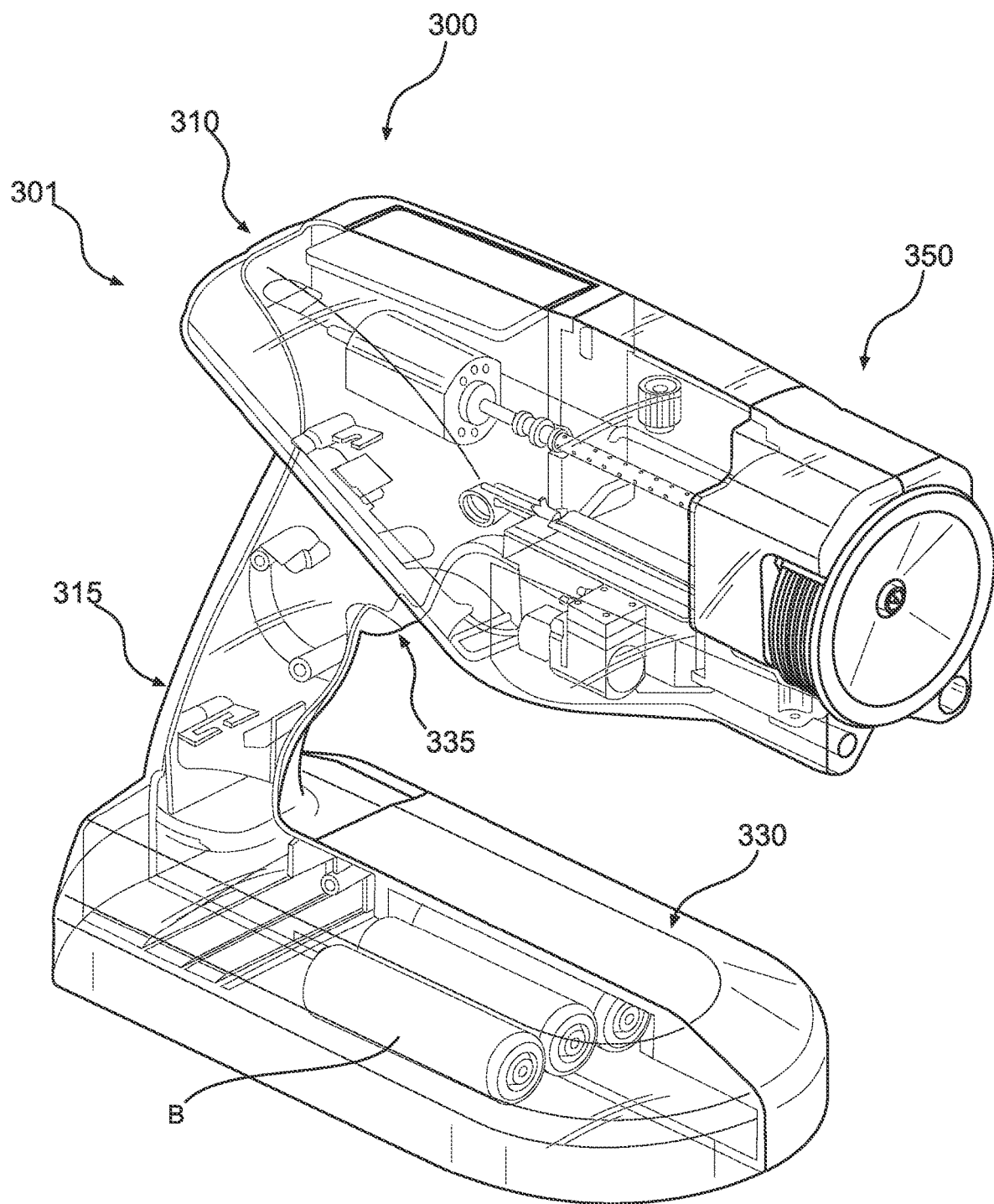
FIG. 15A depicts a perspective view of another example applicator.
Figure 15B:
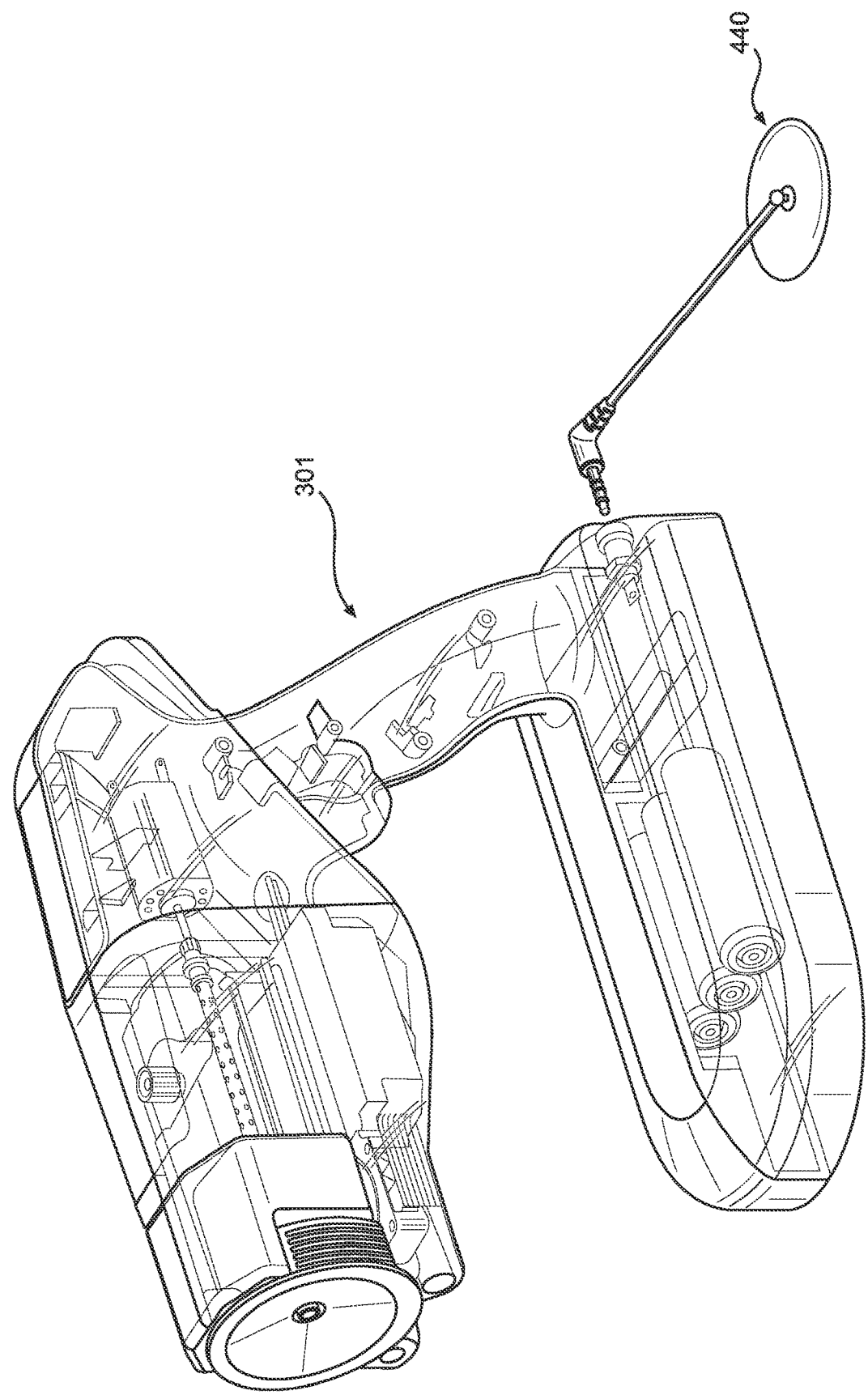
FIG. 15B depicts a perspective view of the example applicator of FIG. 15A with an example ground electrode.
Figure 16:
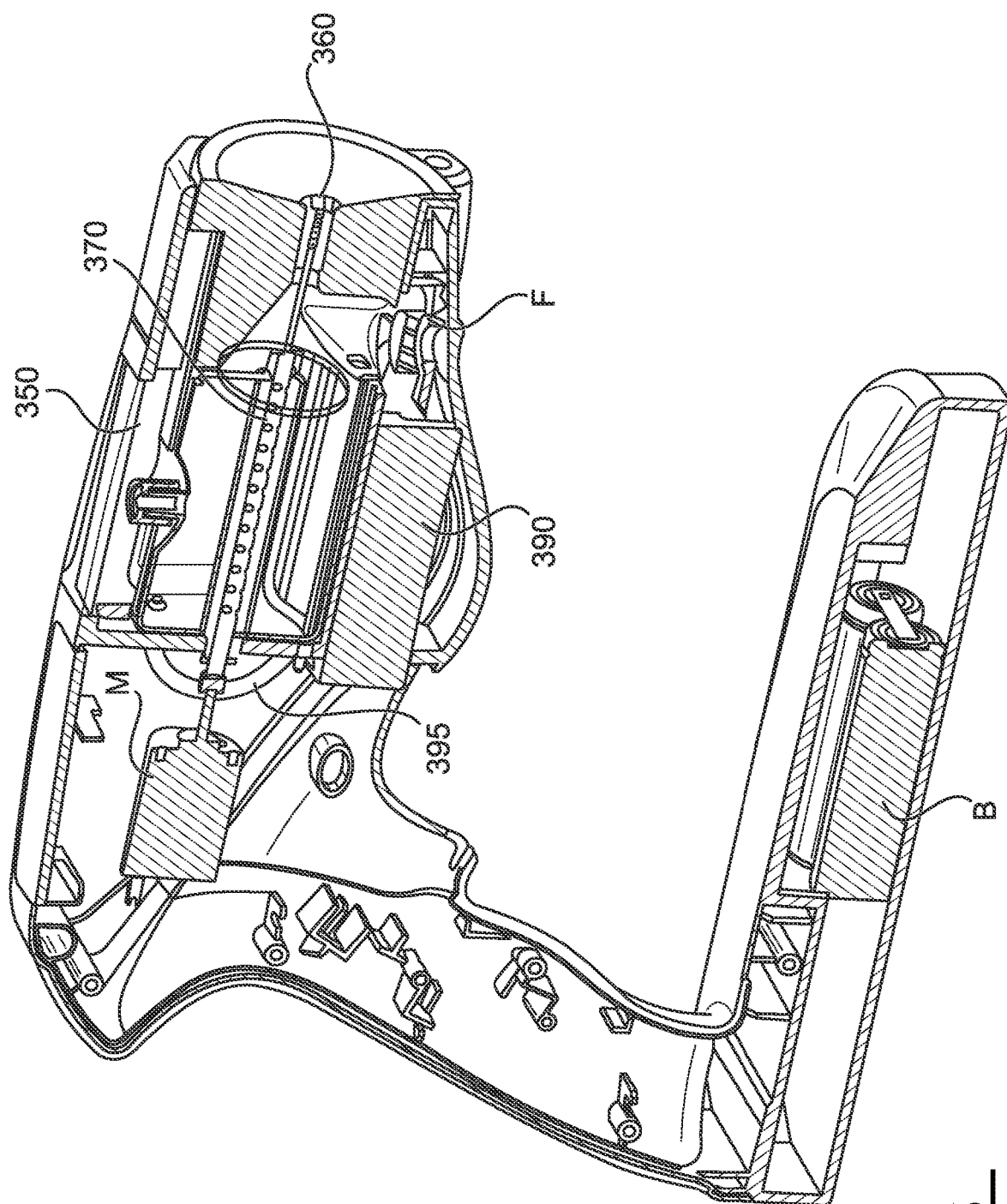
FIG. 16 depicts a perspective view along a cross section of a center line of the example applicator of FIG. 15.

FIGS. 15A-16 show another embodiment of an applicator 300, similar to the previously described applicator 100/200. Applicator 300 is configured to implement a direct charging method to charge the aqueous, treatment solution in use for generating a coat from a liquefied polymer. Specifically, applicator 300 can be an electrospinning device configured to provide a liquified bandage for wounds, burns, cuts and the like, and to fabricate artificial skin.

In electrospinning, it is understood that a polymer solution from a storage unit can be applied or sprayed from an opening by repulsion of charges accumulated at a droplet tip when the electrical potential applied increases beyond some amount. As the charged solution travels to some collection point, the solution will dry and form nonwoven fibrous mats, which in this case can be the wound site of a patient. Direct charging in this disclosure is understood as low voltage electrode and aqueous, treatment solution coming into physical contact with each other. As in the previous embodiment, applicator 300 has housing 310 that forms a grip 315 graspable by an end user. Applicator 300 can have an actuator 335 configured to activate or deactivate the applicator 300, including its internal pump (not shown) and delivery of treatment solution from the applicator 300 to the treatment site. Actuator 335 can also be configured to activate and deactivate an electrostatics charger of cartridge 350 (not shown, but similar to cartridge 50, 250) for charging and delivering electrostatically charged treatment solution to the treatment site of the patient.

Cartridge 350 can contain treatment solution having a polymer reagent dissolved in one or more solvents. Once pressurized, the mixture can be forced through a dispensing needle 370 with radial nozzles while spinning. As this reagent is forced through the radial spinning nozzles of needle 370, a stream of air can evaporate the solvent and create the matrix which will be delivered to the wound site. Applicator 300 can also have a cartridge receiving chamber 325, similar to chamber 25, whereby the cartridge 350 is insertable into the cavity formed by chamber 325. FIG. 15B depicts a perspective view of the applicator 300 example ground electrode 440 to be attached to a patient for ground.

In some examples using applicator 300, the treatment solution once applied from nozzle 360 can result in electrospun porous nanofibers that mimic important features of the extracellular matrix composition (ECM), including providing scaffolds favorable for tissue regeneration and wound healing. In some examples, such electrospun nanofibers can regulate skin cell behavior via transmembrane receptors or intracellular signaling pathways. Nanofibers of this example can incorporate bioactive material (e.g., DNA, enzymes, and growth factors) that can allow for the maintenance of proliferation and migration of primary cells seeded on the scaffolds.

Biopolymers contemplated for use with applicator 300 can include materials such as animal fat, plant fibers, and honey pastes were commonly used in the past as wound dressings. One important aspect of wound management is for the injured site to be properly oxygenated for wound healing. Oxygen is critical for cell metabolism, energy production, and all phases of wound healing. Superoxide, for oxidative killing of pathogens, produced by leukocytes is dependent on oxygen levels. Temporary hypoxia has been shown to stimulate wound healing, but chronic hypoxia delays the process. Hypoxia induces macrophages, fibroblasts, and keratinocytes to produce cytokines and growth factors crucial for cell proliferation migration and chemotaxis, and angiogenesis in wound healing. Reactive oxygen species (ROS), during normal oxygenation, induce wound healing.

A liquid skin bandage example of applicator 300 can include biocompatible polymers not limited to synthetic polymers for proper wound coverage. The solution of the liquid skin bandage example can also include a mixture solution of more than one natural polymer and delivered to a treatment site through an applicator of this disclosure. The resultant skin bandage can allow for an aerobic environment as oxygen is able to pass because of the permeability properties. The solution of the liquid skin bandage example can be flexible and include anti-microbial properties.

A non-exhaustive list of commercially available polymers contemplated for use in and/or with wound dressings of this disclosure include: Polymeric foam (e.g., Flexan, Biopatch, Crafoams, Biatain, Cutinova), Polymeric hydrogels (e.g., Cultinova gel, Biolex, Tegagel, 2nd skin Felxderm, Dry dressing), Polymeric alginates (e.g., AlginSan, AlgiSite, Sorbsan, Kaltostat, Omiderm), and Polymeric hydrocolloides (e.g., Idosorb, Debrisan, Sorbex, Douderm). Chronic hypoxia can also increase the levels of cytokines and proteases causing damage to surrounding tissue. The herein disclosed electrostatic delivery of artificial skin bandage is particularly advantageous in resolving these issues in and/or through a cartridge of this disclosure to spray on after stem cell application through one or more of the herein disclosed approaches. In some examples, delivery of the artificial skin bandage is done to protect the wound from invasive pathogens and permeable to oxygen for proper healing.

The use of natural polymers is prevalent in modern medicine, for burn and wound dressings, because of biodegradability, biocompatibility, and similarity to the ECM (Extracellular Matrix). Polysaccharides are used in wound and burn management, though they vary greatly in chemical properties. The polysaccharides used for this purpose can be acidic, basic, or sulfated. Some examples are homoglycans (e.g., cellulose, dextran, and starch) and/or monomers that are repeated throughout the chain length. Alginates, obtained from processed algae, are polysaccharides that can also be used in wound dressings and are absorbent in nature and form hydrophilic gels. Others contemplated for use include agar, pectin, and bovine serum. Other natural materials contemplate for use with the liquid bandage solution include collagen, chitosan, hyaluronic acid, and carboxymethyl chitosan. Biodegradable polymers can be effectively used with this example for several biomedical applications such as drug delivery, dental, orthopedic and tissue engineering. A cartridge of this embodiment can also include anti-microbial properties, permeable woven biocompatible and stable polymer dressing, and protective support for stem cell tissue regeneration.

Turning back to FIG. 15A-15B, cartridge 350 can be disposable and configured for use with applicator 300 with an electrospinning delivery system to apply a polymer fiber matrix to wounds for rapid healing. In some examples, cartridge 350 can include the treatment solution, including one containing a polymer solution dissolved in appropriate solvents. Under pressure, the solution can be forced through dispensing needle 370 with radial nozzles 360 while spinning. As the treatment solution of this example is forced through the radial spinning nozzles 360, a stream of air can evaporate the solvent and create the matrix which will be delivered to the wound site of the patient.

FIG. 16 in particular shows system 301 shown along a cross section of a center line to reveal certain inner components and features thereof. Applicator 300 can be used with an optical reader (not shown) and be configured for use with cartridge 350 and radial nozzle 360. A motor M is shown in communication with needle 370 connected with a radial gear 376 configured to drive and rotate needle 370. A pressure pump 390 is shown disposed underneath cartridge 360 and directly adjacent an electrospinning fan F. Tube 395 can be configured as a high pressure supply tube and connected to pump 390 and in fluid communication with a storage tank of cartridge 350. Fan F is configured to evaporate sprayed treatment solution from cartridge 350, including polymer solution.

Figure 17:
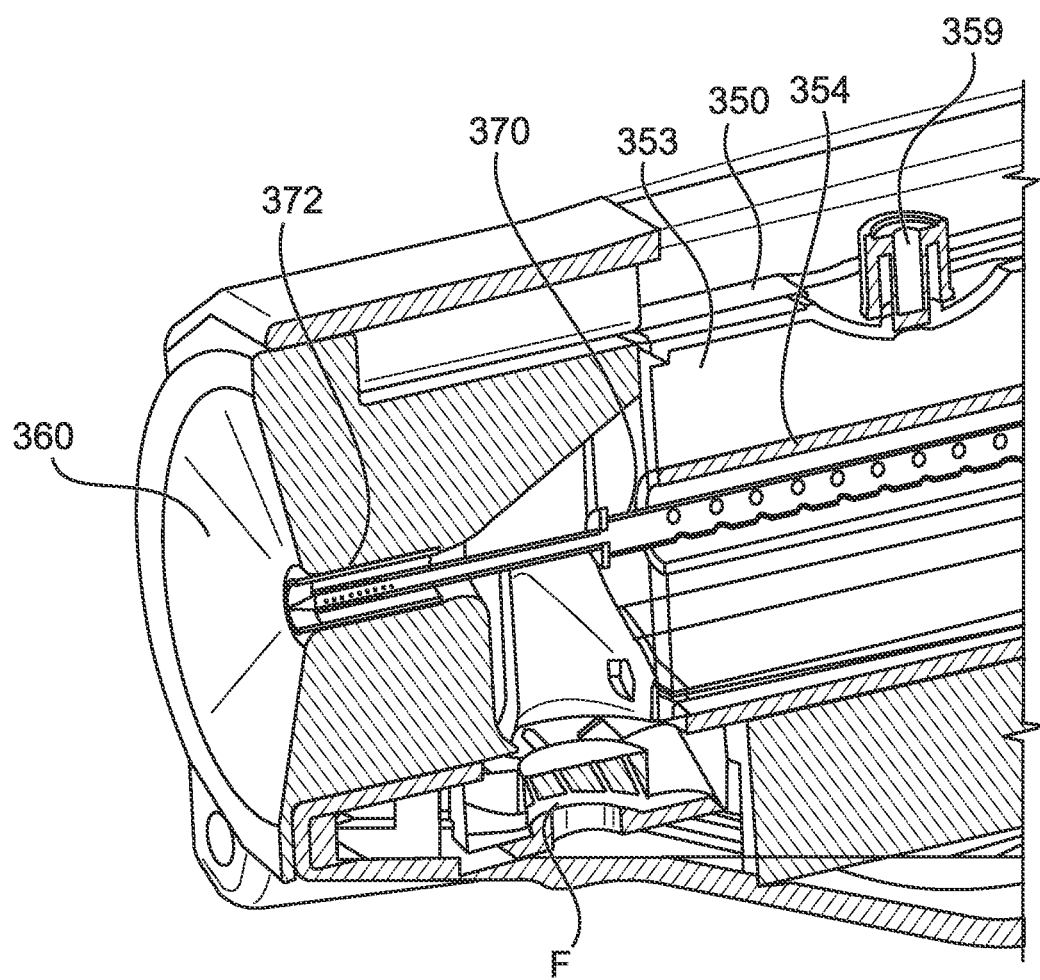
FIG. 17 depicts a close-up perspective, cross-sectional view of the example distal tip of the applicator of FIG. 15.

FIG. 17 depicts a close-up perspective, cross-sectional view of the example distal tip of the applicator 300. Needle 370 can include a distal tip 372 having a venturi for high velocity airflow, whereby tip 372 can be supplied with room temperature or heated air to facilitate the evaporative and fibrous matrix generation. The venturi of tip 372 can be supplied with room temperature or heated air, either one chosen to facilitate the best evaporative and fibrous matrix generation.

Needle 370 can be seen axially positioned within a needle chamber 353 of cartridge 350. Cartridge 350 can include treatment solution storage 354 disposed internal to cartridge 350 between chamber 353 and the outer shell of cartridge 350. Storage 354 can be filled with a single treatment solution formulation or multiple treatment solution formulations, including those containing solvent(s), polymer(s), and/or other active ingredients or medicines. Storage 354 can be constructed from solvent resistant materials. Cartridge can also include aperture 359 on an upper surface of the housing 352 for receiving treatment solution (e.g., a needle can deliver the solution therethrough). In some examples, aperture 359 can include on or more caps or valve mechanisms for controlling flow of treatment solution therethrough.

Figure 18:
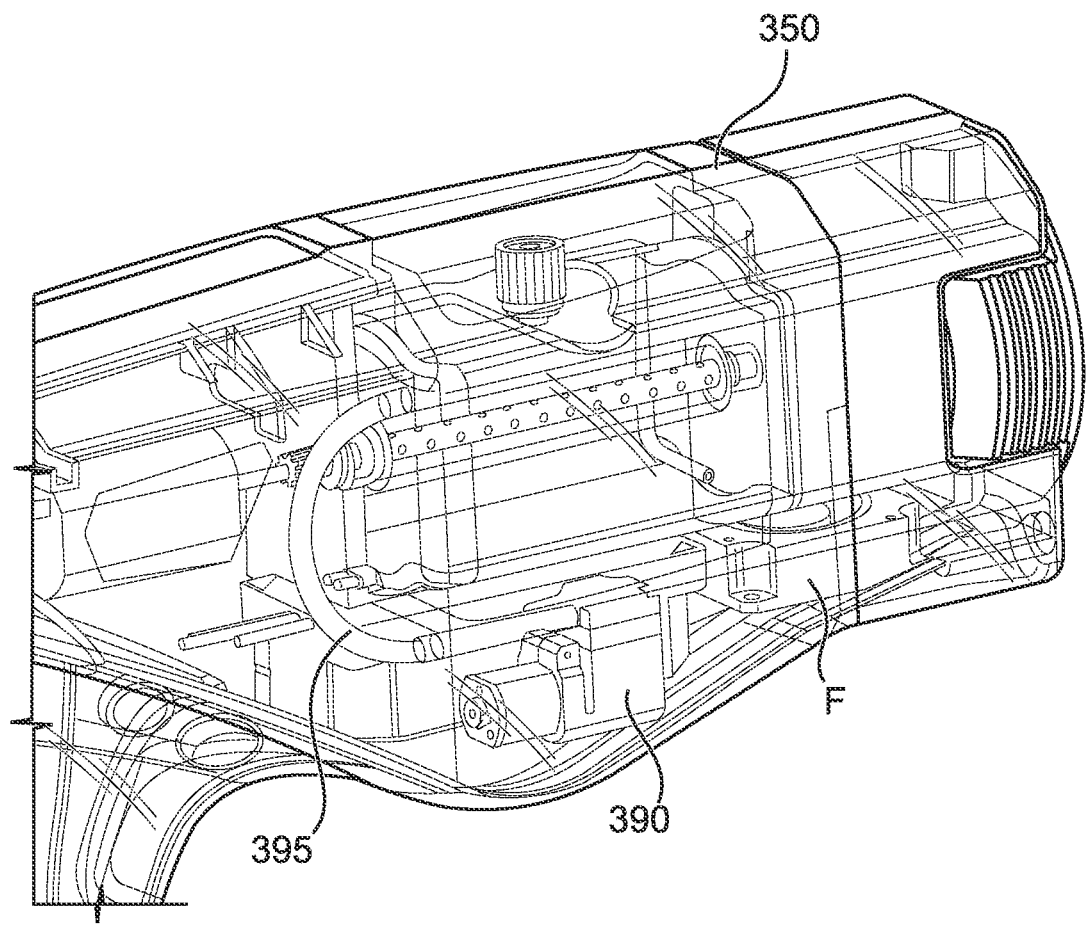
FIG. 18 depicts a close-up rear perspective of the example applicator of FIGS. 15-16.

FIG. 18 depicts a close-up rear perspective view of cartridge 350 assembled with applicator 300. As can be seen and previously discussed, pump 390 can pressurize storage 354 and allow treatment solution to be forced through the tip(s) of needle 370 whereby pump 390 can be chosen to provide a variety of pressure depending on the polymer solution being delivered.

Figure 19A:
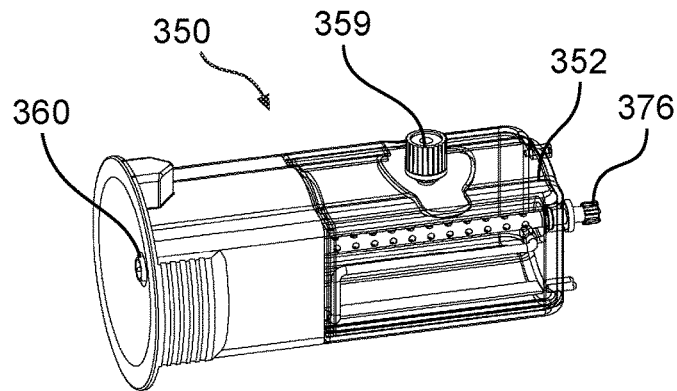
FIG. 19A depicts a perspective view of an example cartridge.
Figure 19B:
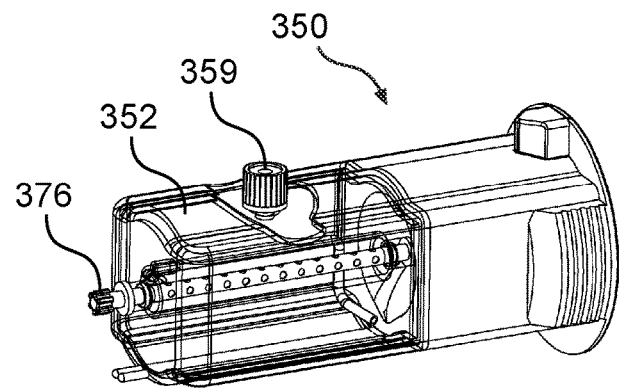
FIG. 19B depicts a perspective view of the example cartridge of FIG. 19A.
Figure 19C:
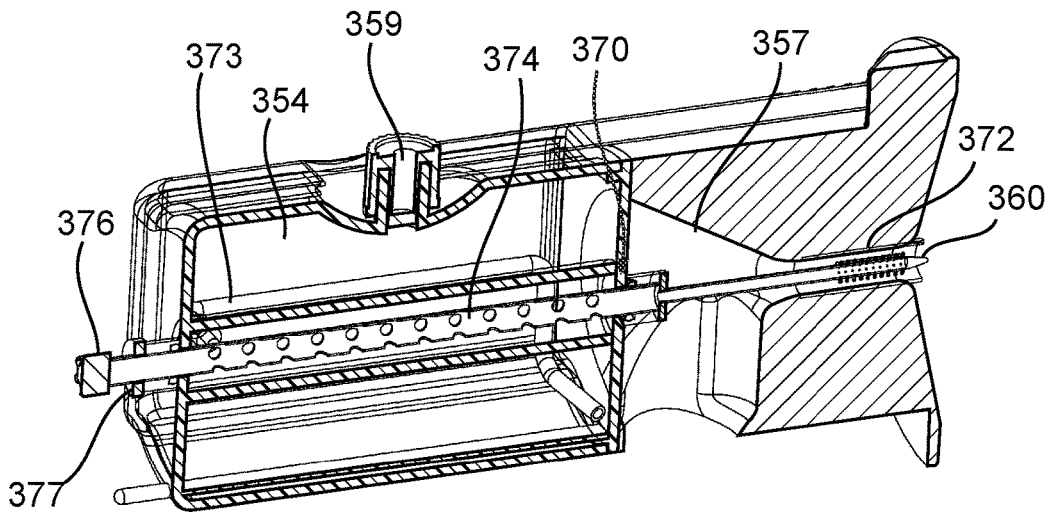
FIG. 19C depicts a perspective view of the example cartridge of FIG. 19A.

Turning to FIGS. 19A and 19C, perspective views of example cartridge 350 are shown. Cartridge 350 can have housing 352 that is rectangular (though other shapes are contemplated as needed or required) and can be made from polycarbonate, medical grade plastic and can be disposable. Cartridge 350 can be configured to charge the treatment solution via electrospinning for application from the applicator 300. Cartridge 350 can be filled with treatment solution, including one that includes a specialty polymer reagent. Storage 354 can be pressurized from pump 390 (see, e.g., FIG. 16). When storage 354 is pressurized from pump 390, a feeding tube 377 of needle 370 pressurizes and supplies fluid to the needle bore.

While the motor M connects to needle 370 at junction 376, motor M in turn spins needle 370 and the resultant high pressure drives the fluid, treatment solution out of nozzle 360 to create a fine mist of treatment solution on the treatment site. Fan F then forces fluids (e.g., air) through the venturi of tip 372 accelerating the fluid flow to rapidly evaporate the solvent of the treatment solution and then delivers a fine stringy matrix which gets deposited on the wound surface. O-Rings 377 on both ends of the tube 374 in the storage housing 354 allows for a seal and the storage 354 to be pressurized.

The electrospinning process of this example begins when electric charges move into the polymer, treatment solution via needle 370 thereby causing instability within the treatment solution as a result of the induction of charges on polymer droplets. At the same time, the reciprocal repulsion of charges produces a force that opposes the surface tension, and ultimately the treatment solution flows in the direction of the electric field. A further increase in the electric field causes the droplet (e.g., spherical shaped) to deform and assume a conical shape. At this stage, ultrafine nanofibers can emerge from the conical polymer droplet.

The electric field strength of this example can overcome surface tension of the droplet and generates a charged liquid jet. The jet is then elongated and whipped continuously by electrostatic repulsion until it is deposited on the grounded collector. The solvent evaporates on the way and the jet solidifies to form a nonwoven fibrous membrane. The processing flexibility of this technique enables fiber fabrication from a broad range of precursor materials such as synthetic polymers, natural polymers, semiconductors, ceramics, or their combinations A stable charge jet can then be formed only when the polymer solution has sufficient cohesive force. During the process, the internal and external charge forces can cause a whipping of the liquid jet which allows the polymer chains within the solution to stretch and slide past each other and results in the creation of fibers with diameters small enough to be called nanofibers. It is understood that there are several factors that affect the electrospinning process. These factors are classified as electrospinning parameters, solution and environmental parameters. The electrospinning parameters can include the applied electric field, distance between the needle and collector, flow rate, and needle diameter. The solution parameters include the solvent, polymer concentration, viscosity and solution conductivity. The environmental parameters include relativity humidity and temperature. One or more of these parameters directly affect the generation of smooth and bead-free electrospun fibers in applicator of treatment solution from applicator 300.

Figure 20A:
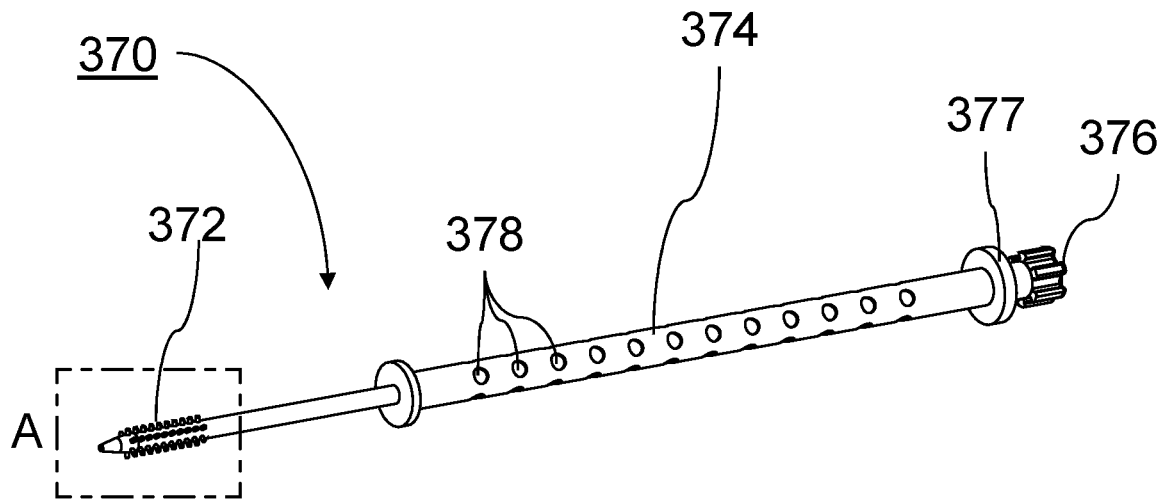
FIG. 20A depicts a perspective view of an example needle for use with the example applicator of FIGS. 15-16.
Figure 20B:
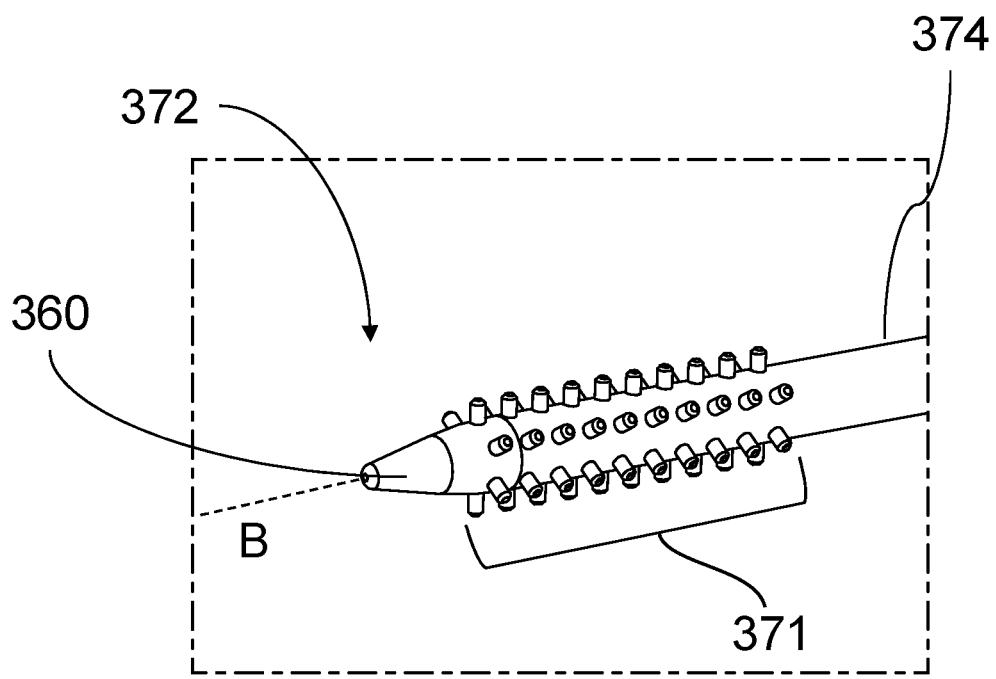
FIG. 20B depicts a close-up perspective view of the example distal tip of the needle of FIG. 20A.

FIG. 20A depicts a perspective view of needle 370. FIG. 20B depicts a close-up perspective view of distal tip 372 of the needle of FIG. 20A taken at section A-A. In particular, needle 370 can include tube 374 being substantially elongate with a plurality of radially separated feed tube holes 378 positioned along the length of tube 374. Tip 372 can also include a plurality of radially separated distribution elements 371 protruding outwardly from tube 374 to create the mist or stream of electrostatically charged treatment solution. Elements 371 taken together can form a needle matrix oriented radially or any angle point forward that facilitates a preferred or required spray application pattern. Once connected to motor M via junction 376, needle assembly 370 can be rotated and in turn be capable of providing a flow of the charged polymer radially with respect to the longitudinal needle axis B. In some examples, elements 371 can be oriented orthogonal relative to axis B or some angle thereof (e.g., an angle between 0 and 90 degrees such as 45 degrees). Any amount or dimension of elements 371, including height, nozzle size, length of each element from tube 374, can be varied to allow for any combination of fibrous covering once applied as a liquid bandage at a wound site. Preferably, needle 370 as shown is configured to be rotated and spray the dissolved polymer radially and then subject that treatment solution to a very high velocity airflow that dries the solvent and redirects the fiber bundle to the target. In some examples, a wider dispersion pattern can also be provided as a result of the depicted configuration of FIGS. 20A-20B.

Figure 21:
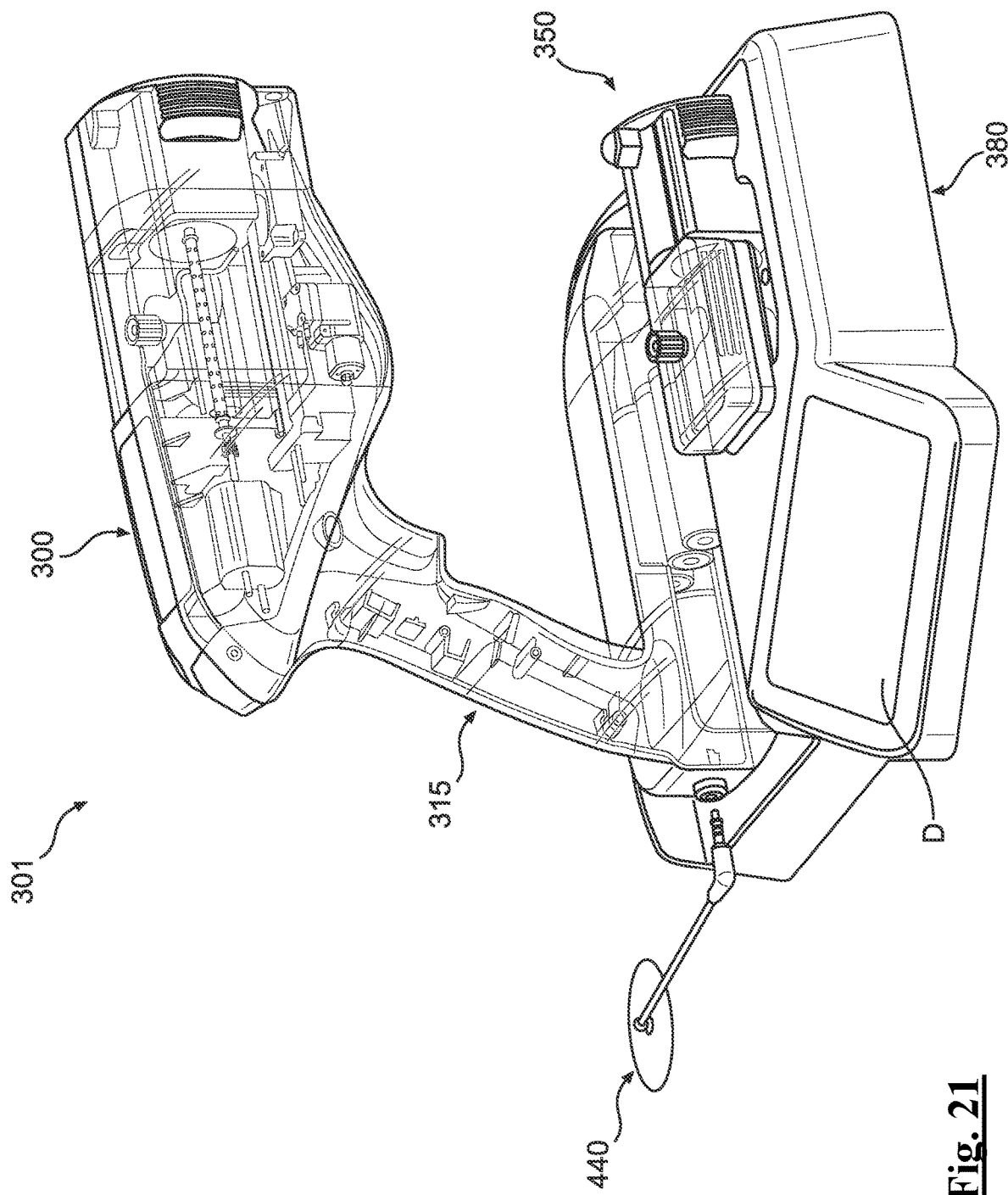
FIG. 21 depicts a perspective view of the example applicator of FIGS. 15-16 positioned with an example base and cartridge assembly.

FIG. 21 shows system 301, similar to systems 1/201, that includes applicator 300 assembled with base 380. When applicator 300 is stored with base 380, respective power supplies of the applicator can be charged (e.g., inductively). FIG. 21 also shows applicator 300 having its cartridge 350 and electrostatic nozzle 360 assembled therewith after having been inserted into chamber 325 of applicator 300. System 301 can also include a spare cartridge 350 as well as a display D that functions as a control center with system status information, patient information, cartridge information, and/or the like. It is understood that base 380 can be configured to monitor and notify user of all system functions. Applicator 300 and/or base 380 can also utilize heaters to warm the treatment solution, the exiting air flow and/or the needle solution delivery mechanism as needed or required.

In some examples, a cartridge of this disclosure can include a disinfecting cartridge that includes a mixed reagent with an antimicrobial solution of certain percentage. The mixed reagent can include Biguanides (e.g., chlorhexadine also known as chlorhexadine gluconate, a widely used biocide in antiseptic products; in particular handwashing and oral products, but also as a disinfectant and preservative). These disinfectants have a broad-spectrum efficacy, substantivity for the skin, and low irritation. Iodophores (e.g., Betadine, such as povidone-iodine and poloxamer-iodine, are much more stable, have fewer irritant characteristics and exert better microbicidal action than aqueous iodine solutions). The solution, electrostatically delivered by application of a positive charge, can allow for even distribution of reagent on the site of injury and bind to the bacterial membrane, known to be negatively charged, and thereby destroying the integrity of the cell.

Most surface disinfectants or decontamination agents are limited by either low performance against challenging pathogens (or refractory contaminants) or are comprised of harsh chemicals that are toxic to the user and hazardous in the environment. In particular, the use of toxic chemicals requires specified use concentrations along with specified contact time in order to achieve the intended antimicrobial effect. Oftentimes, however, the handling and use of these chemicals present hazards to the user, in addition to the environment, and can cause damage to the materials being disinfected (or decontaminated). The disclosure here describes methods to disinfect or decontaminate surfaces and air space by methods of activating oxidizing mixtures at or near the surface to be treated. The treatment solution of certain examples in this disclosure resolves these and other problems in the art.

For example, the compositions and chemical properties of disinfectant treatment solutions of this disclosure can include oxidizing mixtures for applications in high-level hospital disinfection, hospitality and facilities cleaning, sanitization, and deodorization, surface disinfection and decontamination as well as agricultural (greenhouse and crop) plant and soil treatment. The components of the mixtures in some examples can be "activated" to improve antimicrobial and decontamination performance.

In some examples, the components and the methods to produce the oxidizing mixtures of the treatment solution are designed to form mixtures that promote and sustain the formation of reactive oxygen species (ROS) upon activation. Formation of ROS at or near the surface to be cleaned, disinfected or decontaminated can boost the antimicrobial performance (or decontamination performance) of the non-toxic composition. Further, the compositions can be peroxygen based (e.g., mixtures of at least one peracid, percarbonate, persulfate, perborate and/or peroxide) and can be formulated and/or prepared in ways that support the activation to form ROS and excludes components and conditions that quench ROS. The mixtures can optionally contain other components including detergents, surfactants, builders, pH modifiers, fragrances and/or color additives, etc.

In some examples, the oxidizing mixtures can be activated to deliver effective concentrations of ROS to the surface. For example, oxidizing mixtures can include chemical activation and/or photolytic activation of oxidizing mixtures at or near the surface to be disinfected, or decontaminated. The disclosure can also include methods to introduce chemical activators, mixtures of activators, or catalytic photons into a spray or mist at or near the surface to be disinfected. The disclosure can also include methods to disinfect and/or decontaminate the air space between the applicator nozzle and the surface with activated (e.g., boosted) oxidizing mixtures The oxidizing mixtures in some examples can be activated at or near the surface to be decontaminated or disinfected. The ROS are extremely short-lived and can require activation on or near the surface. The oxidizing mixtures can be activated by heterogeneous chemicals (catalysts), homogeneous chemicals (catalysts), or by activating photons. The activation method can include introduction and mixing of the activator (catalyst) component with the mist or spray of the oxidizing mixture from the applicator. A portion of the oxidizing mixture can be immediately reactive with the catalyst forming ROS in the treatment solution stream from the applicator. Another portion of the oxidizing mixture can entrain the activating chemical (catalyst) component (e.g., in the case of heterogeneous catalysts and homogeneous catalysts) and can deliver a portion of the activating chemical (catalyst) to the surface along with the oxidizing mixture. Once covering the surface, the activating chemical (catalyst) can continue to react and generate ROS on the surface to be decontaminated or disinfected.

It is understood that homogeneous chemical activators of this emboximent can include aqueous soluble transition-metal complexes and soluble transition-metal salts, for example. Soluble photocatalysts may also be utilized. It is understood that heterogeneous chemical activators can include ozone gas (O3), aqueous insoluble transition-metals (small particles), or other insoluble activating materials like activated carbon. Insoluble photocatalysts may also be utilized. It is understood that photons can be introduced to the stream of treatment solution from the applicator of the oxidizing mixture. Similarly, photons can be introduced to the surface after the surface is covered with oxidizing mixture. The photons can be of a specific wavelength or a range of wavelengths that directly activate the oxidizers to form ROS. In another embodiment, the photons can be of a wavelength that activates a homogeneous and/or heterogeneous photocatalyst. The activation chemical (catalyst), or mixtures of activators (catalysts), or combinations thereof at least one chemical activator (catalyst) and activating photons are introduced into a stream of treatment solution from the applicator of the oxidizing mixture to form ROS at and near the surface that is being sprayed.

In some examples, ozone gas can be used as a chemical activator. A volume of ozone gas of a specified concentration can be mixed into the aqueous activator stream in a specified volume ratio. The ozone gas can be mixed either pre- or post-nozzle and can be present in three (3) zones: 1) some immediately dissolves (O3 dissolved) and can begin to react, 2) some portion of ozone becomes entrained in the spray (O3 entrained) and is delivered to the surface undissolved and unreacted, and 3) the remaining portion exists in the air space between the sprayer and the surface (O3 gaseous).

Another example mode of activator introduction involves the use of a double tank where the activator (homogeneous mixture or heterogeneous suspension) can be contained in relatively high concentration in one tank while the aqueous oxidizing mixture exists in the other tank. This embodiment allows the mixing of two liquid streams, with the activator present in a solvent that allows higher concentrations. This can be achieved by positioning a double tank in the applicator itself or a split tank supplied to the applicator nozzle. One side of the tank can include the aqueous oxidizer, while the other side of the tank can include ozone dissolved in a solvent that enhances the ozone solubility (alcohol for example). The two separate mixtures can be pumped and mixed together either pre- or post-nozzle.

In some examples, to attenuate the discomfort and pain associated with the chronic/acute wound and/or burn to the wound site, the reagent can have an added analgesic property. The reagent can include a certain percentage of the following: Approved pharmaceutical reagents such as Lidocaine, tetracaine, benzocaine that is generally well tolerated and non-toxic when applied topically as recommended. The reagent can also include any approved analgesic solution which offers relief from the discomfort associated with epidermal injuries. Examples for others include, but are not limited to, Pramoxine hydrochloride, camphor, menthol, phenol, and diphenhydramine, which can bring relief. Pain caused by the stimulation of free nerve endings.

Regarding pain management, pain is understood as being caused by the stimulation of free nerve endings. When the nerve endings are stimulated, sodium enters the neuron causing depolarization of the nerve and the generation of an action potential. The action potential proceeds to propagate to the CNS and signals pain. The pharmacodynamics of analgesics are to inhibit the voltage-dependent gated sodium channels (VDSCs) on the neuron membrane and inhibiting the propagation of the action potential. There can also be a situation where only the disinfectant is the stand-alone reagent found in the cartridge of this example embodiment to apply. The same can be said about the analgesic solution with its own delivery cartridge. Therefore, the disposable reagent cartridge can be loaded onto an applicator of this disclosure and the clinician can then deliver the reagent to the wound site and proceed to the next step of delivering therapeutic biologics (e.g., allogenic or autologous stem cell solution). In turn, the wound healing process is accelerated by the solution of this disclosure by eliminating the susceptibility of infections and attenuating the discomfort associated with the epidermal trauma.

In some examples, when the nerve endings are stimulated, sodium enters the neuron causing depolarization of the nerve and the generation of an action potential. The action potential proceeds to propagate to the CNS and signals pain. The pharmacodynamics of analgesics are to inhibit the voltage-dependent gated sodium channels (VDSCs) on the neuron membrane and inhibiting the propagation of the action potential. There can also be a situation where only the disinfectant is the stand-alone reagent found in the cartridge to apply. The same can be said about the analgesic solution with its own delivery cartridge.

The cartridge of this example with its disposable reagent can loaded onto the applicator of this disclosure and the clinician can deliver a reagent to the injury site and proceed to the next step of delivering therapeutic biologics (e.g., allogenic/autologous stem cell application). In turn, the process can accelerate wound healing by eliminating the susceptibility of infections and attenuating the discomfort associated with the epidermal trauma.

Figure 22:
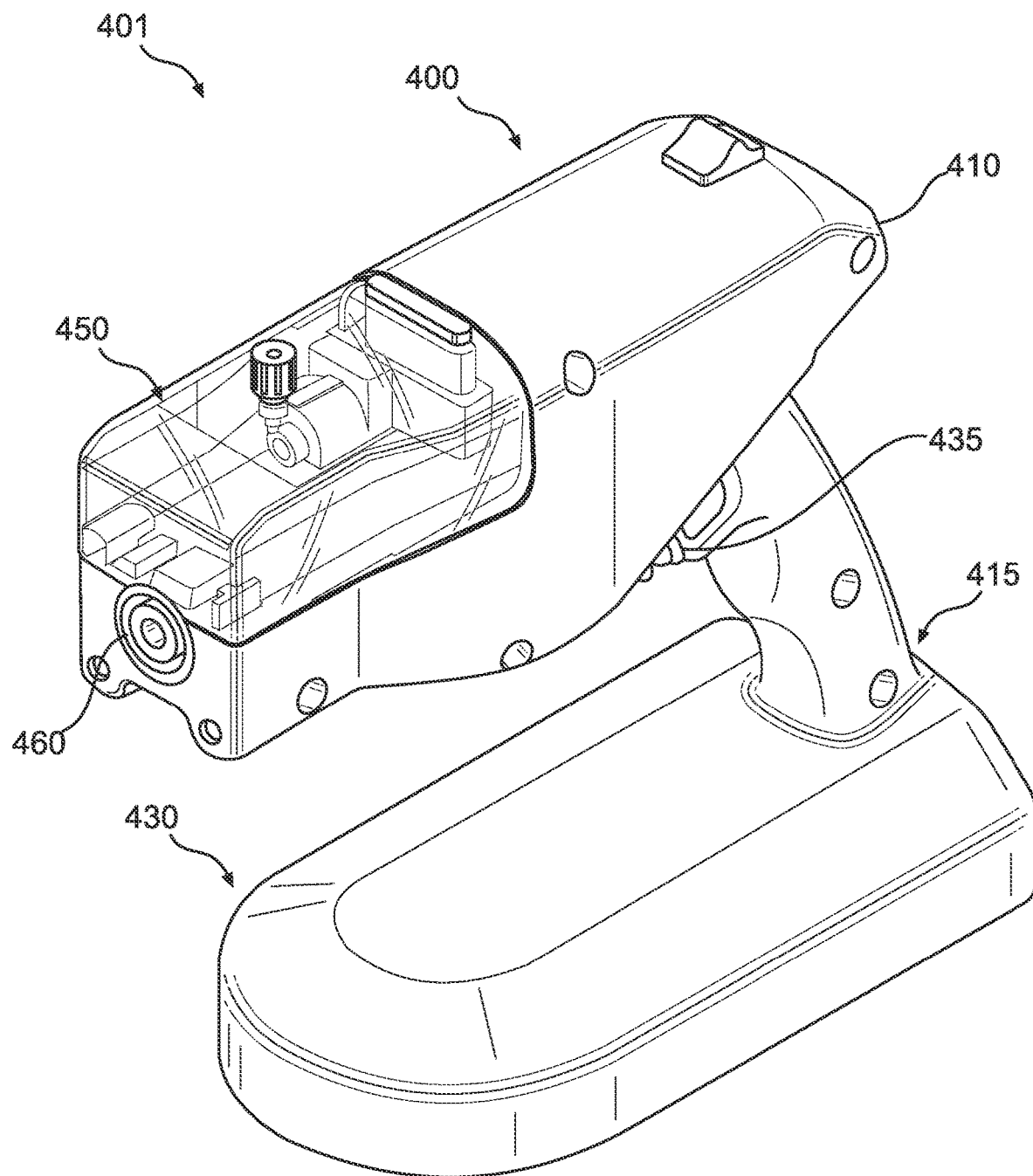
FIG. 22 depicts a perspective view of another example applicator positioned with an example base and cartridge assembly.
Figure 23:
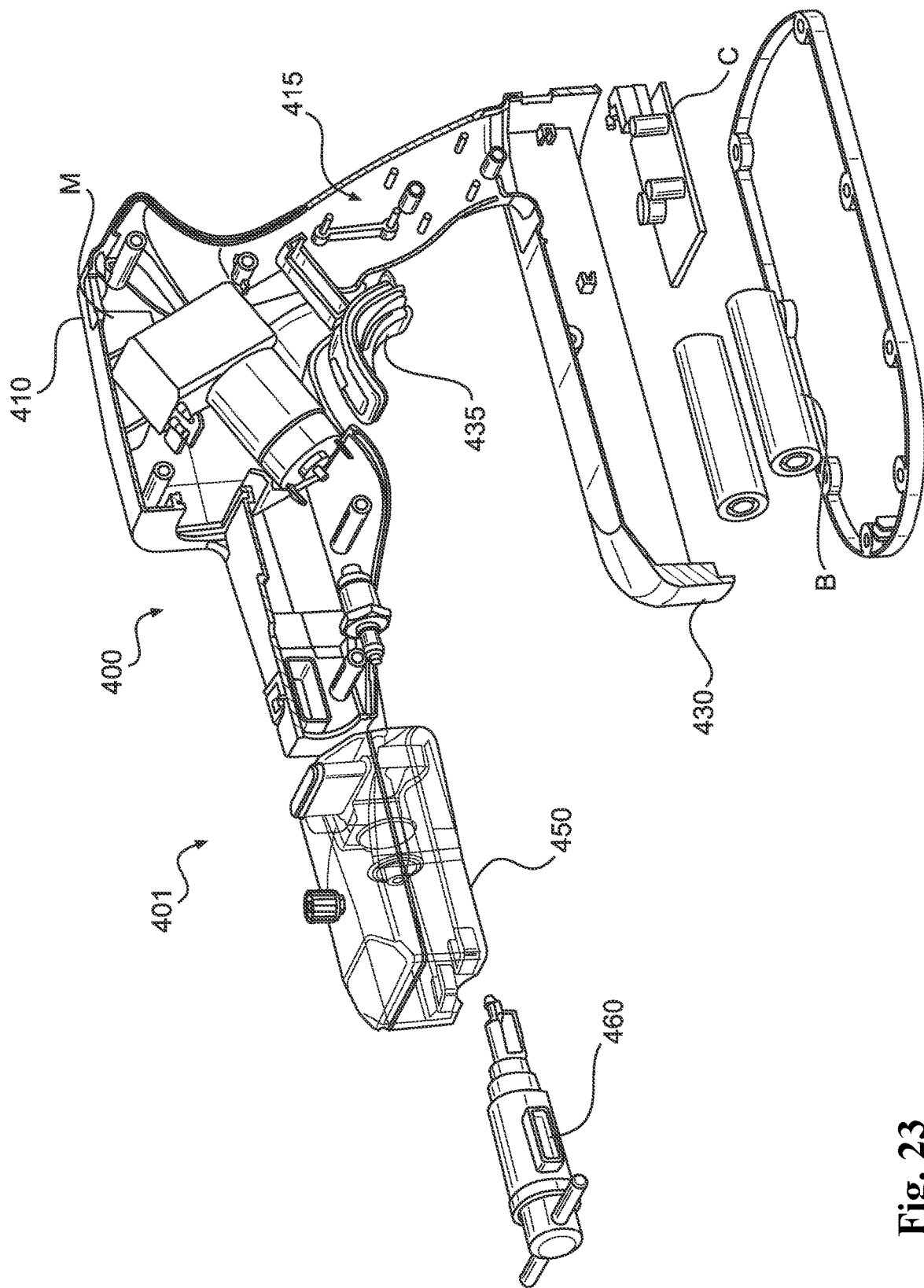
FIG. 23 depicts an exploded, perspective view of the applicator shown in FIG. 22.

FIG. 22 shows system 401 with applicator 400. FIG. 23 shows an exploded view of system 401. As can be seen, applicator 400 has housing 410 that forms a grip 415 graspable by an end user. Applicator 400 can have an actuator 435 configured to activate or deactivate the applicator 400, including its internal pump (not shown) and delivery of treatment solution from the applicator 400 to the treatment site. Actuator 435 can also be configured to activate and deactivate an electrostatics charger of cartridge 350 (not shown, but similar to cartridge 50, 250, 350) for charging and delivering electrostatically charged treatment solution to the treatment site of the patient. Cartridge 450, as in previously described cartridges, can contain treatment solution having a polymer reagent dissolved in one or more solvents. Cartridge 450 can have housing 452 that is rectangular (though other shapes are contemplated as needed or required) and can be made from one or more molded parts of polycarbonate, medical grade plastic and can be disposable. Cartridge 450 can be configured to charge the treatment solution for application from the applicator 400. Once pressurized, the mixture can be forced through nozzle 460 thereby delivering the solution that creates the matrix to the wound site. Cartridge 450 can also be disposable and configured for use with applicator 400.

Applicator 400 can also have a cartridge receiving chamber 425, similar to chamber 25, 225, 325, whereby the cartridge 450 is insertable into the cavity formed by chamber 425. In some examples using applicator 400, the treatment solution once applied from nozzle 460 can result in electrostatic and/or electrospun porous nanofibers that mimic important features of the extracellular matrix composition (ECM), including providing scaffolds favorable for tissue regeneration and wound healing. In some examples, such electrospun nanofibers can regulate skin cell behavior via transmembrane receptors or intracellular signaling pathways. Nanofibers of this example can incorporate bioactive material (e.g., DNA, enzymes, and growth factors) that can allow for the maintenance of proliferation and migration of primary cells seeded on the scaffolds. Nozzle 460 can be coupled to an electrospinning delivery system of cartridge 450 and motor M to apply a polymer fiber matrix to wounds for rapid healing, similar to applicator 300 and cartridge 350, respectively. As shown in FIG. 23, a motor M can be provided in communication with nozzle 460 and cartridge 450 as well as batteries B and circuit board C. A tube can be configured in cartridge 450 as a high-pressure supply tube and connected to and in fluid communication with a storage tank of cartridge 450. In some examples, a pump can be provided with applicator 400, similar to applicator 300, that can pressurize storage 454 and allow treatment solution to be forced through nozzle 460.

Figure 24A:
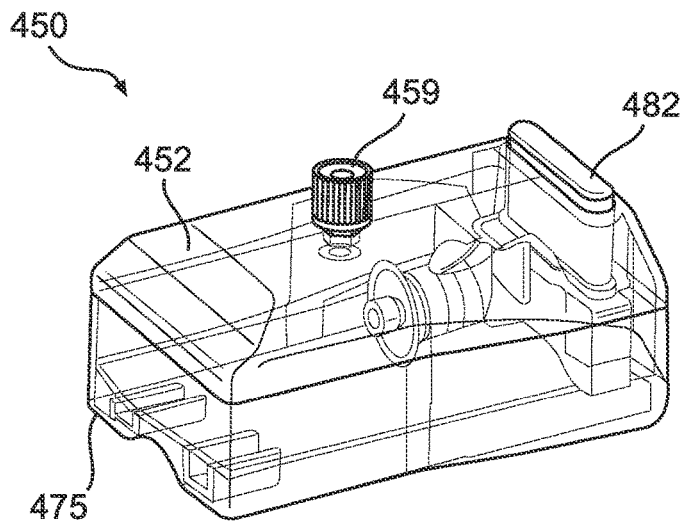
FIGS. 24A-24C depicts perspective views of an example cartridge in FIG. 22.
Figure 24B:
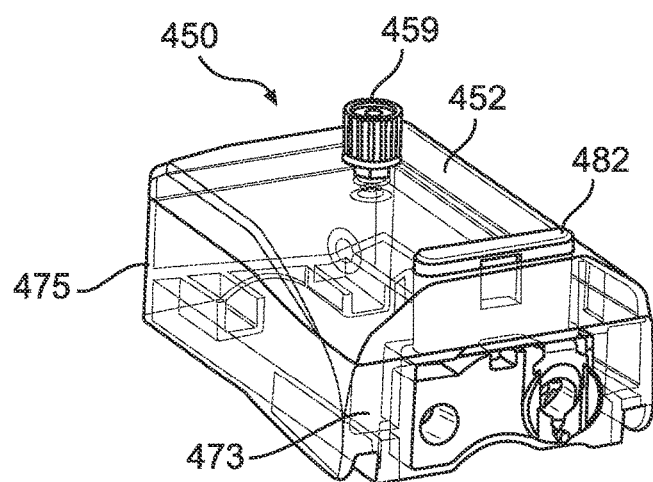
Figure 24C:
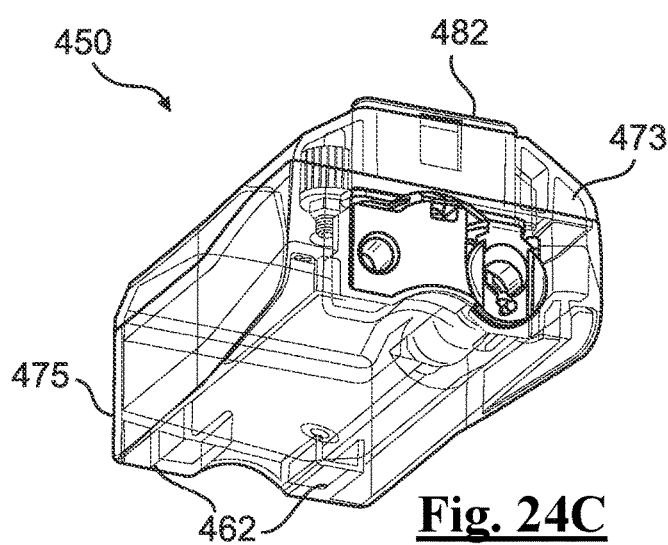

FIG. 24A through 24C show various perspective views of cartridge 450. Cartridge 450 can include a forward motor receiving face 473 configured to mechanically coupled to motor M when assembled with applicator 400. Cartridge 450 can also include a rear nozzle receiving face 475 opposite face 473 on which one or more nozzle face mounts 462 can be selectively positioned to guide, align, and slideably receive nozzle 460. For example, as shown in FIG. 23, nozzle 460 include alignment guides outwardly extended from the nozzle body of nozzle 460, whereby each guide is configured to align, mate and allow the nozzle to be properly aligned into an assembly configuration with face 473 until nozzle 460 is in fluid communication with treatment solution of treatment solution storage 454 disposed internal to cartridge 450 and motor M or vice versa (e.g., guide cartridge 450 into an assembled position with applicator 400) A nozzle channel 476 can be provided in a lower surface of cartridge 450 similarly configured to slideably guide nozzle into position or vice versa (e.g., guide cartridge 450 into an assembled position with applicator 400).

As can be seen, cartridge 450 may also include release button 482 that is positioned at least partially on an upper surface of housing 452. In some examples, button 482 can be connected to cartridge 450 via a bias member (e.g., a spring) that is operatively connected to or immediately adjacent surface. Further, housing 452 can include a hole in its upper surface through which button 482 can move between locked and unlocked states. In use, moving button 482 (e.g., up and down) can cause button 482 to securely lock cartridge 450 with applicator 400 as shown in FIG. 22 or it can release cartridge 450 therefrom into the unlocked state, as needed or required.

Storage 454 can be filled with a single treatment solution formulation or multiple treatment solution formulations, including those containing solvent(s), polymer(s), and/or other active ingredients or medicines. Storage 454 can be constructed from solvent resistant materials. Cartridge can also include aperture 459 on an upper surface of the housing 452 for receiving treatment solution (e.g., a needle can deliver the solution therethrough). In some examples, aperture 459 can include one or more caps or valve mechanisms for controlling flow of treatment solution therethrough.

FIG. 25 depicts a schematic overview of an example electrical field at a wound site of a patient, whereby the electric vector as it relates to cell migration is shown. In some examples, the applicator of this disclosure can use a high-pressure pump P (e.g., 160-180 psi) to pressurize the fluid and the electrostatic module of its cartridge (50/250) can charge and ionize molecules of the respective treatment solution. The treatment solution can be applied through a respective nozzle as fine charged, uniformly distributed mist and adhered to the treatment site from all directions with the help of electrostatic attraction. In certain examples, the applicator can include a flowmeter and associated circuit. The amount of treatment solution in operation can be recorded as a discrete record line in the internal memory of the computing system of the applicator. The records can also be accessed and/or saved and downloaded wirelessly (e.g., Bluetooth® via a mobile device or some other RF protocol).

The applicator can include an internal power supply powered by battery pack of nominal voltage 14.8V, with a maximum voltage is 16.8V). One or more LEDs can also be included to provide indications, including information related to the treatment solution or the power of the applicator. For example, a blue LED can be used as Bluetooth® indicator to the user (e.g., when no effective connection is set up, a blue LED indicator keeps on flashing slowly).

After successfully connected to a mobile device (e.g., see FIG. 26 and FIG. 28), the respective applicator can automatically transmit data about the current working conditions of the applicator, including record number, battery power, flow rate of the treatment solution, and/or the like. Previous records can also be accessed, viewed, and/or saved wirelessly by the mobile device whereby each record line can include a record number, date and time (if any), initial power level, final power level, total treatment solution flow amount, validation code associated with the treatment solution (e.g., barcode associated with a silica gel of the treatment solution), and/or the like.

In some examples, if one or more pulse signals are received from a flowmeter of the system, the circuit can start to record the flow and other associated data. If no such pulse signals are received, however, no recording operation can be actuated. Further, if no connection is established with a mobile device, "00" will be written to the date/time field, otherwise, actual starting date and time (derived from portable device) will be saved for that record.

The applicator can include one or more batteries B powered by exchangeable battery pack of nominal voltage 14.8V (maximum voltage is 16.8V). In some examples, battery B can include four 18650 cells (3.7V each) connected in series. The capacity can be doubled by doubling the cell quantity and standby current can be less than 10 uA. In some examples, battery power indication can be reflected in one or more LEDs. For example, four green LEDS can mean >16 V; three green LEDs can mean >14.6V; two green LEDs can mean >13.2V; 1 green LED can mean >12V; one red LED can mean <11.8V. In such an example, the applicator may not be activated by its actuator 35/235. Further, in some examples, if no flow by the treatment solution is recorded for a predetermined duration of time (e.g., 30 seconds after actuation of pump P), the applicator can be configured to deactivate automatically and fast flash to indicate the issue.

In some examples, a wireless module of the mobile device and/or applicator has to go through hand-shaking process in order to avoid connection with other irrelevant application of the mobile device. In such respects, after successfully connected to the mobile device, the applicator can automatically transmit data about the current working condition, including current cumulated record number, battery power settings, treatment solution flow rate, treatment solution levels and properties (e.g., treatment solution type including concentration of stem cells, medication, disinfectant, etc.). In some examples, the user in an application resident in the mobile device can also read every set of data previously recorded. In some examples, the memory can store up to 4000 sets of data and once the memory becomes full, new data can overwrite the old data.

Figure 26:
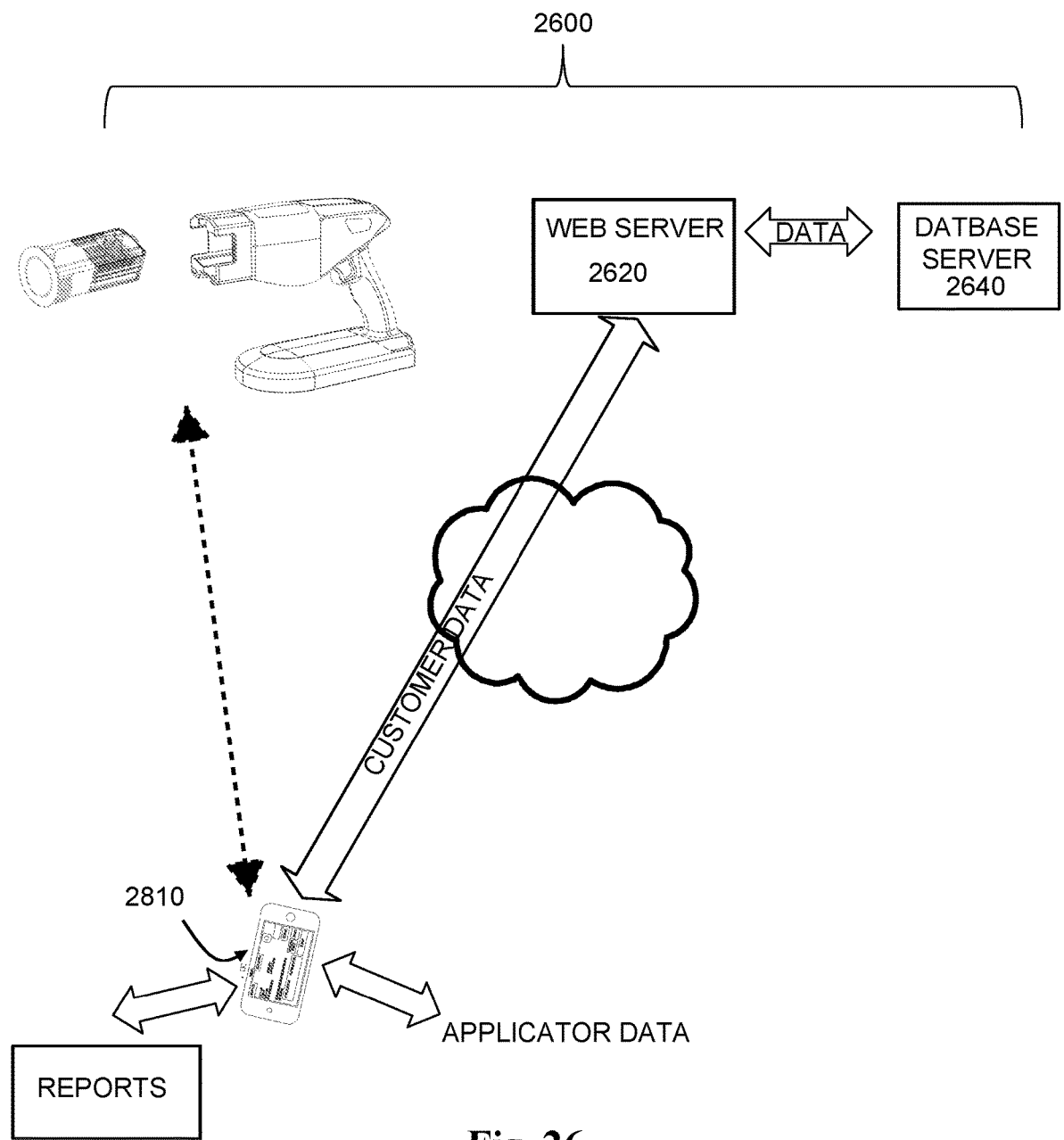
FIG. 26 depicts an illustration of system architecture according to an example embodiment of this disclosure.
Figure 28:
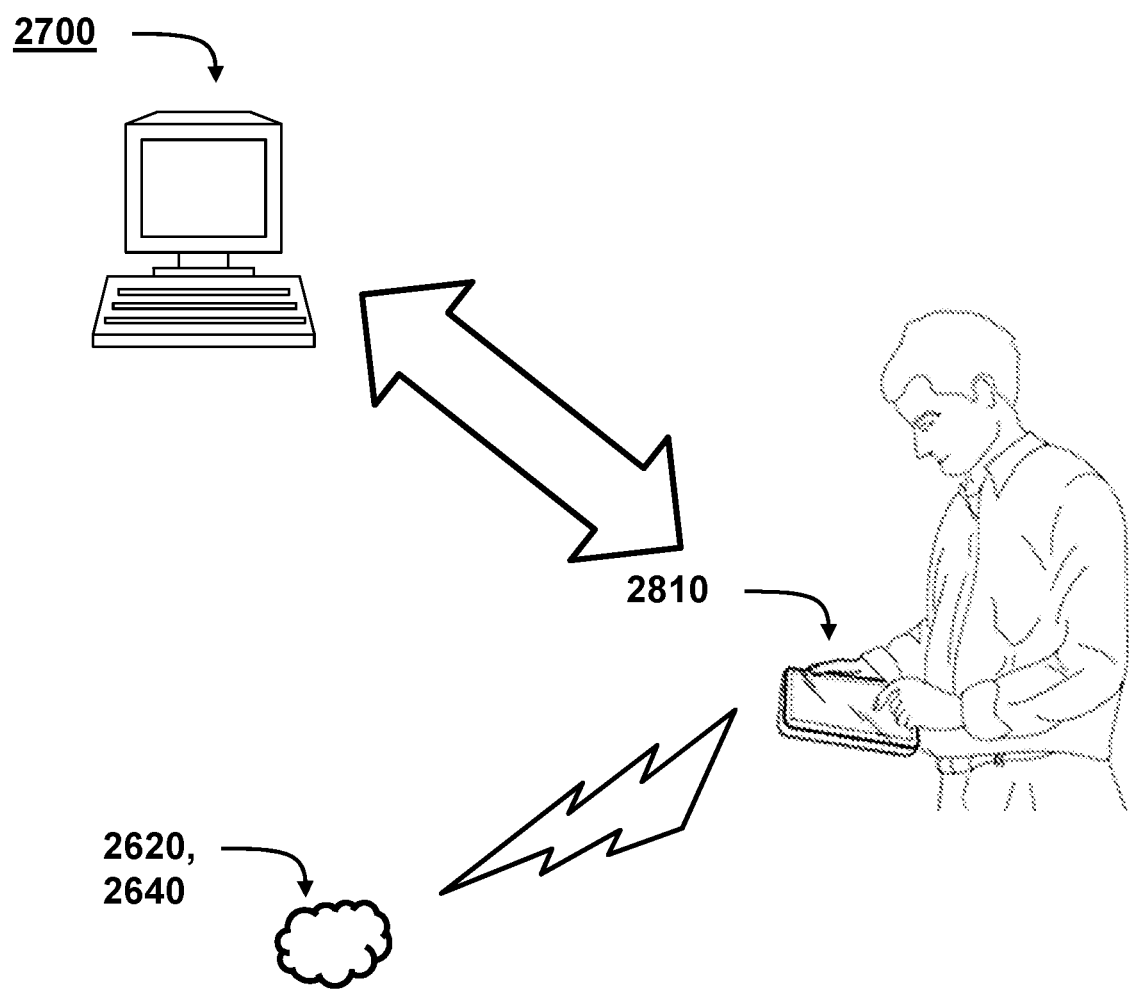
FIG. 28 is a computer architecture diagram showing a general computing system capable of implementing aspects of the present disclosure in accordance with one or more embodiments described herein.

FIG. 26 depicts an illustration of system architecture according to an example embodiment of this disclosure. According to certain embodiments, system 2600 may comprise a user-facing front-end including software, firmware, and/or hardware for monitoring and/or controlling any applicator of this disclosure prior, during, and post use. In some embodiments, this interface to the user may comprise a mobile application ("app") or other software executable on a mobile computing device 2810 as shown in FIG. 28 (e.g. a smart phone). It is understood that device 2810 can be an optical reader in accordance with this disclosure similarly configured to communicate with servers 2620, 2640 (e.g., optical reader 90/290). In another embodiment, the interface may comprise a web-based application accessible through a browser or other software, or a desktop application. In some examples, the mobile app may include a client for managing one or more locations where any applicator of this disclosure (or applicators) is being used. The app can be configured to provide or support functionality for managing any applicator of this disclosure. Moreover, the app may provide routine operation setting and scheduling with manual takeover of any applicator of this disclosure, role management, alerts during manual and automated control; and/or comment and sharing functionalities with support associated with the treatment solution of the applicator. According to certain examples, the app may present information about associated treatment solution, the patient, the end-user, the treatment site, dosing, or the like, in a dashboard view. In an example, the operational status and/or battery charge of applicator may be displayed and/or other displayable information may include patient destination, position or settings of a respective nozzle, data associated with treatment solution, etc. Selecting a user interface item may bring up a view with editable details and controls to manage status of the applicator.

According to certain examples, the user may receive notifications (e.g. alert messages) indicating the status of one or more current operations of a respective applicator. For example, when a new operation starts, the user may receive a notification through the app. Forms of notification include app notification within the app itself, email, and messaging (e.g., SMS, MMS, etc.). In some examples, a suitable applicator may be selected for an operation automatically based on one or more treatment parameters.

System 2600 can include any applicator of this disclosure, a web server 2620, a database server 2640, each connected directly or wirelessly (e.g., 3G/4G, RF, a local wireless network, and/or the like). The database server 2640 can be operatively connected to one or more web servers 2620 across one or more networks, each server operable to permanently store and/or continuously update a database of master data (e.g., data of the respective applicator, patient, treatment solution, etc.).

Server 2620 can include back-end architecture may comprise, or be in communication with, one or more of database server 2640, whereby functionality of system 300 may be split between multiple servers, which may be provided by one or more discrete providers. In an example embodiment, database server 2640 may store master data as well as logging and trace information. Software of the database server may be based on the object-relational database system PostgresSQL the database server is not so limited other approaches may be used as needed or required. This database server 2640 is not limited to only organizing and storing data and instead, it may be also used to eliminate a need of having an application server (e.g. 2nd Layer). In some embodiments, almost every functional requirement may be realized by using the database's programming language, PL/pgSQL. The database may also provide an API to the web server 2620 for data interchange based on JSON specifications. In some embodiments, the database server 2640 may also directly interact with the described functionality of respective applicator and/or mobile device 2810.

Figure 27:
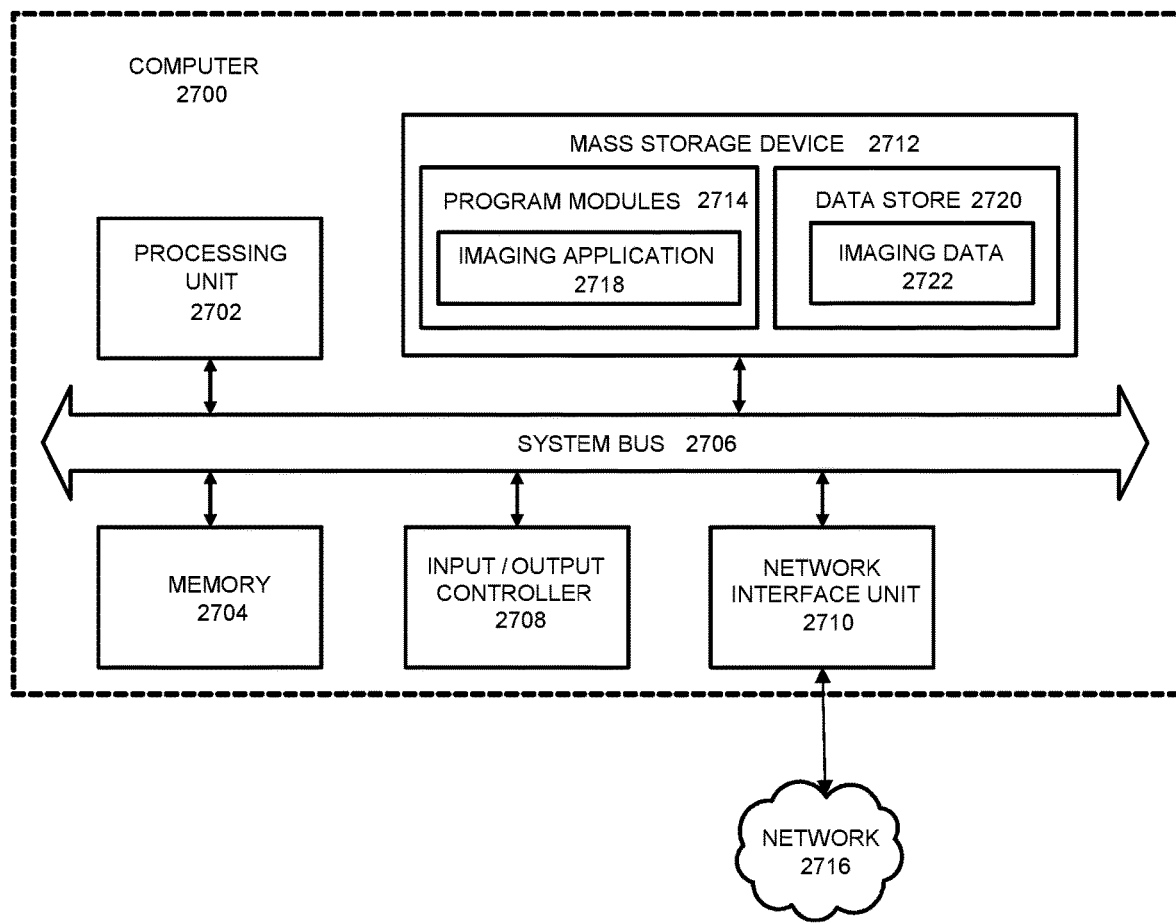
FIG. 27 is a computer architecture diagram showing a general computing system capable of implementing aspects of the present disclosure in accordance with one or more embodiments described herein.

FIG. 27 is a computer architecture diagram showing a general computing system capable of implementing aspects of the present disclosure in accordance with one or more embodiments described herein. A computer 2700 may be configured to perform one or more functions associated with embodiments of this disclosure. For example, the computer 2700 may be configured to perform operations in order to manage and effectively use respective applicator and deliver treatment solution to a respective patient. It should be appreciated that the computer 2700 may be implemented within a single computing device or a computing system formed with multiple connected computing devices. The computer 2700 may be configured to perform various distributed computing tasks, in which processing and/or storage resources may be distributed among the multiple devices. The data acquisition and display computer 2750 and/or operator console 2710 of the system shown in FIG. 27 may include one or more systems and components of the computer 2700.

As shown, the computer 2700 includes a processing unit 2702 ("CPU"), a system memory 2704, and a system bus 2706 that couples the memory 2704 to the CPU 2702. The computer 2700 further includes a mass storage device 2712 for storing program modules 2714. The program modules 2714 may be operable to analyze and/or modify current settings of the applicator, as well as individualize treatment of a patient, including the manner and amount of treatment solution delivered to a patient. For example, to cause the computer 2700 use the applicator with respect to treatment site of a patient as described in any of the figures of this disclosure. The program modules 2714 may include an imaging application 2718 for performing data acquisition and/or processing functions as described herein, for example to acquire and/or process image data corresponding to magnetic resonance imaging of an area of interest. The computer 2700 can include a data store 2720 for storing data that may include imaging-related data 2722 such as acquired data from the implementation of magnetic resonance imaging in accordance with various embodiments of the present disclosure.

The mass storage device 2712 is connected to the CPU 2702 through a mass storage controller (not shown) connected to the bus 2706. The mass storage device 2712 and its associated computer-storage media provide non-volatile storage for the computer 2700. Although the description of computer-storage media contained herein refers to a mass storage device, such as a hard disk or CD-ROM drive, it should be appreciated by those skilled in the art that computer-storage media can be any available computer storage media that can be accessed by the computer 2700.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 2700. "Computer storage media", "computer-readable storage medium" or "computer-readable storage media" as described herein do not include transitory signals.

According to various embodiments, the computer 2700 may operate in a networked environment using connections to other local or remote computers through a network 2716 via a network interface unit 2710 connected to the bus 2706. The network interface unit 2710 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 2700 may also include an input/output controller 2708 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 2700. The bus 2706 may enable the processing unit 2702 to read code and/or data to/from the mass storage device 2712 or other computer-storage media.

The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state or may include rotating media storing magnetically-encoded information. The program modules 2714, which include the imaging application 2718, may include instructions that, when loaded into the processing unit 2702 and executed, cause the computer 2700 to provide functions associated with one or more embodiments illustrated in the figures of this disclosure. The program modules 2714 may also provide various tools or techniques by which the computer 2700 may participate within the overall systems or operating environments using the components, flows, and data structures discussed throughout this description.

In general, the program modules 2714 may, when loaded into the processing unit 2702 and executed, transform the processing unit 2702 and the overall computer 2700 from a general-purpose computing system into a special-purpose computing system. The processing unit 2702 may be constructed from any number of transistors or other discrete circuit elements, which may individually or collectively assume any number of states. More specifically, the processing unit 2702 may operate as a finite-state machine, in response to executable instructions contained within the program modules 2714. These computer-executable instructions may transform the processing unit 2702 by specifying how the processing unit 2702 transitions between states, thereby transforming the transistors or other discrete hardware elements constituting the processing unit 2702.

Encoding the program modules 2714 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer storage media are implemented as semiconductor-based memory, the program modules 2714 may transform the physical state of the semiconductor memory, when the software is encoded therein. For example, the program modules 2714 may transform the state of transistors, capacitors, or other discrete circuit elements constituting the semiconductor memory.

As another example, the computer storage media may be implemented using magnetic or optical technology. In such implementations, the program modules 2714 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

FIG. 28 depicts a schematic overview of an example embodiment of a mobile device 2810 for use with the applicator and any corresponding treatment solution. The mobile device 2810 may be any electronic device configured to capture images, such as a mobile phone, media player, portable gaming device, tablet computer, or the like. It is noted that the present disclosure is not limited to any single type of mobile device. Device 2810 can be wirelessly connected and controlled by an external computing device (e.g., servers 2620, 2640) and/or system (e.g., computing system 2700), such as any herein disclosed computing systems, whereby such external system can be operable to execute instructions related to a treatment protocol in connection with the applicator, according to any of the previously disclosed embodiments of this disclosure. Alternatively, device 2810 can transmit data of the respective applicator and any corresponding treatment solution, treatment protocol, or the like for a patient and their treatment site, locally.

Device 2810 may operatively communicate with the external computing device through an application resident on device 2810. Device 2810 may include an optical system, such as an onboard camera, configured to capture images or video of the treatment site (e.g., a wound site) in order to analyze and/or classify the treatment site (e.g., identify the type of treatment needed).

Exemplary architecture of device 2810 can include a central processing unit, where computer instructions are processed; a display interface that acts as a communication interface and provides functions for rendering video, graphics, images, and texts on the display and a keyboard interface that provides a communication interface to a keyboard; and a pointing device interface that provides a communication interface to device 2810 and/or any external computing devices coupled thereto. Example embodiments of the architecture may include an antenna interface that provides a communication interface to an antenna. Example embodiments may include a network connection interface that may provide a communication interface to an external device or network.

In certain embodiments, a camera interface may be provided that acts as a communication interface and provides functions for capturing digital images from the onboard camera and capabilities of visualizing certain aspects of the treatment site or corresponding treatment solution, including any tracking material associated therewith (e.g., silica gel with tracking features for authenticating a treatment solution for a patient). According to example embodiments, a random access memory (RAM) may be provided, where computer instructions and data may be stored in a volatile memory device for processing by the CPU. The architecture may include a read-only memory (ROM) where invariant low-level system code or data for basic system functions such as basic input and output (I/O), startup, or reception of keystrokes from a keyboard are stored in a non-volatile memory device. According to an example embodiment, the architecture may include a storage medium or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system, application programs (including, for example, a web browser application, a widget or gadget engine, and or other applications, as necessary) and data files are stored. According to an example embodiment, the architecture may include a power source that provides an appropriate alternating current (AC) or direct current (DC) to power components. According to an example embodiment, the architecture may include a telephony subsystem that allows the device to transmit and receive sound over a telephone network. The constituent devices and the CPU may communicate with each other over a bus.

Figure 29:
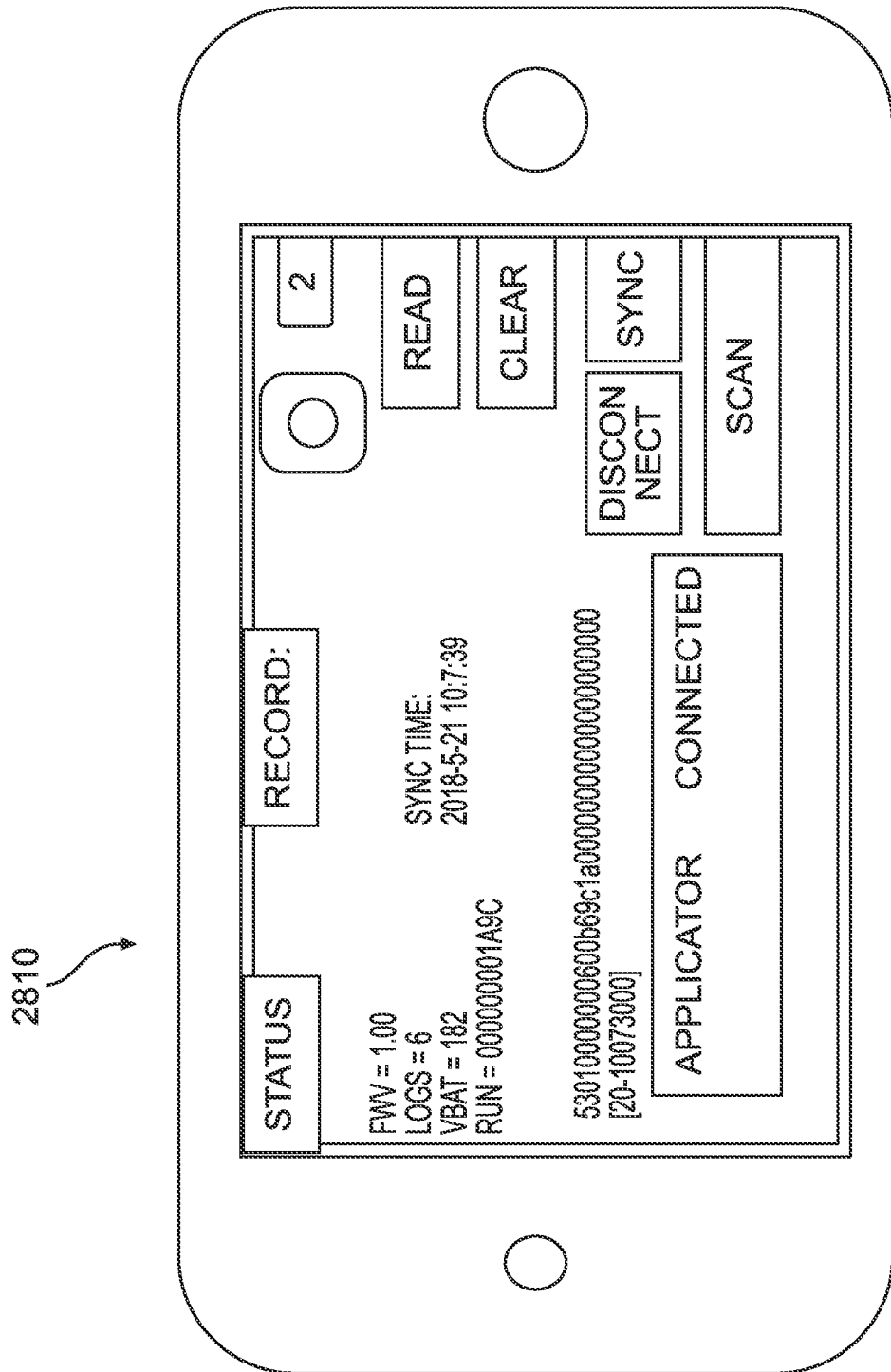
FIG. 29 depicts an exemplary event viewer of an app on a mobile device.

Turning to FIG. 29, an exemplary live or previous event viewer of an application of mobile device 2810 is depicted. As previously discussed, an exemplary application of device 2810 can include any number of different controls and indicators for the respective applicator and corresponding end-users and/or patients. For example, in FIG. 29, the viewer is shown displaying information related to an event having a sync timestamp, connectivity status with the respective applicator wherein one or more alerts can also be defined, including power levels, treatment solution data, number of logged events, run times, etc.

Figure 30:
FIG. 30 depicts a schematic overview of an example method of this disclosure.

In FIG. 30, a method 3000 is disclosed that includes step 3010 electrostatically charging a treatment solution for a treatment site of a patient; and step 3020 uniformly applying, by an applicator, the treatment solution on the treatment site of the patient.

In FIG. 31, a method 3100 is disclosed that includes step 3110 electrostatically charging a treatment solution for a treatment site of a patient; step 3120 uniformly applying, by an applicator, the treatment solution on the treatment site of the patient; step 3130 forming the treatment solution with a tracking material mixed with at least one stem cells and/or a disinfectant for the treatment site; step 3140 authenticating, with an optical reader external to the applicator, contents of the treatment solution; and step 3150 if authentic, then carrying out the step of uniformly applying, by the applicator, the treatment solution on the treatment site of the patient.

Figure 32:
FIG. 32 depicts a schematic overview of an example method of this disclosure.

In FIG. 32, a method 3200 of producing a liquid bandage comprising an electrospun fibrous mat is disclosed. Method 3200 can include step 3210 applying electric potentials to a treatment solution of a cartridge in an applicator for producing and delivering the liquid bandage on a treatment site. The applicator can be any of this disclosure, including applicator 300. Method 3200 can also include step 3220 electrospinning, by the rotatable needle, the treatment solution.

In certain examples, a novel charging method is also disclosed along with other embodiments discussed herein that can provide a uniform application (e.g., a mist, spray, or grouping of droplets of a treatment solution for targeted application). Example systems of this disclosure also provide for instrumentation that can track a patient's treatment solution to ensure the proper solution is applied to the correct patient.

In some examples, the applicator and related systems of this disclosure are configured for delivering treatment solution that includes acne medication and/or therapeutics using a piezoelectric system as described herein. A cartridge in this example can be disposable and include the treatment solution that is delivered to the site of interest by the doctor in an outpatient setting. It is contemplated that the applicator and related systems can be configured to treat types of acne vulgaris, including non-inflammatory and inflammatory, whereby the treatment solution can include prescription and/or over-the-counter medication. This is particularly significant since the projected global market is so large for acne treatments alone. (e.g., The global marked in 2016 was $4.9 billion USD and has been projected to be more than $7 billion USD by 2025). As stated, the treatment solution can include prescribed medication that can be used for anti-inflammatory, anti-bacterial, and anti-infection. The treatment solution in some examples can include medication such as benzoyl-peroxide and topical retionoid therapy which can be delivered by the electrostatic system of this disclosure.

In some examples, delivery of human stem cells can include the following operation parameters: using 250V; a capacitance of 200 uF; a resistance of 1000 Ohm and an exponential decay waveform. It is understood that electrical stimulation (ES) can also be used on mesenchymal stem cells (MSC) at a relatively low stimulation (e.g., 5V/cm, 8 ms, 5 Hz) to show increase of TGF-b (Transforming growth factor-beta) and BMPs (Bone morphogenetic proteins). However, a lower ES (1V/cm, 8 ms, 5 Hz) is also contemplated as needed or required.

Another aspect to electrostatic delivery of the treatment solution can be additive components to the reagent cartridge that would allow for the adherence of cellular material by incorporating a scaffold protein such as laminin, fibrin, collagen, or certain components of the ECM (Extracellular matrix). These biomolecules are able to provide added support for delivered stem cells in the healing process of any type of wound. It may also include proprietary ECM factors that will allow for increased viability of delivered cells to the area of interest.

The clinician would anticipate achieving acceleration in healing, prevention of wound contracture and scar formation, earlier wound closure, and ideally regeneration of the skin. Their therapeutic potential is largely due to their capability to secrete pro-regenerative cytokines, causing them to be an attractive choice for the treatment of chronic wounds and burns. The stem cell cartridge aseptically loaded onto the electrostatic delivery device and sprayed on wound site. The solution containing the stem cells will be of a physiological relevant buffer that may also include certain growth factors or trophic factors that will support and accelerate the healing actions of the therapeutic stem cell. Such factors may include FGF (Fibroblast growth factor), EGF (Epidermal growth factor), PDGF (Platelet-derived growth factor), HGF (Hepatocyte growth factor), VEGF (Vascular endothelial growth factor, and TGF-beta (Transforming growth factor-beta)).

The stem cell cartridge reagent can also have the ability to carry gene therapy material in order to target and rectify any genetic defect associated with epidermal mutation caused by either DNA, RNA, Growth factor, substrate, and/or cellular defect. The stem cell solution may also include pharmaceutical reagents such as small molecules, bioactive peptides, and/or antibodies that may offer beneficial aspects to any of the different phases associated with the process of any type of wound healing.

In some examples, collagen is secreted by fibroblasts in the body and being a structural protein, stimulates cellular migration. Collagen can attract fibroblasts and thus enhances the deposition of new tissue during wound healing. Collagen type-I can be a biocompatible abundant protein existing in connective tissues of body. Collagen can play a major role in hemostasis in order to promote the wound healing and supports fibroblasts growth, attachment, differentiation, and migration of keratinocytes directly.

In some examples, chitosan is another polymer contemplated for use with the treatment solution. The particular flexibility and elasticity of chitosan can significantly reduce scar development when used for burn wound healing. Chitosan can stimulate collagen synthesis and FGF due to the chitosan electrostatic function, which can enhance the wound-healing rate.

In some examples, bioprinting using a piezoelectric actuator for the delivery of biomaterial as a skin dressing is also contemplated with the applicator, system, and cartridges of this disclosure. Typically, the bioink can physically serve as cell-laden hydrogels or sacrificial support materials removed immediately after printing or as mechanical support materials that provide specific mechanical characteristics to the tissue. Bioinks can be fully natural materials such as collagen, fibrin, HA, and alginate, which can be used in the form of hydrogels for the cells or synthetic materials. Such materials can include PCL, polylactide (PLA), polyglycolide (PGA), poly(lactic-co-glycolic acid) (PLGA), and polyethylene glycol (PEG) polymers or hybrid biomaterials that contain a combination of natural and synthetic materials, which can provide mechanical support such as increased cell viability compared to a pneumatic expulsion method.

PGA is one material with excellent degradation behavior. Additionally, synthetic polymers such as polyvinyldene fluoride (PVDF) and polypropylene (PP) are contemplated for use as wound dressing materials. Poly (ε-caprolactone) (PCL), polyethylene glycol (PEG), polyethylene oxide (PEO), polyurethane (PU), poly (vinyl alcohol) (PVA), poly (lactic acid) (PLA), and poly (lactic-co-glycolic acid) (PLGA) are synthetic materials contemplated for use that have been approved by Food and Drug Administration (FDA) for biomedical applications, due to their good biocompatibility, biodegradability and non-toxic properties.

In some examples, the applicators and related systems has the unique features of being a handheld portable electrostatic device with a piezoelectric nozzle configured to provide most, if not all, aspects of wound care and management. In some examples, multiple cartridges are contemplated for use, either simultaneously or otherwise, whereby the system is able to offer disinfectant and analgesic properties to any type of wound and/or burn. The applicators and related systems advantageously include the ability to deliver (e.g., spray) therapeutic biologics, such as stem cells, on the site of interest for accelerated wound healing with the potential capability of tracking the source of the generated cells.

In some examples, the applicators and related systems can be configured for delivering treatment solution to a patient's throat. For example, the delivery of medication for sore throats can be difficult given the amount of pain a patient can encounter given the degree of oral infection. The current standard of care and intervention is oral mouth wash and/or spray with anesthetic (e.g., codeine) which can be painful and cumbersome for the patient to perform. The electrostatic delivery system of the applicators of this disclosure are therefore configured to resolve these problems. In particular, the applicators and related systems of this disclosure are configured to deliver treatment solution to treatment sites such as an infected throat that can include substantially less treatment solution than what is currently used and the electrostatically charged medication can reach increased area where the mouth wash is presently unable to cover. In some embodiments, the applicator can use a transepithelial potential (TEP) that is established in the esophagus/airway of the patient and if disturbed by sores or open wounds, this airway can act as a cue or target for charged treatment solution to cover area of interest at the treatment site.

In some examples, the applicators and related systems can be configured for intra-nasal delivery of treatment solution. For example, there is an emerging therapeutic potential for the intra-nasal delivery of treatment solution, including stem cells, for the therapeutic treatment of potential central nervous system (CNS) disorders starting from early neonatal hypoxia ischemic brain damage, Glioblastoma, stroke, as well as other neurodegenerative conditions. Some examples of neurodegenerative conditions include Parkinson's, Huntingtons, and Alzheimer's. In this respect, applicators of this disclosure can be configured to electrostatically charge stem cells of interest and administer them through the nasal cavity. Migration of stem cells can be via olfactory nerves and/or trigeminal nerve which can innervates the olfactory area in the distal region of the nasal cavity. The therapeutic value of this embodiment and its use piezoelectric intra-nasal delivery of mesenchymal stem cells (MSC) or other stem cell (embryonic, neuronal) can be of a huge benefit in order to address an unmet medical need for many patients.

In some examples, the applicators and related systems can be configured for also treating the cardiovascular system. For example, the major component of heart attack is the accumulation of plaque on the endothelia wall of the artery which brings about the occlusion of blood flow and eventual heart failure. A common therapy for preventative heart attack measures include placement of a stent. However, use of a stent could lead to restenosis or other conditions that further damage the arterial wall. The applicators and related systems of this disclosure can resolve this by utilizing a disturbed transepithelial potential and electrostatic charged stem cells that can migrate to the injured site via electric field cues and offer therapeutic potential in restoring the epithelial function and arterial integrity.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method for applying electrically spun fibers to a site of interest, the method comprising:
   loading a cartridge into a cartridge receiving chamber of an applicator housing wherein the cartridge comprises a natural or synthetic polymer and an elongate tubular member;
   electrospinning, by a motor in the applicator housing directly driving the elongate tubular member of the cartridge, the natural or synthetic polymer in the cartridge thereby generating electrically spun fibers of the polymer; and
   delivering, by a nozzle of the cartridge, the electrically spun fibers out of the cartridge to the site of interest.

2. The method of claim 1, further comprising, prior to the delivering step, charging electrostatically, by the cartridge, the natural or synthetic polymer.

3. The method of claim 1, further comprising, prior to the delivering step, applying an electrical charge, by the cartridge, to the natural or synthetic polymer.

4. A method for applying electrically spun fibers to a site of interest, the method comprising:
   loading a cartridge into a cartridge receiving chamber of an applicator housing wherein the cartridge comprises a natural or synthetic polymer and an elongate tubular member;
   processing data about current working conditions of the cartridge, the current working conditions comprising one or more of nozzle settings of the cartridge, end-user information, polymer solution flow rate, polymer levels and polymer properties;
   electrospinning, by a motor in the applicator housing driving the elongate tubular member of the cartridge, the natural or synthetic polymer in the cartridge thereby generating electrically spun fibers of the polymer; and
   delivering, by a nozzle of the cartridge, the electrically spun fibers out of the cartridge to the site of interest.

5. The method of claim 1, further comprising, prior to the electrospinning step, storing the polymer in a storage chamber within a cartridge housing of the cartridge.

6. The method of claim 1, wherein delivering the electrically spun fiber of the polymer out of the applicator comprises passing the electrically spun fiber through the nozzle of the cartridge and producing different electric potentials on the nozzle.

7. The method of claim 1, further comprising, prior to delivering step, forcing the polymer, by an electrospinning turbine of the applicator, through the nozzle of the cartridge thereby accelerating the flow of the polymer.

8. The method of claim 1, wherein upon loading the cartridge into the cartridge receiving chamber, a pressure pump within the applicator housing is in fluid communication with the cartridge.

9. The method of claim 4, further comprising, prior to the electrospinning step, storing the polymer in a storage tank of the cartridge.

10. A method for applying an electrospun fiber to a treatment site, the method comprising:

loading a cartridge into a cartridge receiving chamber of an applicator housing, wherein the cartridge comprises an elongate tubular member and an electrospinning medium in a storage tank of the cartridge;

pressurizing the electrospinning medium inside the cartridge by a force generated by a motor and piston thereby generating an electrospun fiber; and delivering, by a nozzle of the cartridge, the electrospun fiber out of the cartridge to the treatment site.

11. The method of claim 10, wherein the electrospun fiber comprises a liquid bandage, an antiseptic solution, an antimicrobial solution, a pharmaceutical agent, a reagent comprising an analgesic property, cellular or acellular materials, a disinfectant, or an antifungal.

12. A method of claim 10, wherein the electrospun fiber forms a liquid bandage matrix comprising an electrospun fibrous mat on the treatment site.

13. The method of claim 10, further comprising, applying an electrical potential to the electrospun fiber prior to the delivering step.

14. The method of claim 1, further comprising, subjecting the electrically spun fibers to high velocity airflow to dry a solvent in the electrically spun fibers.

15. The method of claim 1, further comprising, loading a second cartridge into the cartridge receiving chamber of the applicator housing, the second cartridge comprising contents different from the natural or synthetic polymer of the cartridge.

16. The method of claim 15, wherein the contents of the second cartridge comprise a liquid bandage.

* * * * *